(12) United States Patent
Backer et al.

(10) Patent No.: US 7,314,879 B2
(45) Date of Patent: Jan. 1, 2008

(54) MELANOCORTIN RECEPTOR AGONISTS

(75) Inventors: Ryan Thomas Backer, Indianapolis, IN (US); Caño Ivan Collado, Alcobendas (ES); Oscar De Frutos-Garcia, Alcobendas (ES); Christopher William Doecke, Indianapolis, IN (US); Matthew Joseph Fisher, Mooresville, IN (US); Steven Lee Kuklish, Fishers, IN (US); Vincent Mancuso, Mont-Saint-Guibert (BE); Michael John Martinelli, Zionsville, IN (US); Jeffrey Thomas Mullaney, Indianapolis, IN (US); Paul Leslie Ornstein, Carmel, IN (US); Chaoyu Xie, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 358 days.

(21) Appl. No.: 10/500,476

(22) PCT Filed: Jan. 21, 2003

(86) PCT No.: PCT/US03/00033

§ 371 (c)(1),
(2), (4) Date: Jun. 29, 2004

(87) PCT Pub. No.: WO03/061660

PCT Pub. Date: Jul. 31, 2003

(65) Prior Publication Data

US 2005/0075344 A1    Apr. 7, 2005

Related U.S. Application Data

(60) Provisional application No. 60/351,200, filed on Jan. 23, 2002.

(51) Int. Cl.
*A61K 31/496* (2006.01)
*C07D 401/12* (2006.01)
*C07D 405/12* (2006.01)
*C07D 407/12* (2006.01)

(52) U.S. Cl. ............... 514/253.01; 514/253.05; 514/254.09; 514/253.12; 514/253.13; 544/363; 544/364; 544/373

(58) Field of Classification Search ............... 544/363, 544/373, 364; 514/253.05, 254.09, 253.01, 514/253.12, 253.13
See application file for complete search history.

(56) References Cited

U.S. PATENT DOCUMENTS 6,294,534 B1    9/2001    Nargund et al.

FOREIGN PATENT DOCUMENTS

| WO | WO 94 13696 A | 6/1994 |
|---|---|---|
| WO | WO 99 55679 A | 11/1999 |
| WO | WO 99 64002 A | 12/1999 |
| WO | WO 00 74679 A | 12/2000 |
| WO | WO 01 70337 A | 9/2001 |
| WO | WO 01 70708 A | 9/2001 |
| WO | WO 02 15909 A | 2/2002 |
| WO | WO 02 059095 | 8/2002 |
| WO | WO 02 059107 | 8/2002 |
| WO | WO 02 059108 A | 8/2002 |
| WO | WO 02 059117 | 8/2002 |
| WO | WO 02 070511 | 9/2002 |
| WO | 03/031410 A1 * | 4/2003 |

OTHER PUBLICATIONS

Vippagunta et al. Advanced Drug Delivery Reviews, vol. 48, pp. 3-26 (2001).*
Sebhat et al. Annual Reports in Medicinal Chemistry, vol. 38 pp. 31-40 (2003).*
Campfield et al. Science, vol. 280 pp. 1383-1387 (1998).*
Privileged structure based ligands for melanocortin receptors—4,4-Disubstituted piperidine derivatives. Kuklish, Steven L., et al., Bioorganic & Medicinal Chemistry Letters 16 (2006) 3843-3836.

* cited by examiner

*Primary Examiner*—Emily Bernhardt
(74) *Attorney, Agent, or Firm*—James B. Myers; Soonhee Jang

(57) ABSTRACT

The present invention relates to melanocortin receptor agonist of the formula (I): which is useful in the treatment for obesity, diabetes, and male and/or female sexual dysfunction

29 Claims, No Drawings

MELANOCORTIN RECEPTOR AGONISTS

This is the national stage application under 35 USC 371 for PCT/US03/00033, filed Jan. 21, 2003, which claims the benefit of U.S. Provisional Application Ser. No. 60/351,200, filed Jan. 23, 2002.

FIELD OF THE INVENTION

The present invention relates to melanocortin receptor agonists, and as such are useful in the treatment of disorders responsive to the activation of melanocortin receptors, such as obesity, diabetes, and male and/or female sexual dysfunction.

BACKGROUND OF THE INVENTION

Pro-opiomelanocortin (POMC) derived peptides are known to affect food intake. Several lines of evidence support the notion that the G-protein coupled receptors (GPCRS) of the melanocortin receptor (MC-R) family, several of which are expressed in the brain, are targets of POMC derived peptides involved in the control of food intake and metabolism.

Evidence for the involvement of MC-R in obesity includes: i) the agouti ($A^{vy}$) mouse which ectopically expresses an antagonist of the MC-1R, -3R and -4R is obese, indicating that blocking the action of these three MC-Rs can lead to hyperphagia and metabolic disorders; ii) MC-4R knockout mice (Huszar et al., Cell, 88:131-141, 1997) recapitulate the phenotype of the agouti mouse and these mice are obese; iii) the cyclic heptapeptide MC-1R, -3R, -4R, and -5R agonist melanotanin-II (MT-II) injected intracerebroventricularly (ICV) in rodents, reduces food intake in several animal feeding models (NPY, ob/ob, agouti, fasted) while ICV injected SHU-9119 (MC-3R, -4R antagonist; MC-1R and -5R agonist) reverses this effect and can induce hyperphagia; iv) chronic intraperitoneal treatment of Zucker fatty rats with an α-NDP-MSH derivative melanocytes. MC-2R is expressed in the adrenal gland and represents the ACTH receptor. MC-3R is expressed in the brain, gut and placenta and may be involved in the control of food intake and thermogenesis. MC-4R is uniquely expressed in the brain and its inactivation was shown to cause obesity. MC-5R is expressed in many tissues including white fat, placenta and exocrine glands. A low level of expression is also observed in the brain. MC-5R knock out mice reveal reduced sebaceous gland lipid production (Chen et al., *Cell*, 91:789-798, 1997).

Evidence for the involvement of MC-R in male and/or female sexual disfunction is detailed in WO 00/74670.

Melanocortin receptor agonist compounds were disclosed in WO 99/64002.

BRIEF SUMMARY OF THE INVENTION

The present invention relates to a compound of formula I:

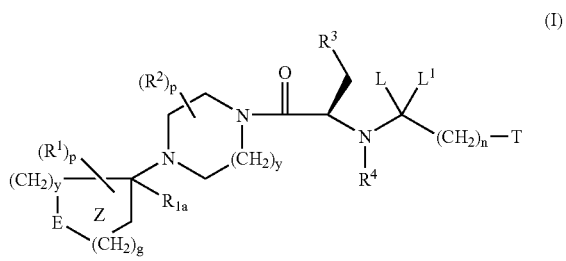

or a pharmaceutically acceptable salt, solvate or stereoisomer thereof, wherein:
L and $L^1$ are both hydrogen or combine together to form an oxo group;
E is: O, S, $NR^{1b}$, SO, $SO_2$, $CR^9$, or $C(R^9)_2$, provided that when E is $CR^9$, or $C(R^9)_2$, $R^9$ may combine with an adjacent $R^1$ to form a 5, 6, or 7-member saturated or unsaturated carbocycle;
wherein the Z ring has 0, or 1 double bond;
$R^1$ is: hydrogen,
  $C_1$-$C_8$ alkyl,
  $C_2$-$C_8$ alkenyl,
  $C_2$-$C_4$ haloalkyl
  (D)$C_3$-$C_7$ cycloalkyl,
  (D)phenyl,
  aryl, or
  $C(O)OC_1$-$C_8$ alkyl,
  wherein phenyl, aryl, alkenyl, and cycloalkyl groups are optionally substituted with hydroxy, halo, $C_1$-$C_8$ alkyl, $C_1$-$C_4$ alkoxy, $C_2$-$C_4$ haloalkyl, and (D)$C_3$-$C_7$ cycloalkyl provided that the halo, hydroxy are not substituted on a carbon atom adjacent to a heteroatom;
$R_{1a}$ is: hydrogen,
  $C_1$-$C_8$ alkyl,
  (D)$C_3$-$C_7$ cycloalkyl,
  (D)phenyl,
  (D)aryl,
  (D)heteroaryl;
  (D)C(O)$C_1$-$C_4$ alkyl,
  (D)C(O)O$C_1$-$C_4$ alkyl,
  $(CH_2)_m N(R^8)_2$,
  $(CH_2)_m NR^8 C(O)C_1$-$C_4$ alkyl,
  $(CH_2)_m NR^8 SO_2(C_1$-$C_4$ alkyl),
  $(CH_2)_m OR^8$,
  $(CH_2)_m SC_1$-$C_4$ alkyl,
  $(CH_2)_m SO(C_1$-$C_4$ alkyl),
  $(CH_2)_m SO_2(C_1$-$C_4$ alkyl), or
  $(CH_2)_m SO_2 N(R^8)_2$;
  wherein $C_1$-$C_8$ alkyl, $C_3$-$C_7$ cycloalkyl, phenyl, aryl and heteroaryl are optionally substituted with one to five substituents independently selected from the group consisting of perfluoro$C_1$-$C_4$ alkoxy, halo, hydroxy, $C_1$-$C_8$ alkyl, $C_1$-$C_4$ alkoxy, and $C_1$-$C_4$ haloalkyl; provided that halo and hydroxy groups are not substituted on a carbon atom adjacent to a heteroatom;
$R^{1b}$ is: hydrogen,
  $C_1$-$C_8$ alkyl,
  (D)$C_3$-$C_7$ cycloalkyl,
  $SO_2(C_1$-$C_8$ alkyl), (D)C(O)C$_1$-C$_4$ alkyl,
(D)C(O)OC$_1$-C$_4$ alkyl,
(D)CON(R$^8$)$_2$, or
SO$_2$(D)phenyl wherein the phenyl group is optionally substituted with one to five substituent selected from halo, and C$_1$-C$_8$ alkyl;

R$^2$ is: hydrogen,
C$_1$-C$_8$ alkyl,
CONHC$_1$-C$_4$ alkyl,
(D)phenyl, oxo, or
(D)C$_3$-C$_7$ cycloalkyl, provided that when R$^2$ is oxo, R$^2$ is on one of the ring carbon atoms adjacent to the nitrogen atom bearing the Z ring;

R$^3$ is: phenyl, aryl or thienyl;
wherein phenyl, aryl and thienyl are optionally substituted with one to three substituents independently selected from the group consisting of:
cyano, perfluoroC$_1$-C$_4$ alkoxy, halo, C$_1$-C$_8$ alkyl, (D)C$_3$-C$_7$ cycloalkyl, C$_1$-C$_4$ alkoxy, C$_1$-C$_4$ haloalkyl;

R$^4$ is: hydrogen,
C$_1$-C$_8$ alkyl,
CH$_2$(CH$_2$)$_m$C$_1$-C$_4$ alkoxy,
C(O)C$_1$-C$_4$ alkyl or
C(O)OC$_1$-C$_4$ alkyl;

R is: hydroxy,
halo,
C$_1$-C$_8$ alkyl,
C$_2$-C$_8$ alkenyl,
C$_1$-C$_8$ alkoxy,
C$_1$-C$_4$ haloalkyl,
(D)C$_3$-C$_7$ cycloalkyl,
(D)aryl,
(D)heteroaryl,
(D)C(O)C$_1$-C$_4$ alkyl,
(D)C(O)OC$_1$-C$_4$ alkyl,
(D)C(O)heteroaryl,
(D)N(R$^8$)$_2$,
(D)NR$^8$C(O)C$_1$-C$_4$ alkyl,
(D)NR$^8$SO$_2$(C$_1$-C$_4$ alkyl),
(D)OC$_1$-C$_4$ alkyl,
(D)OC(O)C$_1$-C$_4$ alkyl,
(D)heterocyclic,
(D)SC$_1$-C$_4$ alkyl, or
(D)SO$_2$N(R$^8$)$_2$;
wherein C$_1$-C$_8$ alkyl, C$_1$-C$_8$ alkoxy, C$_3$-C$_7$ cycloalkyl, phenyl, aryl, heterocyclic, and heteroaryl are optionally substituted with one to five substituents independently selected from R$^8$; and provided that when R is halo or hydroxy it is not substituted on a carbon adjacent to a heteroatom;

each R$^8$ is independently:
hydrogen,
oxo,
C$_1$-C$_8$ alkyl,
(D)C$_3$-C$_7$ cycloalkyl,
phenyl,
aryl or
heteroaryl,
wherein C$_1$-C$_8$ alkyl, C$_3$-C$_7$ cycloalkyl, phenyl, aryl and heteroaryl are optionally substituted with one to three substituents selected from the group consisting of C$_1$-C$_8$ alkyl, halo, and hydroxy; provided that the halo and hydroxy groups are not substituted on a carbon adjacent to a heteroatom;

T is:

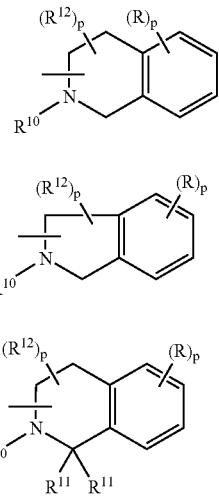 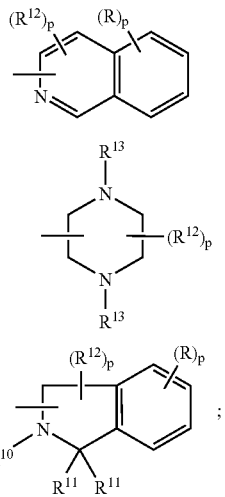

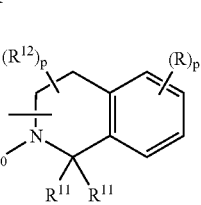 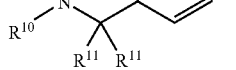

R$^9$ is independently:
hydrogen,
(C$_1$-C$_8$) alkyl,
C$_2$-C$_8$ alkenyl,
C(O)C$_1$-C$_8$ alkyl,
C$_2$-C$_8$ alkynyl,
phenyl,
aryl, or
heteroaryl;

R$^{10}$ is: hydrogen,
(C$_1$-C$_8$)alkyl,
C$_3$-C$_8$ alkenyl,
C(O)C$_1$-C$_8$ alkyl,
C$_2$-C$_8$ alkynyl,
phenyl,
aryl, or
heteroaryl;

R$^{11}$ is independently:
hydrogen, (C$_1$-C$_8$)alkyl, or (D)phenyl, or aryl;

R$^{12}$ is independently:
C$_1$-C$_8$ alkyl,
phenyl,
aryl,
heteroaryl,
(CH$_2$)$_n$N(R$^8$)$_2$,
(CH$_2$)$_n$NR$^8$C(O)C$_1$-C$_4$ alkyl,
(CH$_2$)$_n$NR$^8$C(O)OC$_1$-C$_4$ alkyl,
(CH$_2$)$_n$(OCH$_2$CH$_2$)$_q$N(R$^8$)$_2$,
(CH$_2$)$_n$(OCH$_2$CH$_2$)$_q$NR$^8$C(O)C$_1$-C$_4$ alkyl,
(CH$_2$)$_n$(OCH$_2$CH$_2$)$_q$NR$^8$SO$_2$(C$_1$-C$_4$ alkyl),
(CH$_2$)$_n$[O]$_q$(C$_1$-C$_8$)alkylheterocyclic; and wherein for R n is 2-8 when R$^{12}$ is substituted on a carbon atom adjacent to a heteroatom;

R$^{13}$ is independently:
hydrogen,
C$_1$-C$_8$ alkyl,
(D)C$_3$-C$_7$ cycloalkyl,
(D)phenyl,
C(O)C$_1$-C$_8$ alkyl,
SO$_2$C$_1$-C$_8$ alkyl, or
SO$_2$-phenyl;

D is: a bond or C$_1$-C$_4$ alkyl;
g is: 0, 1, or 2;

y is: 1 or 2;
m is: 1-4;
n is: 0-8;
p is: 0-4; and
q is: 0-1; and wherein,
  aryl is defined as benzylic;
  heteroaryl is defined as a monocyclic or bicyclic aromatic ring of 5 to 10 carbon atoms containing from one to three heteroatoms selected from O, N, or S; and heterocyclic is defined as a monocyclic, bicyclic, or tricyclic ring of 5 to 14 carbon atoms which can be aromatic or nonaromatic and containing from one to three heteroatoms selected from N, O, or S.

Another aspect of the present invention relates to a method for treating obesity or diabetes mellitus in a patient which comprises administering to said patient an effective amount of a compound of formula I, or a pharmaceutical salt, solvate, enantiomer or prodrug thereof, wherein said compound is an agonist of the melanocortin-4 receptor.

Another aspect of the present invention relates to a method for treating male or female sexual dysfunction, including erectile dysfunction, which comprises administering to said male or female an effective amount of a compound of formula I, or a pharmaceutical salt thereof, wherein said compound is an agonist of the melanocortin-4 receptor.

In addition, the present invention relates to a use of a compound of formula I in treating obesity or diabetes.

The present invention also relates to the use of a compound of formula I in treating male or female sexual dysfunction, including erectile dysfunction wherein said compound is an agonist of the melanocortin-4 receptor.

The present invention relates to the use of a compound of formula I:

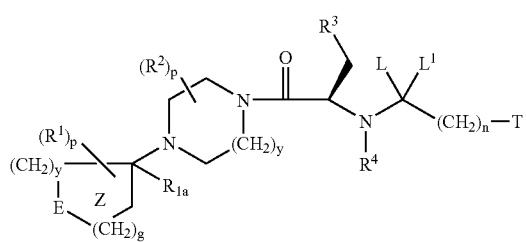

(I)

or a pharmaceutically acceptable salt, solvate or stereoisomer thereof, wherein wherein:
L and $L^1$ are both hydrogen or combine together to form an oxo group;
E is: O, S, $NR^{1B}$, SO, $SO_2$, $CR^9$, or $C(R^9)_2$, provided that when E is $CR^9$, or $C(R^9)_2$, may combine with an adjacent $R^1$ to form a 5, 6, or 7-member saturated or unsaturated carbocycle;
  wherein the Z ring has 0, or 1 double bond;
$R^1$ is selected from the group consisting of:
  hydrogen,
  $C_1$-$C_8$ alkyl,
  $C_2$-$C_8$ alkenyl,
  $C_2$-$C_4$ haloalkyl
  (D)$C_3$-$C_7$ cycloalkyl,
  (D)phenyl,
  aryl,
  C(O)O$C_1$-$C_8$ alkyl, wherein phenyl, aryl, alkenyl, and cycloalkyl groups are optionally substituted with hydroxy, halo, $C_1$-$C_8$ alkyl, $C_1$-$C_4$ alkoxy, $C_2$-$C_4$ haloalkyl, and (D)$C_3$-$C_7$ cycloalkyl provided that the halo, hydroxy are not substituted on a carbon atom adjacent to a heteroatom.
$R_{1a}$ is: hydrogen,
  $C_1$-$C_8$ alkyl,
  (D)$C_3$-$C_7$ cycloalkyl,
  (D)phenyl,
  (D)aryl,
  (D)heteroaryl;
  (D)C(O)$C_1$-$C_4$ alkyl,
  (D)C(O)O$C_1$-$C_4$ alkyl,
  $(CH_2)_m N(R^8)_2$,
  $(CH_2)_m NR^8 C(O)C_1$-$C_4$ alkyl,
  $(CH_2)_m NR^8 SO_2(C_1$-$C_4$ alkyl),
  $(CH_2)_m OR^8$,
  $(CH_2)_m SC_1$-$C_4$ alkyl,
  $(CH_2)_m SO(C_1$-$C_4$ alkyl),
  $(CH_2)_m SO_2(C_1$-$C_4$ alkyl), or
  $(CH_2)_m SO_2 N(R^8)_2$;
  wherein $C_1$-$C_8$ alkyl, $C_3$-$C_7$ cycloalkyl, phenyl, aryl and heteroaryl are optionally substituted with one to five substituents independently selected from the group consisting of perfluoro$C_1$-$C_4$ alkoxy, halo, hydroxy, $C_1$-$C_8$ alkyl, $C_1$-$C_4$ alkoxy, and $C_1$-$C_4$ haloalkyl; provided that halo and hydroxy groups are not substituted on a carbon atom adjacent to a heteroatom;
$R^{1b}$ is: hydrogen,
  $C_1$-$C_8$ alkyl,
  (D)$C_3$-$C_7$ cycloalkyl,
  $SO_2(C_1$-$C_8$ alkyl),
  (D)C(O)$C_1$-$C_4$ alkyl,
  (D)C(O)O$C_1$-$C_4$ alkyl,
  (D)CON$(R^8)_2$, or
  $SO_2$(D)phenyl, wherein the phenyl group is optionally substituted with one to five substituent selected from halo, and $C_1$-$C_8$ alkyl;
$R^2$ is: hydrogen,
  $C_1$-$C_8$ alkyl,
  CONH$C_1$-$C_4$ alkyl,
  (D)phenyl,
  oxo, or
  (D)$C_3$-$C_7$ cycloalkyl,
  provided that when $R^2$ is oxo, $R^2$ is on one of the ring carbon atoms adjacent to the nitrogen atom bearing the Z ring;
$R^3$ is: phenyl, aryl or thienyl;
  wherein phenyl, aryl and thienyl are optionally substituted with one to three substituents independently selected from the group consisting of:
  cyano, perfluoro$C_1$-$C_4$ alkoxy, halo, $C_1$-$C_8$ alkyl, (D)$C_3$-$C_7$ cycloalkyl, $C_1$-$C_4$ alkoxy, $C_1$-$C_4$ haloalkyl;
$R^4$ is: hydrogen,
  $C_1$-$C_8$ alkyl,
  $CH_2(CH_2)_m C_1$-$C_4$ alkoxy,
  C(O)$C_1$-$C_4$ alkyl, or
  C(O)O$C_1$-$C_4$ alkyl;
R is: hydroxy,
  halo,
  $C_1$-$C_8$ alkyl,
  $C_2$-$C_8$ alkenyl,
  $C_1$-$C_8$ alkoxy,
  $C_1$-$C_4$ haloalkyl,
  (D)$C_3$-$C_7$ cycloalkyl,
  (D)aryl,
  (D)heteroaryl;

(D)C(O)C$_1$-C$_4$ alkyl,
(D)C(O)OC$_1$-C$_4$ alkyl,
(D)C(O)heteroaryl,
(D)N(R$^8$)$_2$,
(D)NR$^8$C(O)C$_1$-C$_4$ alkyl,
(D)NR$^8$SO$_2$(C$_1$-C$_4$ alkyl),
(D)OC$_1$-C$_4$ alkyl,
(D)OC(O)C$_1$-C$_4$ alkyl,
(D)heterocyclic,
(D)SC$_1$-C$_4$ alkyl, or
(D)SO$_2$N(R$^8$)$_2$;
wherein C$_1$-C$_8$ alkyl, C$_1$-C$_8$ alkoxy, C$_3$-C$_7$ cycloalkyl, phenyl, aryl, heterocyclic, and heteroaryl are optionally substituted with one to five substituents independently selected from R$^8$; and provided that when R is halo or hydroxy it is not substituted on a carbon adjacent to a heteroatom;

each R$^8$ is independently:
hydrogen,
oxo,
C$_1$-C$_8$ alkyl,
(D)C$_3$-C$_7$ cycloalkyl,
phenyl,
aryl or
heteroaryl,
wherein C$_1$-C$_8$ alkyl, C$_3$-C$_7$ cycloalkyl, phenyl, aryl and heteroaryl are optionally substituted with one to three substituents selected from the group consisting of C$_1$-C$_8$ alkyl, halo, and hydroxy; provided that the halo and hydroxy groups are not substituted on a carbon adjacent to a heteroatom;

T is:

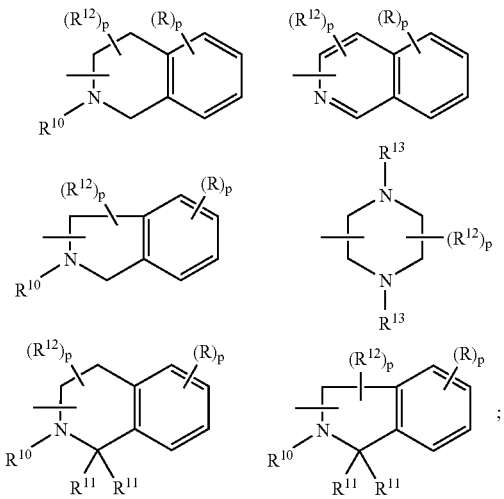

R$^9$ is independently:
hydrogen,
(C$_1$-C$_8$)alkyl,
C$_2$-C$_8$ alkenyl,
C(O)C$_1$-C$_8$ alkyl,
C$_2$-C$_8$ alkynyl,
phenyl,
aryl, or
heteroaryl;
R$^{10}$ is; hydrogen,
(C$_1$-C$_8$)alkyl,
C$_3$-C$_8$ alkenyl,
C(O)C$_1$-C$_8$ alkyl,
C$_2$-C$_8$ alkynyl,
phenyl,
aryl, or
heteroaryl;
R$^{11}$ is independently:
hydrogen, (C$_1$-C$_8$)alkyl, or (D)phenyl, or aryl;
R$^{12}$ is independently:
C$_1$-C$_8$ alkyl,
phenyl,
aryl,
heteroaryl,
(CH$_2$)$_n$N(R$^8$)$_2$,
(CH$_2$)$_n$NR$^8$C(O)C$_1$-C$_4$ alkyl,
(CH$_2$)$_n$NR$^8$C(O)OC$_1$-C$_4$ alkyl,
(CH$_2$)$_n$(OCH$_2$CH$_2$)$_q$N(R$^8$)$_2$,
(CH$_2$)$_n$(OCH$_2$CH$_2$)$_q$NR$^8$C(O)C$_1$-C$_4$ alkyl,
(CH$_2$)$_n$(OCH$_2$CH$_2$)$_q$NR$^8$SO$_2$(C$_1$-C$_4$ alkyl), or
(CH$_2$)$_n$[O]$_q$(C$_1$-C$_8$)alkylheterocyclic; and wherein for R$^{12}$, n is 2-8 when R$^{12}$ substituted on a carbon atom adjacent to a heteroatom;

R$^{13}$ is independently:
hydrogen,
C$_1$-C$_8$ alkyl,
(D)C$_3$-C$_7$ cycloalkyl,
(D)phenyl,
C(O)C$_1$-C$_8$ alkyl,
SO$_2$C$_1$-C$_8$ alkyl, or
SO$_2$-phenyl;
D is: a bond or C$_1$-C$_4$ alkyl;
g is: 0, 1, or 2;
y is: 1 or 2;
m is: 1-4;
n is: 0-8;
p is: 0-4; and
q is: 0-1; in the manufacture of a medicament for treating obesity and/or diabetes.

In addition, the present invention relates to a compound of formula I for use in treating obesity and/or diabetes in companion animals i.e. dogs, cats and the like wherein said compound is an agonist of the melanocortin-4 receptor.

Yet another aspect of the present invention relates to a pharmaceutical composition comprising a compound of formula I or a pharmaceutically acceptable salt thereof, and a pharmaceutical carrier.

The present invention also provides a process for preparing a compound of formula I:

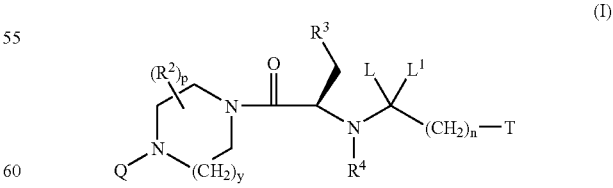

(I)

or a pharmaceutically acceptable salt or stereoisomer thereof, wherein:
—CLL'-(CH$_2$)$_n$-T is:

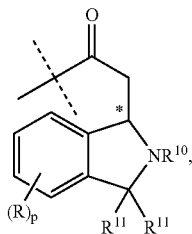

wherein $R^{10}$ is a CBz or Boc protecting group, hydrogen, $(C_1-C_8)$alkyl, $C_3-C_8$ alkenyl, $C(O)C_1-C_8$ alkyl, $C_2-C_8$ alkynyl, phenyl, aryl, or heteroaryl;

Q represents the moiety:

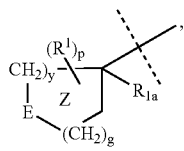

wherein L and $L^1$ are both hydrogen or combine together to form an oxo group;

E is: O, S, $NR^{1b}$, SO, $SO_2$, $CR^9$, or $C(R^9)_2$, provided that when E is $CR^9$, or $C(R^9)_2$, $R^9$ may combine with an adjacent $R^1$ to form a 5, 6, or 7-member saturated or unsaturated carbocycle;

wherein the Z ring has 0, or 1 double bond;

$R^1$ is selected from the group consisting of:
hydrogen,
$C_1-C_8$ alkyl,
$C_2-C_8$ alkenyl,
$C_2-C_4$ haloalkyl
(D)$C_3-C_7$ cycloalkyl,
(D)phenyl,
aryl,
$C(O)OC_1-C_8$ alkyl,
wherein phenyl, aryl, alkenyl, and cycloalkyl groups are optionally substituted with hydroxy, halo, $C_1-C_8$ alkyl, $C_1-C_4$ alkoxy, $C_2-C_4$ haloalkyl, and (D)$C_3-C_7$ cycloalkyl provided that the halo, hydroxy are not substituted on a carbon atom adjacent to a heteroatom.

$R_{1a}$ is: hydrogen,
$C_1-C_8$ alkyl,
(D)$C_3-C_7$ cycloalkyl,
(D)phenyl,
(D)aryl,
(D)heteroaryl;
(D)C(O)$C_1-C_4$ alkyl,
(D)C(O)O$C_1-C_4$ alkyl,
$(CH_2)_mN(R^8)_2$,
$(CH_2)_mNR^8C(O)C_1-C_4$ alkyl,
$(CH_2)_mNR^8SO_2(C_1-C_4$ alkyl),
$(CH_2)_mOR^8$,
$(CH_2)_mSC_1-C_4$ alkyl,
$(CH_2)_mSO(C_1-C_4$ alkyl),
$(CH_2)_mSO_2(C_1-C_4$ alkyl), or
$(CH_2)_mSO_2N(R^8)_2$;
wherein $C_1-C_8$ alkyl, $C_3-C_7$ cycloalkyl, phenyl, aryl and heteroaryl are optionally substituted with one to five substituents independently selected from perfluoro$C_1$-$C_4$ alkoxy, halo, hydroxy, $C_1-C_8$ alkyl, $C_1-C_4$ alkoxy, and $C_1-C_4$ haloalkyl; provided that halo and hydroxy groups are not substituted on a carbon atom adjacent to a heteroatom;

$R^{1b}$ is: hydrogen,
$C_1-C_8$ alkyl,
(D)$C_3-C_7$ cycloalkyl,
$SO_2(C_1-C_8$ alkyl),
(D)C(O)$C_1-C_4$ alkyl,
(D)C(O)O$C_1-C_4$ alkyl,
(D)CON$(R^8)_2$, or
$SO_2$(D)phenyl wherein the phenyl group is optionally substituted with one to five substituent selected from halo, and $C_1-C_8$ alkyl;

$R^2$ is: hydrogen,
$C_1-C_8$ alkyl,
CONH$C_1-C_4$ alkyl,
(D)phenyl,
oxo, or
(D)$C_3-C_7$ cycloalkyl, provided that when $R^2$ is oxo, $R^2$ is on one of the ring carbon atoms adjacent to the nitrogen atom bearing the Z ring;

$R^3$ is: phenyl, aryl or thienyl;
wherein phenyl, aryl and thienyl are optionally substituted with one to three substituents independently selected from the group consisting of:
cyano, perfluoro$C_1-C_4$ alkoxy, halo, $C_1-C_8$ alkyl, (D)$C_3$-$C_7$ cycloalkyl, $C_1-C_4$ alkoxy, $C_1-C_4$ haloalkyl;

$R^4$ is: hydrogen,
$C_1-C_8$ alkyl,
$CH_2(CH_2)_mC_1-C_4$ alkoxy,
$C(O)C_1-C_4$ alkyl, or $C(O)OC_1-C_4$ alkyl;

R is: hydroxy,
halo,
$C_1-C_8$ alkyl,
$C_2-C_8$ alkenyl,
$C_1-C_8$ alkoxy,
$C_1-C_4$ haloalkyl,
(D)$C_3-C_7$ cycloalkyl,
(D)aryl,
(D)heteroaryl;
(D)C(O)$C_1-C_4$ alkyl,
(D)C(O)O$C_1-C_4$ alkyl,
(D)C(O)heteroaryl,
(D)N$(R^8)_2$,
(D)NR$^8$C(O)$C_1-C_4$ alkyl,
(D)NR$^8$SO$_2(C_1-C_4$ alkyl),
(D)O$C_1-C_4$ alkyl,
(D)OC(O)$C_1-C_4$ alkyl,
(D)heterocyclic,
(D)S$C_1-C_4$ alkyl, or
(D)SO$_2$N$(R^8)_2$;
wherein $C_1-C_8$ alkyl, $C_1-C_8$ alkoxy, $C_3-C_7$ cycloalkyl, phenyl, aryl, heterocyclic, and heteroaryl are optionally substituted with one to five substituents independently selected from $R^8$; and provided that when R is halo or hydroxy it is not substituted on a carbon adjacent to a heteroatom;

each $R^8$ is independently:
hydrogen,
oxo,
$C_1-C_8$ alkyl,
(D)$C_3-C_7$ cycloalkyl,
phenyl,
aryl or
heteroaryl, wherein $C_1$-$C_8$ alkyl, $C_3$-$C_7$ cycloalkyl, phenyl, aryl and heteroaryl are optionally substituted with one to three substituents selected from the group consisting of $C_1$-$C_8$ alkyl, halo, and hydroxy; provided that the halo and hydroxy groups are not substituted on a carbon adjacent to a heteroatom;

$R^9$ is independently:
  hydrogen,
  $(C_1$-$C_8)$alkyl,
  $C_2$-$C_8$ alkenyl,
  $C(O)C_1$-$C_8$ alkyl,
  $C_2$-$C_8$ alkynyl,
  phenyl,
  aryl, or
  heteroaryl;

$R^{11}$ is independently:
  hydrogen, $(C_1$-$C_8)$alkyl, or (D)phenyl, or aryl;

D is: a bond or $C_1$-$C_4$ alkyl;
g is: 0, 1, or 2;
y is: 1 or 2;
m is: 1-4;
n is: 0-8;
p is: 0-4; and
q is: 0-1;

comprising the steps of:

a) reacting a compound having a structural formula 1:

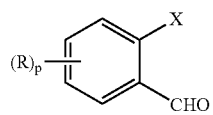

(1)

with $CH_2CH{=}C(O)OR^a$ wherein $R^a$ is hydrogen or $C_1$-$C_8$ alkyl and X is halo, in the presence of a catalyst and a base in a suitable organic solvent to give the compound of formula 2:

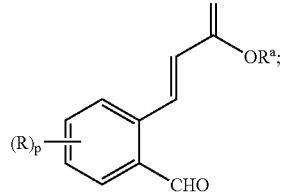

(2)

b) reductively aminating the compound of formula 2 in the presence of amine to give a compound of formula 3:

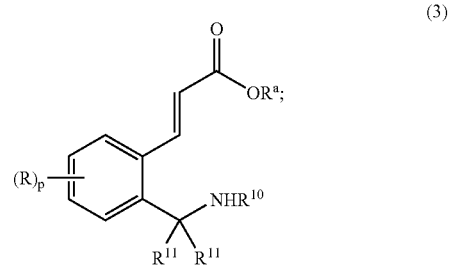

(3)

c) cyclizing the compound of formula 3 by Michael addition to give a compound of formula 4 or stereoisomers thereof:

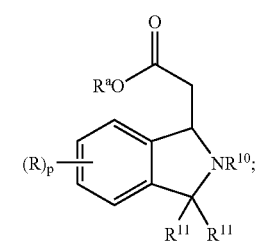

(4)

d) coupling the compound of formula 4 or stereoisomers thereof wherein $R^a$ is H, with a compound of formula 5:

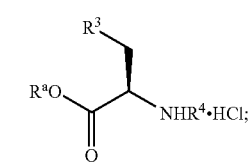

(5)

wherein $R^a$ is $C_1$-$C_8$ alkyl, to give a compound of formula 6:

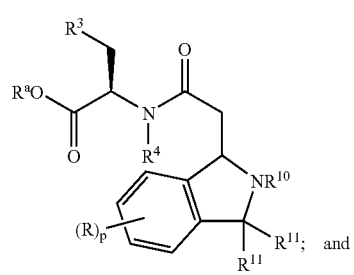

(6)

e) coupling the compound of formula 6 wherein $R^a$ is H, with a compound having a structural formula:

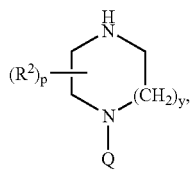

to afford the compound of formula 1.

The present invention also provides a process for preparing a compound of formula I:

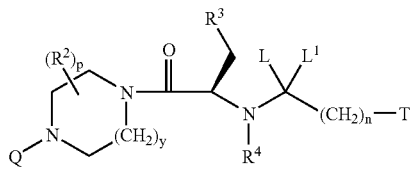

or a pharmaceutically acceptable salt or stereoisomer thereof, wherein:

-LL'(CH$_2$)$_n$-T is represented by the group:

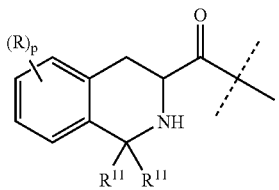

Q represents the moiety:

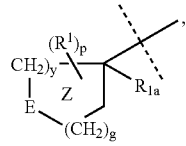

E is: O, S, NR$^{1b}$, SO, SO$_2$, CR$^9$, or C(R$^9$)$_2$, provided that when E is CR$^9$, or C(R$^9$)$_2$, R$^9$ may combine with an adjacent R$^1$ to form a 5, 6, or 7-member saturated or unsaturated carbocycle;

wherein the Z ring has 0, or 1 double bond;

R$^1$ is selected from the group consisting of:
hydrogen,
C$_1$-C$_8$ alkyl,
C$_2$-C$_8$ alkenyl,
C$_2$-C$_4$ haloalkyl
(D)C$_3$-C$_7$ cycloalkyl,
(D)phenyl,
aryl,
C(O)OC$_1$-C$_8$ alkyl,
wherein phenyl, aryl, alkenyl, and cycloalkyl groups are optionally substituted with hydroxy, halo, C$_1$-C$_8$ alkyl, C$_1$-C$_4$ alkoxy, C$_2$-C$_4$ haloalkyl, and (D)C$_3$-C$_7$ cycloalkyl provided that the halo, hydroxy are not substituted on a carbon atom adjacent to a heteroatom;

R$_{1a}$ is: hydrogen,
C$_1$-C$_8$ alkyl,
(D)C$_3$-C$_7$ cycloalkyl,
(D)phenyl,
(D)aryl,
(D)heteroaryl;
(D)C(O)C$_1$-C$_4$ alkyl,
(D)C(O)OC$_1$-C$_4$ alkyl,
(CH$_2$)$_m$N(R$^8$)$_2$,
(CH$_2$)$_m$NR$^8$C(O)C$_1$-C$_4$ alkyl,
(CH$_2$)$_m$NR$^8$SO$_2$(C$_1$-C$_4$ alkyl),
(CH$_2$)$_m$OR$^8$,
(CH$_2$)$_m$SC$_1$-C$_4$ alkyl,
(CH$_2$)$_n$SO(C$_1$-C$_4$ alkyl),
(CH$_2$)$_m$SO$_2$(C$_1$-C$_4$ alkyl), or
(CH$_2$)$_m$SO$_2$N(R$^8$)$_2$;
wherein C$_1$-C$_8$ alkyl, C$_3$-C$_7$ cycloalkyl, phenyl, aryl and heteroaryl are optionally substituted with one to five substituents independently selected from the group consisting of perfluoroC$_1$-C$_4$ alkoxy, halo, hydroxy, C$_1$-C$_8$ alkyl, C$_1$-C$_4$ alkoxy, and C$_1$-C$_4$ haloalkyl; provided that halo and hydroxy groups are not substituted on a carbon atom adjacent to a heteroatom;

R$^{1b}$ is: hydrogen,
C$_1$-C$_8$ alkyl,
(D)C$_3$-C$_7$ cycloalkyl,
SO$_2$(C$_1$-C$_8$ alkyl),
(D)C(O)C$_1$-C$_4$ alkyl,
(D)C(O)OC$_1$-C$_4$ alkyl,
(D)CON(R$^8$)$_2$, or
SO$_2$(D)phenyl wherein the phenyl group is optionally substituted with one to 1 to 5 substituent selected from halo, and C$_1$-C$_8$ alkyl;

R$^2$ is: hydrogen,
C$_1$-C$_8$ alkyl,
CONHC$_1$-C$_4$ alkyl,
(D)phenyl,
oxo, or
(D)C$_3$-C$_7$ cycloalkyl, provided that when R$^2$ is oxo, R$^2$ is on one of the ring carbon atoms adjacent to the nitrogen atom bearing the Z ring;

R$^3$ is: phenyl, aryl or thienyl;
wherein phenyl, aryl and thienyl are optionally substituted with one to three substituents independently selected from the group consisting of:
cyano, perfluoroC$_1$-C$_4$ alkoxy, halo, C$_1$-C$_8$ alkyl, (D)C$_3$-C$_7$ cycloalkyl, C$_1$-C$_4$ alkoxy, C$_1$-C$_4$ haloalkyl;

R$^4$ is: hydrogen,
C$_1$-C$_8$ alkyl,
CH$_2$(CH$_2$)$_m$C$_1$-C$_4$ alkoxy,
C(O)C$_1$-C$_4$ alkyl or
C(O)OC$_1$-C$_4$ alkyl;

R is: hydroxy,
halo,
C$_1$-C$_8$ alkyl,
C$_2$-C$_8$ alkenyl,
C$_1$-C$_8$ alkoxy,
C$_1$-C$_4$ haloalkyl,
(D)C$_3$-C$_7$ cycloalkyl,
(D)aryl,
(D)heteroaryl;
(D)C(O)C$_1$-C$_4$ alkyl,
(D)C(O)OC$_1$-C$_4$ alkyl,
(D)C(O)heteroaryl,
(D)N(R$^8$)$_2$, (D)NR$^8$C(O)C$_1$-C$_4$ alkyl,
(D)NR$^8$SO$_2$(C$_1$-C$_4$ alkyl),
(D)OC$_1$-C$_4$ alkyl,
(D)OC(O)C$_1$-C$_4$ alkyl,
(D)heterocyclic,
(D)SC$_1$-C$_4$ alkyl, or
(D)SO$_2$N(R$^8$)$_2$;
wherein C$_1$-C$_8$ alkyl, C$_1$-C$_8$ alkoxy, C$_3$-C$_7$ cycloalkyl, phenyl, aryl, heterocyclic, and heteroaryl are optionally substituted with one to five substituents independently selected from R$^8$; and provided that when R is halo or hydroxy it is not substituted on a carbon adjacent to a heteroatom;

each R$^8$ is independently:
hydrogen,
oxo,
C$_1$-C$_8$ alkyl,
(D)C$_3$-C$_7$ cycloalkyl,
phenyl,
aryl or
heteroaryl,
wherein C$_1$-C$_8$ alkyl, C$_3$-C$_7$ cycloalkyl, phenyl, aryl and heteroaryl are optionally substituted with one to three substituents selected from the group consisting of C$_1$-C$_8$ alkyl, halo, and hydroxy; provided that the halo and hydroxy groups are not substituted on a carbon adjacent to a heteroatom;

R$^9$ is independently:
hydrogen,
(C$_1$-C$_8$)alkyl,
C$_2$-C$_8$ alkenyl,
C(O)C$_1$-C$_8$ alkyl,
C$_2$-C$_8$ alkynyl,
phenyl,
aryl, or
heteroaryl;

R$^{10}$ is: hydrogen,
(C$_1$-C$_8$)alkyl,
C$_3$-C$_8$ alkenyl,
C(O)C$_1$-C$_8$ alkyl,
C$_2$-C$_8$ alkynyl,
phenyl,
aryl, or
heteroaryl;

R$^{11}$ is independently:
hydrogen, (C$_1$-C$_8$)alkyl, or (D)phenyl, or aryl;
D is: a bond or C$_1$-C$_4$ alkyl;
g is: 0, 1, or 2;
y is: 1 or 2;
m is: 14;
n is: 0-8;
p is: 0-4; and
q is: 0-1;

comprising the steps of:
a) esterifying a compound of formula 1 with an alcohol R$^a$OH

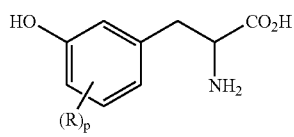

(1)

to form a compound of formula 2:

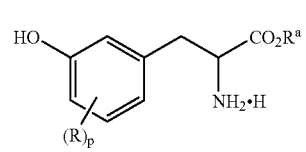

(2)

wherein R$^a$ is a group selected from C$_1$-C$_4$ alkyl, and (D)phenyl;
b) reacting a compound of formula 2 with R$^{11}$COR$^{11}$ to form a compound of formula:

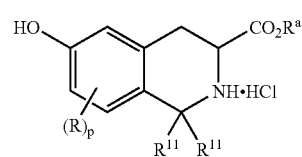

(3)

wherein R$^{11}$ is independently hydrogen, C$_1$-C$_4$ alkyl;
c) reacting a compound of formula 3 with an activating group to form a compound of formula 4:

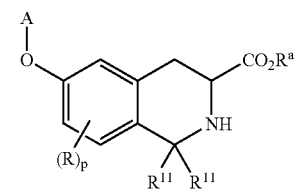

(4)

wherein A is an activating group;
d) deoxygenating the compound of formula 4 by hydrogenation to afford a compound of formula 5:

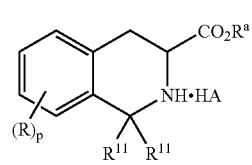

(5)

e) optionally reacting the compound of formula 5 wherein HA is an acidic, with an inorganic base to form a compound of formula 6:

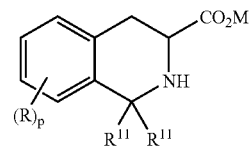

(6)

wherein M is a univalent cation;
f) resolving the compound of formula 5 or the compound of formula 6 wherein M is hydrogen to afford a chiral compound of formula 7:

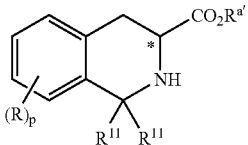

(7)

wherein Ra' is H or $R^a$;

g) coupling the compound of formula 7 with a compound of formula 8:

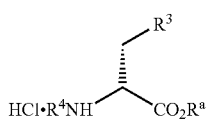

(8)

to afford a compound of formula 9:

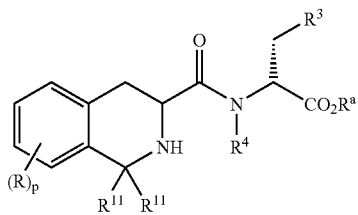

(9)

h) coupling the compound of formula 9 with a compound of formula 10:

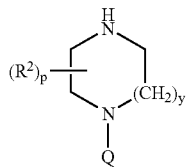

(10)

to afford a compound of formula I:

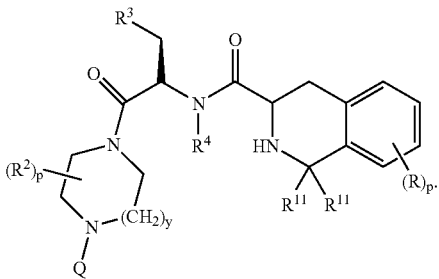

I

DETAILED DESCRIPTION OF THE INVENTION

Throughout the instant application, the following terms have the indicated meanings:

The term "$C_1$-$C_8$ alkyl" refers to a straight or branched saturated hydrocarbon moiety containing from 1 to 8 carbon atoms. The term "$C_1$-$C_4$ alkyl" refers specifically to methyl, ethyl, n-propyl, isopropyl, n-butyl, isobutyl, sec-butyl and t-butyl. A "$C_1$-$C_8$ haloalkyl" is a $C_1$-$C_8$ alkyl moiety that is substituted with one or more halo atoms. One example of a haloalkyl group is trifluoromethyl. A "$C_1$-$C_8$ alkoxy" group is a $C_1$-$C_8$ alkyl group attached through an oxygen linker i.e. —$OCH_3$.

The term "benzofused bicyclic" as used herein refers to a bicyclic ring system or radical wherein one of the rings is the benzene ring and wherein the point of attachment to the backbone of the compound the invention is at other than the benzene ring. Unless otherwise specified it is to be understood that each ring of the benzofused bicyclcic is optionally substituted with 1 to 3 substituents selected from alkyl, alkenyl, alkynyl, halo, haloalkyl, cyano, alkoxy, alkoxyalkyl, amino, substituted amino, thiol, formyl, carboxy alkyl, carboxyester, carbxamide, and sulfonamido groups.

The term "$C_3$-$C_7$ cycloalkyl" refers to cyclopropyl, cyclobutyl, cyclopentyl, cyclohexyl and cycloheptyl.

The term "hydrocarbon diradical" refers to a straight or branched chain of carbon atoms that may optionally be unsaturated at two or more carbons. Thus, a hydrocarbon diradical according to the present invention includes alkylene, alkenylene and alkylidene moieties. Examples include but are not intended to be limited to methylene, ethylene, propylene, butylene, —$CH(CH_3)CH(CH_3)$—, —$CH_2C(CH_3)_2$—, —$CH_2CH(CH_3)CH_2$—, —$CH=CHCH_2$—, —$CH=CH$—, —$CH_2C≡CCH_2$—, and the like.

The term "halo" refers to fluoro, chloro, bromo and iodo.

The term "perfluoro$C_1$-$C_4$ alkoxy" as used herein refers to $C_1$-$C_4$ alkoxy groups having from 1 to 5 fluorine atoms, and includes, for example, trifluoromethoxy and pentafluoroethoxy.

The term haloalkyl refers to a group having at least one carbon atom and as many halogen atoms as chemically sensible with or without hydrogen atoms, and positional isomers thereof. The term haloalkyl, therefore, includes but is not limited to groups such as trifluoromethytl, methylchloride, dichloromethyl, pentylchloride, butyl chloride, isopropyl chloride and the like.

As used herein a line "_____" attached to a structure, partial structure of a molecule or fragment thereof, without a group attached at the end represents a point of attachment to another molecule, fragment or radical unless otherwise indicated. For example, the group:

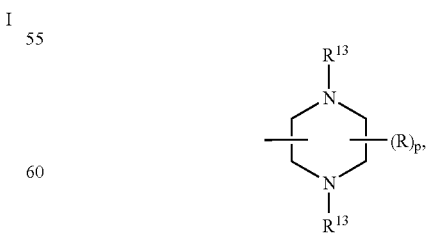

shows the piperazine groups as being attachable to another molecule or fragment at any position of the piperazine ring where the valency allows i.e. the carbon atoms.

Unless otherwise specified, a "heterocycle" or "heterocyclic" or "heterocyclyl" group is a 5, 6 or 7 membered saturated, or partially unsaturated, or aromatic mono-cyclic or benzofused bicyclic ring containing 1-5 heteroatoms selected from N, S or O, wherein said heterocycle is optionally substituted 1-4 times with:
$C_1$-$C_8$ alkyl, $C_1$-$C_4$ haloalkyl, (D)($C_3$-$C_7$ cycloalkyl), unsubstituted-mono-cyclic nitrogen containing heterocycle, (D)$NR^8R^8$, (D)$NR^8C(O)C_1$-$C_8$ alkyl, (D)$NR^8SO_2(C_1$-$C_8$ alkyl), (D)$SO(C_1$-$C_8$ alkyl), $(CH_2)_mSO_2R^8$, $(CH_2)_m$ $SO^2NR^8R^8$ or (D)phenyl wherein:

$R^8$ is as described herein; or when two $R^8$ groups are attached to the same nitrogen atom, said $R^8$ groups, together with the nitrogen to which they are attached, may combine to form a nitrogen containing heterocycle.

The variable "D" at each occurrence is independently a bond or a $C_1$-$C_4$ hydrocarbon diradical.

Unless otherwise specified, a "nitrogen containing heterocycle" is a heterocycle that contains 1-4 nitrogen atoms and optionally contains 1 other heteroatom selected from O or S. Examples of nitrogen containing heterocylces includes but is not limited to 1,1-dioxo-1$\lambda^6$-isothiazolidin-2-yl, pyrrole, thiazole, oxazolyl, imidazolyl, imidazolidinyl, 1,2,3-oxadiazolyl, piperidynyl, piperazinyl, pyrazinyl, pyrimidinyl, 1,3,5-triazinyl, morpholinyl, thiomorpholinyl, pyridazinyl, 1,3-4 thiadiazolyl, isothiazolyl, each optionally substituted with 1 to 3 substituents including for example halo, oxo, carboxy esters, carboxyamides, $C_1$-$C_8$ alkyl.

The term "oxo" as used herein refers to an oxygen atom formed by the combination of single bonds resulting in a double bond to oxygen. For example an "oxo" group formed by geminal substituents on a carbon atom depicts a carbonyl group i.e., an oxo group bonded to carbon.

The term "composition", as in pharmaceutical composition, is intended to encompass a product comprising the active ingredient(s), and the inert ingredient(s) that make up the carrier. Accordingly, the pharmaceutical compositions of the present invention encompass any composition made by admixing a compound of the present invention and a pharmaceutically acceptable carrier.

The term "pharmaceutical" when used herein as an adjective means substantially non-deleterious to the recipient patient.

The term "unit dosage form" refers to physically discrete units suitable as unitary dosages for human subjects and other non-human animals, each unit containing a predetermined quantity of active material calculated to produce the desired therapeutic effect, in association with a suitable pharmaceutical carrier.

The terms "treating" and "treat", as used herein, include their generally accepted meanings, i.e., preventing, prohibiting, restraining, alleviating, ameliorating, slowing, stopping, or reversing the progression or severity of a pathological condition, or sequela thereof, described herein.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, and inability to achieve an orgasm. An increase in erectile dysfunction is often associated with age and is generally caused by a physical disease or as a side effect of drug treatment.

"Female sexual dysfunction" encompasses, without limitation, conditions such as a lack of sexual desire and related arousal disorders, inhibited orgasm, lubrication difficulties, and vaginismus.

Because certain compounds of the invention contain an acidic moiety (e.g., carboxy), the compound of formula I may exist as a pharmaceutical base addition salt thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like.

Because certain compounds of the invention contain a basic moiety (e.g., amino), the compound of formula I can also exist as a pharmaceutical acid addition salt. Such salts include sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4-dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, beta-hydroxybutyrate, glycollate, maleate, tartrate, methanesulfonate, propanesulfonate, naphthalene-1-sulfonate, naphthalene-2-sulfonate, mandelate and the like salts. Preferred acid addition salts include the hydrochloride.

It will be understood that, as used herein, references to the compounds of formula I are meant to also include the pharmaceutical salts.

Some of the compounds described herein may exist as tautomers such as keto-enol tautomers. The individual tautomers as well as mixtures thereof are encompassed within the scope of the present invention.

Another embodiment the present invention provides a process for preparing a compound of formula I:

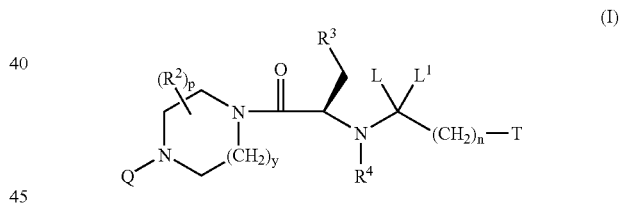

(I)

or a pharmaceutically acceptable salt or stereoisomer thereof, wherein:

-LL'$(CH_2)_n$-T is represented by the group:

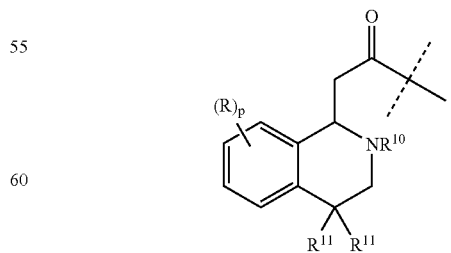

$R^{10}$ is a CBz or Boc protecting group, hydrogen, ($C_1$-$C_8$) alkyl, $C_3$-$C_8$ alkenyl, C(O)$C_1$-$C_8$ alkyl, $C_2$-$C_8$ alkynyl, phenyl, aryl, or heteroaryl;

Q represents the moiety:

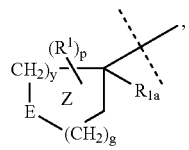

wherein E is O, S, $NR^{1b}$, SO, $SO_2$, $CR^9$, or $C(R^9)_2$, provided that when E is $CR^9$, or $C(R^9)_2$, $R^9$ may combine with an adjacent $R^1$ to form a 5, 6, or 7-member saturated or unsaturated carbocycle;
wherein the Z ring has 0, or 1 double bond;
$R^1$ is: hydrogen,
$C_1$-$C_8$ alkyl,
$C_2$-$C_8$ alkenyl,
$C_2$-$C_4$ haloalkyl
(D)$C_3$-$C_7$ cycloalkyl,
(D)phenyl,
aryl,
$C(O)OC_1$-$C_8$ alkyl,
wherein phenyl, aryl alkenyl, and cycloalkyl groups are optionally substituted with hydroxy, halo, $C_1$-$C_8$ alkyl, $C_1$-$C_4$ alkoxy, $C_2$-$C_4$ haloalkyl, and (D)$C_3$-$C_7$ cycloalkyl provided that the halo, hydroxy are not substituted on a carbon atom adjacent to a heteroatom;
$R_{1a}$ is: hydrogen,
$C_1$-$C_8$ alkyl,
(D)$C_3$-$C_7$ cycloalkyl,
(D)phenyl,
(D)aryl,
(D)heteroaryl;
(D)$C(O)C_1$-$C_4$ alkyl,
(D)$C(O)OC_1$-$C_4$ alkyl,
$(CH_2)_m N(R^8)_2$,
$(CH_2)_m NR^8 C(O)C_1$-$C_4$ alkyl,
$(CH_2)_m NR^8 SO_2(C_1$-$C_4$ alkyl),
$(CH_2)_m OR^8$,
$(CH_2)_m SC_1$-$C_4$ alkyl,
$(CH_2)_m SO(C_1$-$C_4$ alkyl),
$(CH_2)_m SO_2(C_1$-$C_4$ alkyl), or
$(CH_2)_m SO_2 N(R^8)_2$;
wherein $C_1$-$C_8$ alkyl, $C_3$-$C_7$ cycloalkyl, phenyl, aryl and heteroaryl are optionally substituted with one to five substituents independently selected from the group consisting of perfluoro$C_1$-$C_4$ alkoxy, halo, hydroxy, $C_1$-$C_8$ alkyl, $C_1$-$C_4$ alkoxy, and $C_1$-$C_4$ haloalkyl; provided that halo and hydroxy groups are not substituted on a carbon atom adjacent to a heteroatom;
$R^{1b}$ is: hydrogen,
$C_1$-$C_8$ alkyl,
(D)$C_3$-$C_7$ cycloalkyl,
$SO_2(C_1$-$C_8$ alkyl),
(D)$C(O)C_1$-$C_4$ alkyl,
(D)$C(O)OC_1$-$C_4$ alkyl,
(D)$CON(R^8)_2$, or
$SO_2$(D)phenyl wherein the phenyl group is optionally substituted with one to five substituent selected from halo, and $C_1$-$C_8$ alkyl;
$R^2$ is: hydrogen,
$C_1$-$C_8$ alkyl,
$CONHC_1$-$C_4$ alkyl,
(D)phenyl,
oxo, or
(D)$C_3$-$C_7$ cycloalkyl, provided that when $R^2$ is oxo, $R^2$ is on one of the ring carbon atoms adjacent to the nitrogen atom bearing the Z ring;
$R^3$ is: phenyl, aryl or thienyl;
wherein phenyl, aryl and thienyl are optionally substituted with one to three substituents independently selected from the group consisting of:
cyano, perfluoro$C_1$-$C_4$ alkoxy, halo, $C_1$-$C_8$ alkyl, (D)$C_3$-$C_7$ cycloalkyl, $C_1$-$C_4$ alkoxy, $C_1$-$C_4$ haloalkyl;
$R^4$ is: hydrogen,
$C_1$-$C_8$ alkyl,
$CH_2(CH_2)_m C_1$-$C_4$ alkoxy,
$C(O)C_1$-$C_4$ alkyl, or
$C(O)OC_1$-$C_4$ alkyl;
R is: hydroxy,
halo,
$C_1$-$C_8$ alkyl,
$C_2$-$C_8$ alkenyl,
$C_1$-$C_8$ alkoxy,
$C_1$-$C_4$ haloalkyl,
(D)$C_3$-$C_7$ cycloalkyl,
(D)aryl,
(D)heteroaryl;
(D)$C(O)C_1$-$C_4$ alkyl,
(D)$C(O)OC_1$-$C_4$ alkyl,
(D)$C(O)$heteroaryl,
(D)$N(R^8)_2$,
(D)$NR^8 C(O)C_1$-$C_4$ alkyl,
(D)$NR^8 SO_2(C_1$-$C_4$ alkyl),
(D)$OC_1$-$C_4$ alkyl,
(D)$OC(O)C_1$-$C_4$ alkyl,
(D)heterocyclic,
(D)$SC_1$-$C_4$ alkyl, or
(D)$SO_2 N(R^8)_2$;
wherein $C_1$-$C_8$ alkyl, $C_1$-$C_8$ alkoxy, $C_3$-$C_7$ cycloalkyl, phenyl, aryl, heterocyclic, and heteroaryl are optionally substituted with one to five substituents independently selected from $R^8$; and provided that when R is halo or hydroxy it is not substituted on a carbon adjacent to a heteroatom;
each $R^8$ is independently:
hydrogen,
oxo,
$C_1$-$C_8$ alkyl,
(D)$C_3$-$C_7$ cycloalkyl,
phenyl,
aryl or
heteroaryl,
wherein $C_1$-$C_8$ alkyl, $C_3$-$C_7$ cycloalkyl, phenyl, aryl and heteroaryl are optionally substituted with one to three substituents selected from the group consisting of $C_1$-$C_8$ alkyl, halo, and hydroxy; provided that the halo and hydroxy groups are not substituted on a carbon adjacent to a heteroatom;
$R^9$ is independently:
hydrogen,
$(C_1$-$C_8)$alkyl,
$C_2$-$C_8$ alkenyl,
$C(O)C_1$-$C_8$ alkyl,
$C_2$-$C_8$ alkynyl,
phenyl,
aryl, or
heteroaryl;
$R^{11}$ is independently:
hydrogen, $(C_1$-$C_8)$alkyl, or (D)phenyl, or aryl;
D is: a bond or $C_1$-$C_4$ alkyl;
g is: 0, 1, or 2;

y is: 1 or 2;
m is: 1-4;
n is: 0-8;
p is: 0-4; and
q is: 0-1;

comprising the steps of:

a) reacting a compound formula 1:

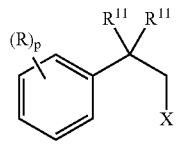
(1)

wherein X is halo and $R^{11}$ is independently, hydrogen or $C_1$-$C_4$ alkyl, with $CNCH_2CO_2R^a$ wherein $R^a$ is $C_1$-$C_8$ alkyl, or benzyl to afford a compound of formula 2:

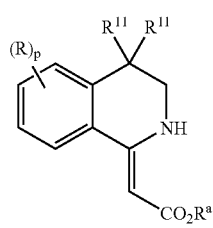
(2)

b) protecting the compound of formula 2 to form the compound of formula 3:

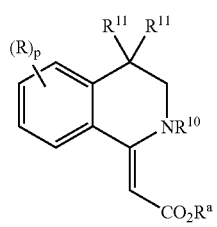
(3)

c) hydrogenating the compound of formula 3 to afford a compound of formula 4:

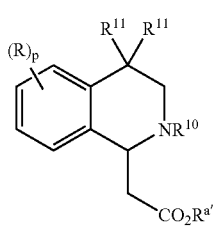
(4)

d) coupling the compound of formula 4 wherein $R^{a'}$ is hydrogen with a compound of formula 5:

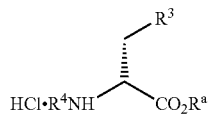
(5)

to afford a compound of formula 6:

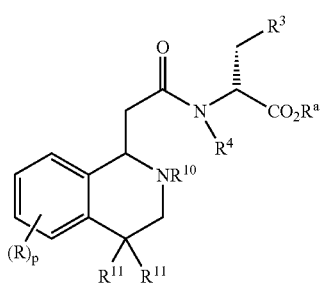
(6)

e) coupling the compound of formula 6 with a compound of formula 7:

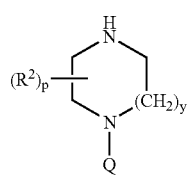
(7)

to afford a compound of formula I:

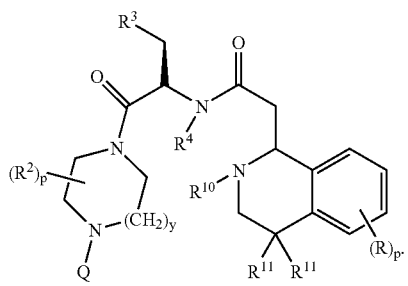
I

When describing various aspects of the present compounds, the terms "A domain" or "A" piece, "B domain" or "B" piece and "C domain" or "C" pieces are used below. This domain concept is illustrated below:

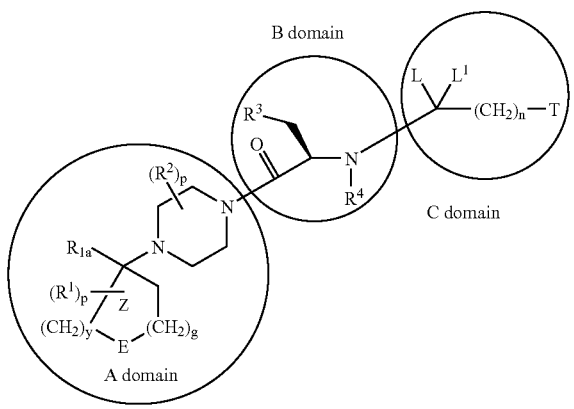

Utility

Compounds of formula I are effective as melanocortin receptor agonists, particularly as agonists of the human MC-4 receptor. As melanocortin receptor agonists, the compounds of formula I are useful in the treatment of diseases, disorders or conditions responsive to the activation of one or more of the melanocortin receptors including, but not limited to, MC-1, MC-2, MC-3, MC-4, or MC-5. Diseases, disorders or conditions receptive to treatment with a MC-4 agonist include those mentioned supra and those described in WO 00/74679, the teachings of which are herein incorporated by reference.

Preferred Compounds of the Invention

The following listing sets out several groups of preferred compounds organized by domains. It will be understood that each of the listings may be combined with other listings to create additional groups of preferred compounds.

A Domains

A preferred compound of formula I is one having A-domain as listed below:

a) for the Z ring y is 1
b) for the Z ring y is 2
c) for the Z ring g is 1 or 2
d) $R_{1a}$ is:
  $C_1$-$C_8$ alkyl,
  (D)$C_3$-$C_7$ cycloalkyl,
  (D)phenyl,
  (D)aryl,
  (D)heteroaryl,
  $(CH_2)_m N(R^8)_2$,
  $(CH_2)_m NR^8 C(O)C_1$-$C_4$ alkyl,
  $(CH_2)_n NR^8 C(O)OC_1$-$C_4$ alkyl,
  $(CH_2)_m NR^8 SO_2(C_1$-$C_4$ alkyl),
  wherein m is 1 or 2; and wherein $C_1$-$C_8$ alkyl, $C_1$-$C_8$ alkoxy, $C_3$-$C_7$ cycloalkyl, phenyl, aryl and heteroaryl are optionally substituted with one to five substituents independently selected from halo, hydroxy and $C_1$-$C_8$ alkyl $C_1$-$C_4$ haloalkyl; wherein the halo, and hydroxy goups are not substituted on a carbon atom adjacent 0 to a heteroatom; and wherein for the group or subgroup —N($R^8$)$_2$, each $R^8$ may combine with the other to form a nitrogen containing heterocylce;
E is $NR^{1b}$, S, O, SO, $SO_2$ wherein $R^{1b}$ is preferably hydrogen, $C_1$-$C_8$ alkyl, (D)C(O)O $C_1$-$C_4$ alkyl, (D)CO $C_1$-$C_4$ alkyl, or (D)CON($R^8$)$_2$;

E is O, $NR^{1b}$, $SO_2$, or S wherein $R^{1b}$ is $C_1$-$C_4$ alkyl;
e) When E is $CR^9$ or $C(R^9)_2$, one $R^9$ group combines with an adjacent R1 to form a benzene ring;
f) The A-domain wherein the Z ring is completely saturated;
g) The A domain wherein the $R^{1a}$ is $C_1$-$C_8$ alkyl, $C_2$-$C_8$ alkenyl, (D)$C_5$-$C_6$ cycloalkyl, phenyl, or benzyl optionally substituted with halo;
h) $R^1$ is selected from:
  hydrogen,
  Hydroxy,
  Halo,
  $C_1$-$C_8$ alkyl,
  $C_1$-$C_8$ alkenyl,
  $C_1$-$C_4$ haloalkyl,
  (D)$C_3$-$C_7$ cycloalkyl,
  (D)aryl,
  (D)heteroaryl,
  (D)C(O)$C_1$-$C_8$ alkyl,
  (D)C(O)O$C_1$-$C_8$ alkyl,
  (D)C(O)heteroaryl, or
  $(CH_2)_m N(R^8)_2$; provided that when $R^1$ is halo, or hydroxy, it is not substituted on a carbon atom adjacent ( ) to a heteroatom; and p is 1.
i) $R^2$ is hydrogen, $C_1$-$C_8$ alkyl, $C_2$-$C_8$ alkoxy, (D)phenyl, or (D)$C_3$-$C_7$ cycloalkyl;

B Domains j) $R^3$ is phenyl optionally para-substituted with halo, trifluoromethyl, benzyl, benzyloxy, $C_1$-$C_2$ alkyl or $C_1$-$C_2$ alkoxy;
k) $R^3$ is phenyl optionally ortho-substituted with halo, trifluoromethyl, benzyl, benzyloxy, $C_1$-$C_2$ alkyl or $C_1$-$C_2$ alkoxy;
l) $R^3$ is phenyl optionally ortho and para-disubstituted with halo, trifluoromethyl, benzyl, benzyloxy, $C_1$-$C_2$ alkyl or $C_1$-$C_2$ alkoxy;
m) $R^3$ is thienyl;
n) $R^3$ is phenyl para-substituted with chloro;
o) $R^4$ is selected from H, methyl, ethyl, COMe, and COOMe;
p) the B domain is selected from the group consisting of:

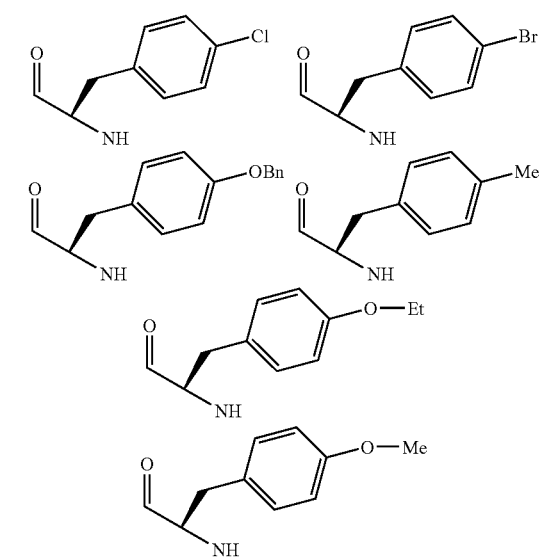

-continued

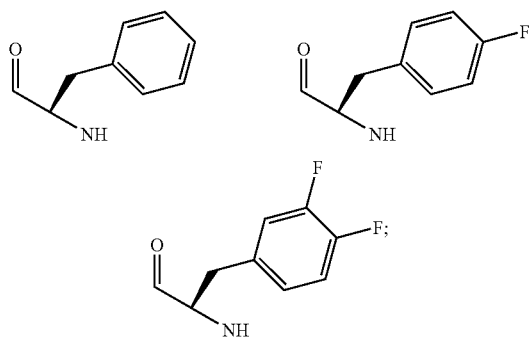

q) the B domain is selected from the group consisting of:

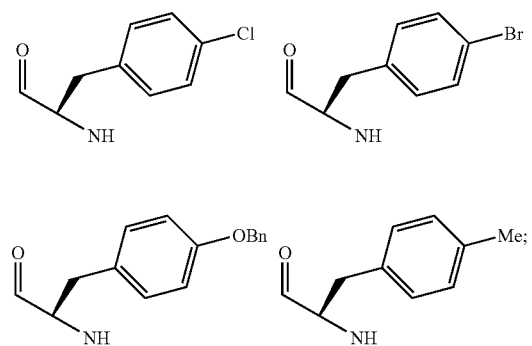

C Domains

The C-domain is represented by the formula —CLL$^1$-T. Preferred embodiments of the C-domain include:

r) T of the C-domain is selected from the group consisting of:

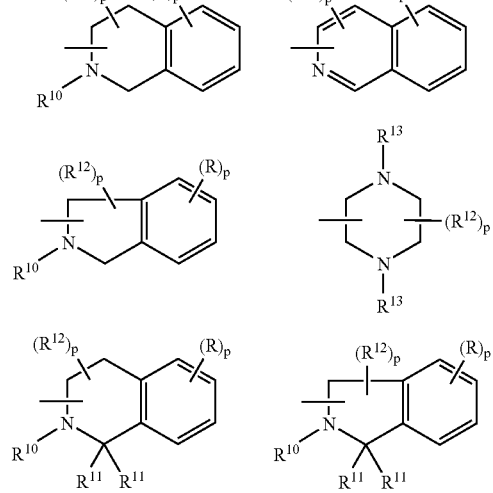

s) "T" of the C-domain is a moiety of the formula:

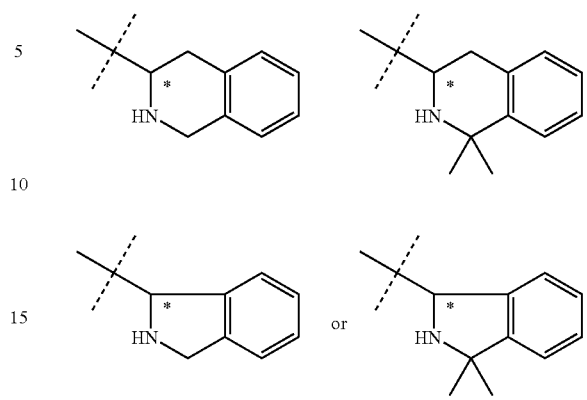

t) "T" of the C domain is a moiety selected from the group consisting of:

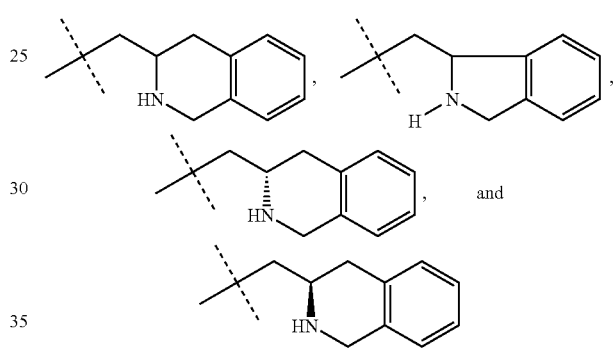

v) The C-domain is a moiety selected from the group consisting of:

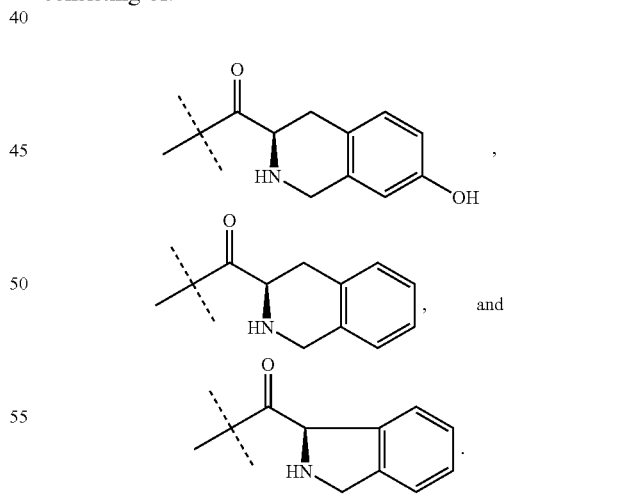

w) For -LL$^1$(CH$_2$)$_n$-T, n is 0, or 1 and LL$^1$ is oxo.

x) For -LL$^1$ (CH$_2$)$_n$-T, n is 0, or 1 and both L and L$^1$ are hydrogen.

Salt Forms u) the compound of formula I is an acid addition salt;

v) the compound of formula I is the hydrochloride salt.

Most preferred, is a compound selected from the group consisting of:

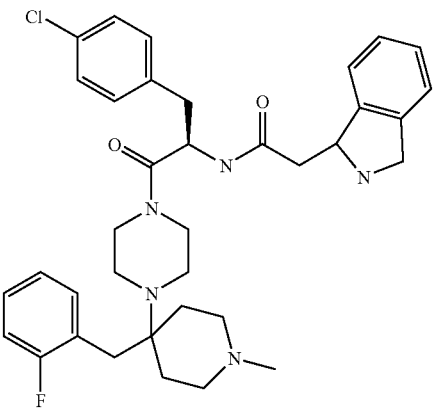

N-(1-(4-Chloro-benzyl)-2-{4-[4-(2-fluoro-benzyl)-1-methyl-piperidin-4-yl]-piperazin-1-yl}-2-oxo-ethyl)-2-(2,3-dihydro-1H-isoindol-1-yl)-acetamide,

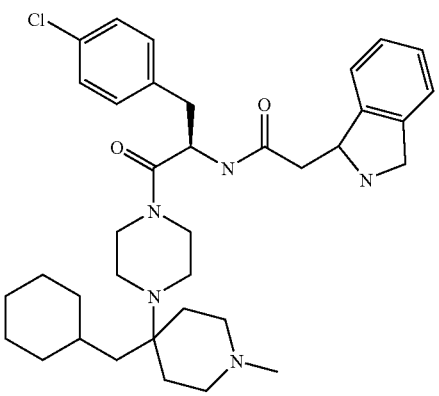

N-{1-(4-Chloro-benzyl)-2-[4-(4-cyclohexylmethyl-1-methyl-piperidin-4-yl)-piperazin-1-yl]-2-oxo-ethyl}-2-(2,3-dihydro-1H-isoindol-1-yl)-acetamide,

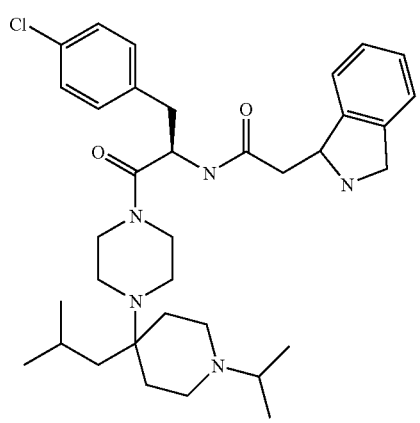

N-{1-(4-Chloro-benzyl)-2-[4-(4-isobutyl-1-isopropyl-piperidin-4-yl)-piperazin-1-yl]-2-oxo-ethyl}-2-(2,3-dihydro-1H-isoindol-1-yl)-acetamide,

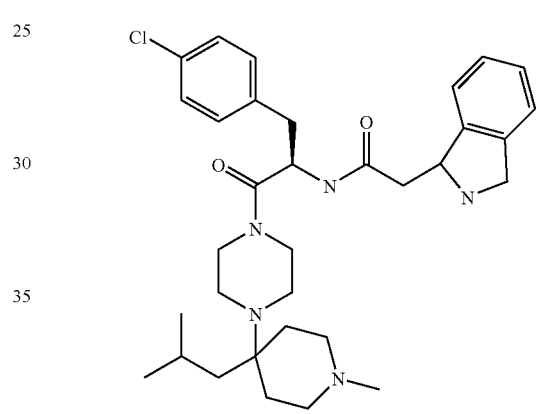

N-{1-(4-Chloro-benzyl)-2-[4-(4-isobutyl-1-methyl-piperidin-4-yl)-piperazin-1-yl]-2-oxo-ethyl}-2-(2,3-dihydro-1H-isoindol-1-yl)-acetamide,

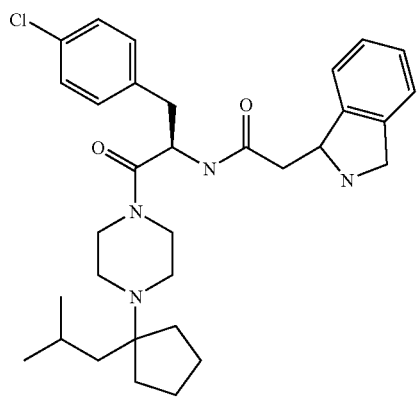

N-{1-(4-Chloro-benzyl)-2-[4-(1-isobutyl-cyclopentyl)-piperazin-1-yl]-2-oxo-ethyl}-2-(2,3-dihydro-1H-isoindol-1-yl)-acetamide,

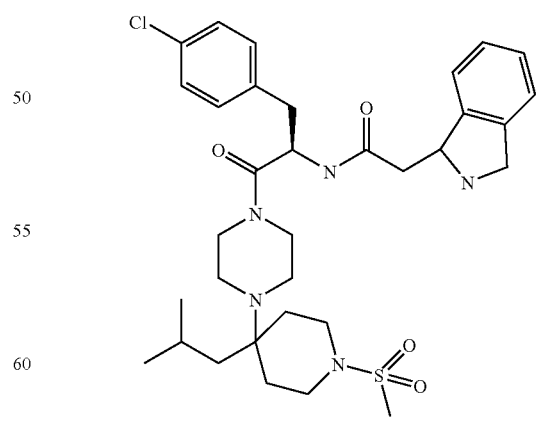

N-{1-(4-Chloro-benzyl)-2-[4-(4-isobutyl-1-methanesulfonyl-piperidin-4-yl)-piperazin-1-yl]-2-oxo-ethyl}-2-(2,3-dihydro-1H-isoindol-1-yl)-acetamide,

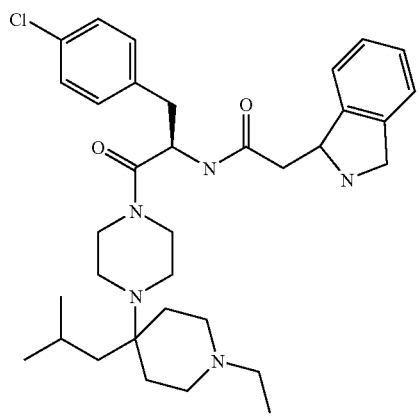

N-{1-(4-Chloro-benzyl)-2-[4-(1-ethyl-4-isobutyl-piperidin-4-yl)-piperazin-1-yl]-2-oxo-ethyl}-2-(2,3-dihydro-1H-isoindol-1-yl)-acetamide,

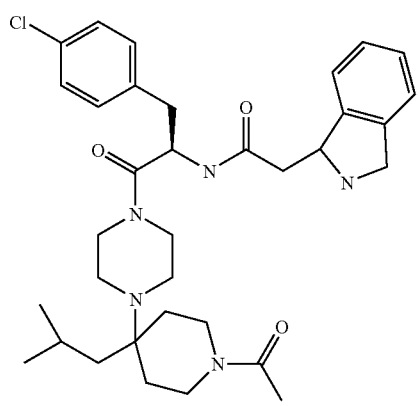

N-[2-[4-(1-Acetyl-4-isobutyl-piperidin-4-yl)-piperazin-1-yl]-1-(4-chloro-benzyl)-2-oxo-ethyl]-2-(2,3-dihydro-1H-isoindol-1-yl)-acetamide,

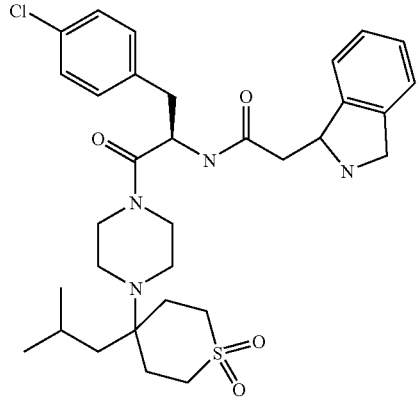

N-{1-(4-Chloro-benzyl)-2-[4-(4-isobutyl-1,1-dioxo-hexahydro-1λ6-thiopyran-4-yl)-piperazin-1-yl]-2-oxo-ethyl}-2-(2,3-dihydro-1H-isoindol-1-yl)-acetamide, Isomer 1

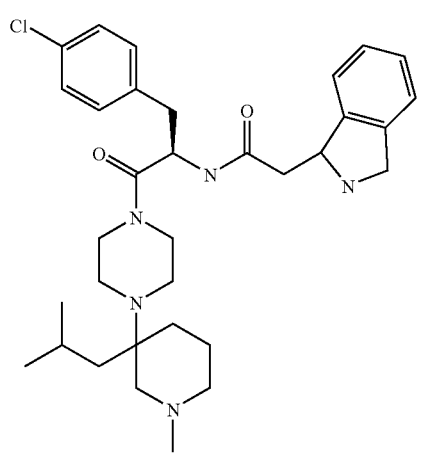

N-{1-(4-Chloro-benzyl)-2-[4-(3-isobutyl-1-methyl-piperidin-3-yl)-piperazin-1-yl]-2-oxo-ethyl}-2-(2,3-dihydro-1H-isoindol-1-yl)-acetamide, Isomer 2

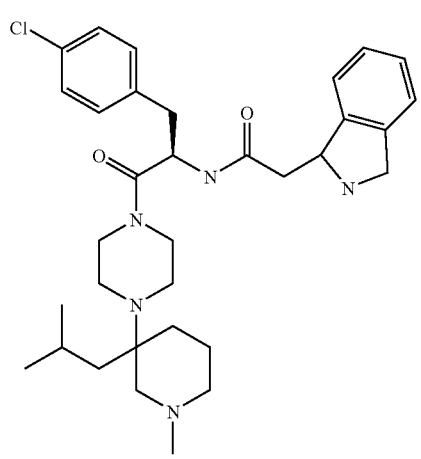

N-{1-(4-Chloro-benzyl)-2-[4-(3-isobutyl-1-methyl-piperidin-3-yl)-piperazin-1-yl]-2-oxo-ethyl}-2-(2,3-dihydro-1H-isoindol-1-yl)-acetamide,

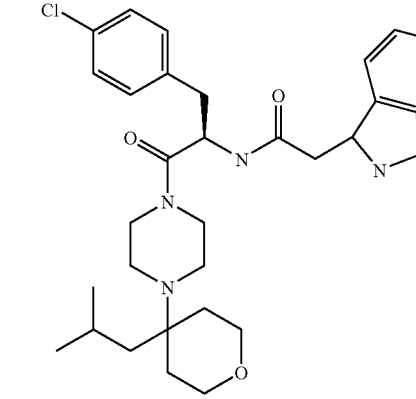

N-{1-(4-Chloro-benzyl)-2-[4-(4-isobutyl-tetrahydro-pyran-4-yl)-piperazin-1-yl]-2-oxo-ethyl}-2-(2,3-dihydro-1H-isoindol-1-yl)-acetamide, and

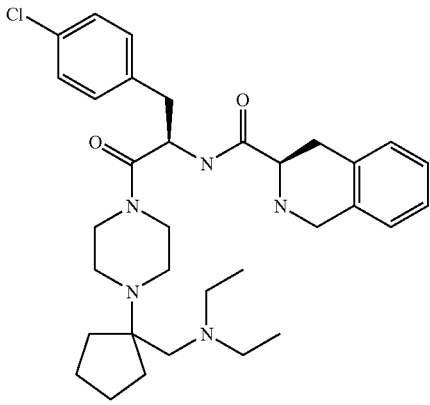

1,2,3,4-Tetrahydro-isoquinoline-3-carboxylic acid {1-(4-chloro-benzyl)-2-[4-(1-diethylaminomethyl-cyclopentyl)-piperazin-1-yl]-2-oxo-ethyl}-amide, and its pharmaceutically acceptable salt, solvate, prodrug and enantiomer thereof.

Making Compounds of the Invention

The preparation of the compounds of the present invention may be carried out via sequential or convergent synthetic routes. The skilled artisan will recognize that the three domains of a compound of formula I are connected via amide bonds or NH-bonds. The skilled artisan can, therefore, readily envision numerous routes and methods of connecting the three domains via standard peptide coupling reaction conditions optionally followed by reduction to the amine as desired.

The phrase "standard peptide coupling reaction conditions" means coupling a carboxylic acid with an amine using an acid activating agent such as EDC, DCC, and HATU, in a inert solvent such as DCM, in the presence of a catalyst such as HOBT. The uses of protective groups for amine and carboxylic acids to facilitate the desired reaction and minimize undesired reactions are well documented. Conditions required to remove protecting groups which may be present can be found in Greene, et al., *Protective Groups in Organic Synthesis*, John Wiley & Sons, Inc., New York, N.Y. 1991. CBZ and BOC protecting groups are used extensively in the synthesis, and their removal conditions are known to those skilled in the art. For example, removal of CBZ groups can be achieved by catalytic hydrogenation with hydrogen in the presence of a noble metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid. Removal of BOC protecting groups is carried out in a solvent such as DCM, methanol, or ethyl acetate, with a strong acid, such as TFA, HCl, or HCl gas.

However prepared, the compound of formula I, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of the formula I may be obtained by stereospecific synthesis using optically pure starting materials or reagents of known configuration. Additionally, any enantiomer of a compound may be separated by chiral chromatographaphy.

The A domains of the present invention, in general, may be prepared from commercially available starting materials via known chemical transformations. For example, a synthesis of certain A domains of the present invention is illustrated below in Schemes 1-2 below.

Scheme 1

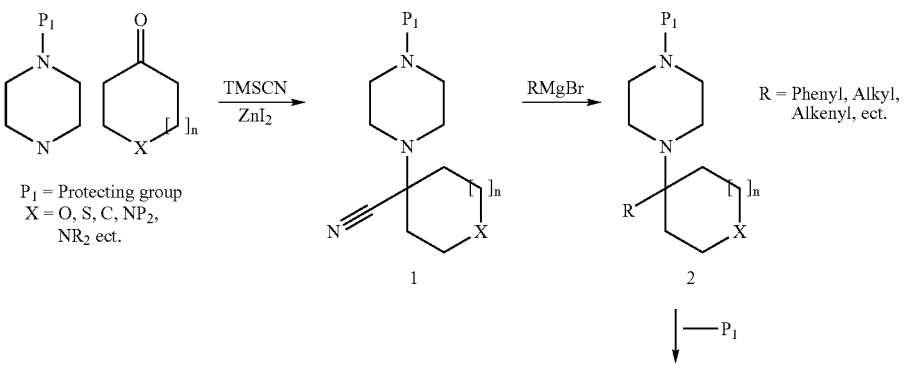

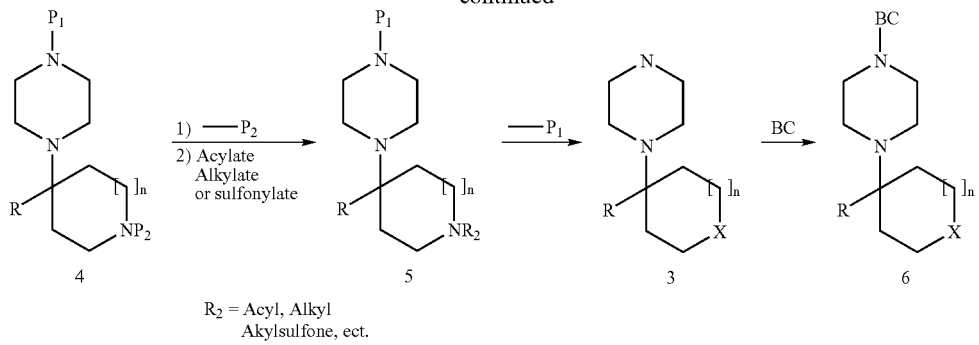

Scheme 1 shows a protocol to afford the A-domains of certain compounds of formula (I). According to Scheme 1, synthesis begins with the formation of the -amino nitrile of general structure 1 from a mono-protected piperazine and the appropriate cyclic ketone, for example cyclopentanone. $R_1$ is introduced via an akyl magnesium halide, which can be prepared by standard literature protocols, to yield compounds of type 2 and 4. Compounds of type 4 can be differentially de-protected and functionalized to yield compounds of general structure 5 where $R_2$ can be alkyl amide, sulfonamide or alkyl. Compounds of type 2 and 5 were deprotected by standard acid or palladium catalyzed protocols to yield compounds of general structure 3. By procedure common in the art, compounds of type 3 were coupled via an amide bond to yield melanocortin modulators of general structure 6.

Other A-domains of compounds of formula I are obtained following the protocol of Scheme 2.

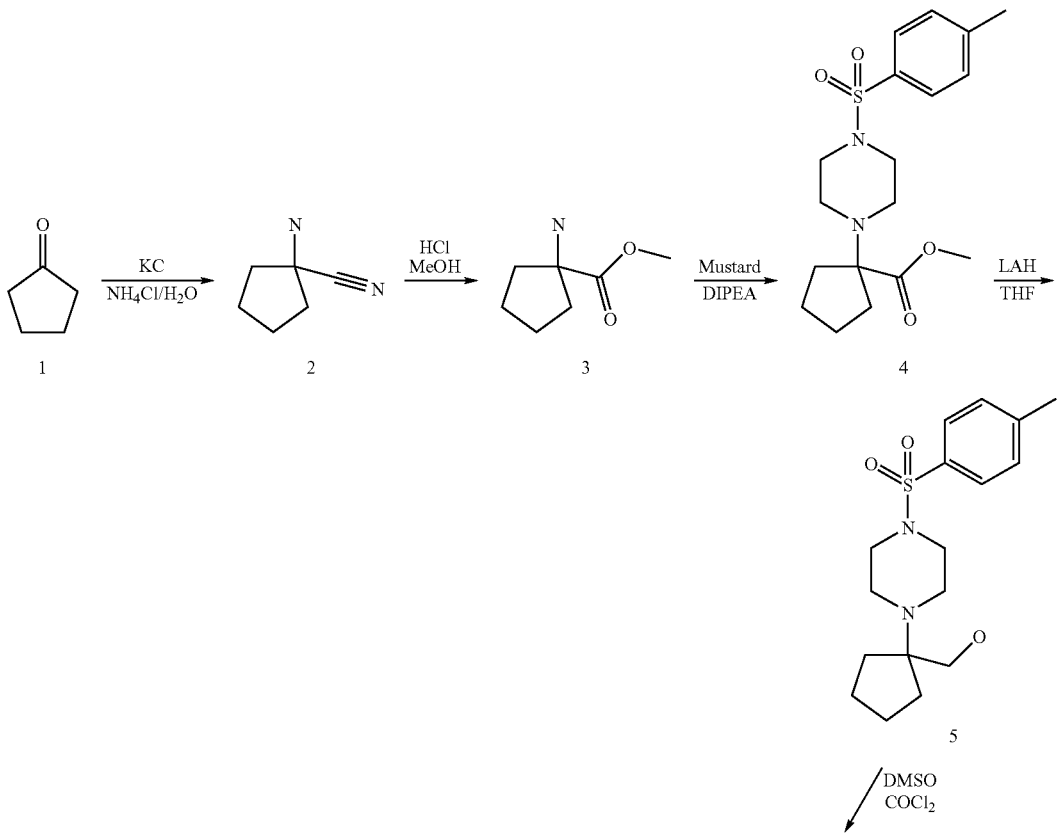

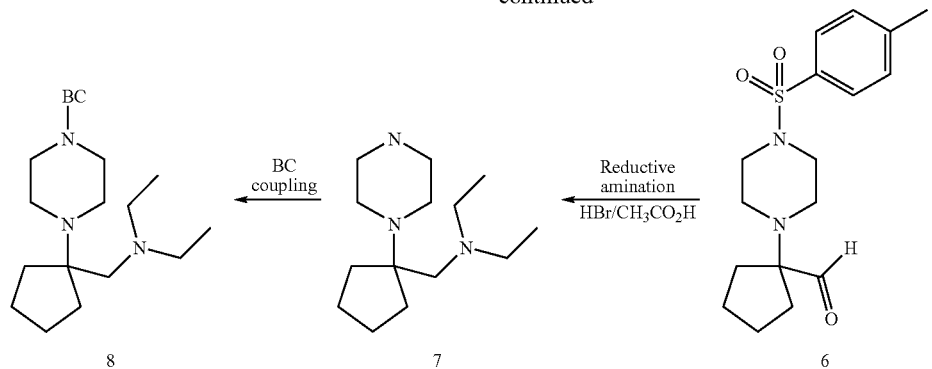

Compounds of formula (I) having the structure (8) or compounds derivable from (8) can be prepared as outlined in scheme 2. Compound 2 is prepared from the cyclic ketone 1 under classical Strecker conditions, which is then hydrolyzed and esterified with methanolic hydrochloric acid to yield compound 3. The piperazine ring of 4 is generated from a mustard and DIPEA. Compound 4 can then be reduced with LAH to yield the alkyl alcohol of 5. Compound 5 is then oxidized under Swern-oxidation conditions to yield 6. Reductive amination with diethyl amine followed by deprotection of the piperazine yields compound 7. By procedure common in the art, compound 7 was coupled via an amide bond to "BC" domain piece to yield melanocortin modulator of type 8.

Chiral resolution of a racemic "A" piece may be accomplished by chiral chromatography wherein the faster eluting isomer(s) are labeled isomer 1 and the next eluting isomer 2. Methods and protocols for chiral chromatography and other resolution methods are disclosed herein or known to one of skill in the art.

The "B" domain piece as used herein may be purchased or prepared from readily available starting materials. A preferred "B" domain piece is 4-chloro-D-Phenylalanine available commercially or by resolution of commercial racemic mixtures. The "B" domain may be coupled to an "A" domain which is then coupled to a "C" domain or the "B" domain may be coupled first to a "C" domain to form a "BC" domain piece, which is then coupled to an "A" domain piece. Coupling procedures for the above reactions were disclosed supra, and in the experimental section.

The present invention also provides novel processes for preparing certain intermediates and/or compounds of the invention. For example a convergent synthesis of a key intermediate isoindoline (5) (see Scheme 3 below) via a Heck coupling, followed by a reductive amination, a ring cyclization and a resolution has been achieved. Also, alternate asymmetric approaches including asymmetric Michael addition and asymmetric hydrogenation have been utilized to prepare compounds of the invention and/or intermediates thereof.

Scheme 3

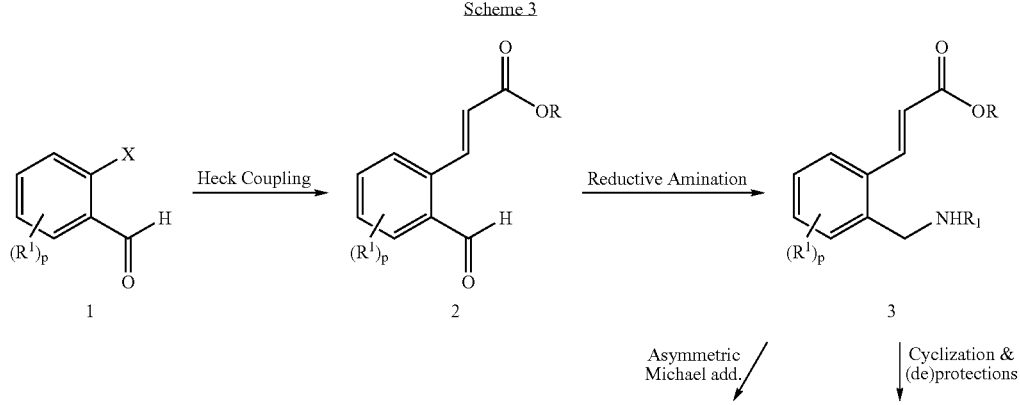

-continued

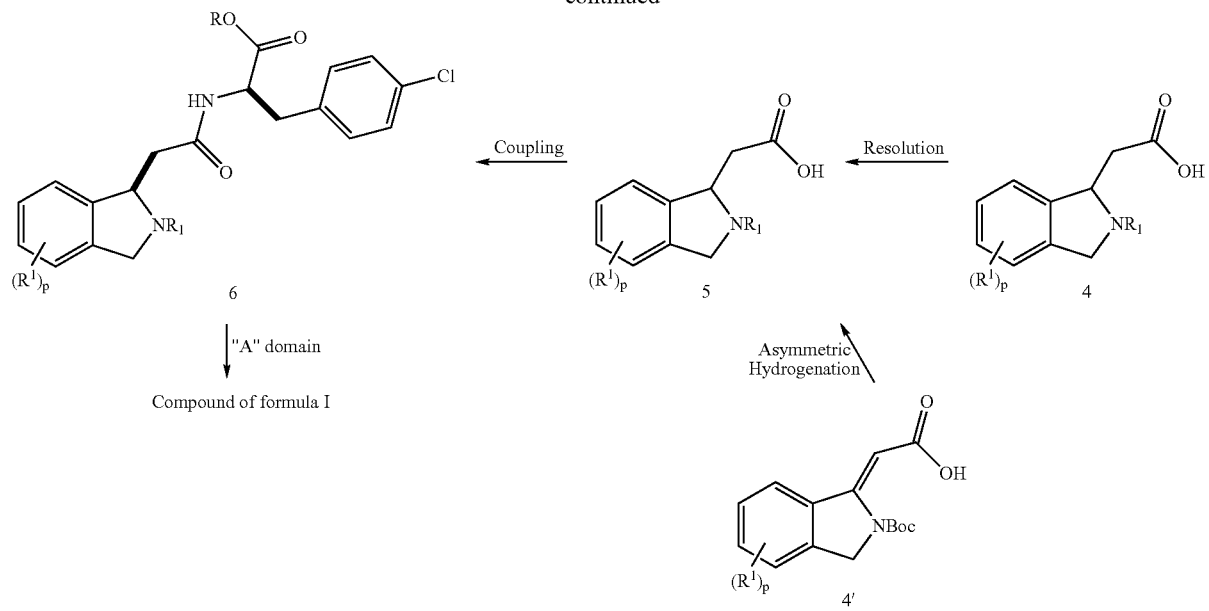

As shown in scheme 3, the isoindoline compounds of the present invention may be prepared from 2-halobenzaldehyde 1 or substituted analog thereof (scheme 3). Preferred starting material is 2-bromobenzaldehyde or substituted analog thereof. Pd-mediated Heck coupling of 2-bromobenzaldehydes 1 with for example, methyl acrylate, provided, β-unsaturated methyl esters 2, which undergoes reductive amination to give amines (or carbamates where $R_1$ is for example, Boc) 3. Various Heck coupling reagents and conditions were found suitable to effect the coupling reaction. Useful catalyst and ligands include $Pd(OAc)_2/PPh_3/Et_3N$, $Pd(OAc)PPh_3/BU_4NBr$, $Pd(PPh_3)_2Cl_2/CUI$, $Pd(OAC)_2/P(O-Tol)_3$. Suitable solvent or solvent systems for the Heck coupling reaction include DMF, toluene and ethyl acetate. Most preferred base is triethylamine.

Reductive amination of the aldehyde functionality of 2 to amines is accomplished in good yields by reaction with benzylamine or -methylbenzylamine in acidic conditions, followed by in situ reduction of the incipient imines with $NaCNBH_3$ at about pH 5. Other reducing agents including $Na(OAc)_3BH$ and $NaBH_4/H$ may also be used to effect reduction of the incipient imines. Interestingly, the resulting amines immediately cyclized to the isoindoline compounds under the same acidic conditions for the reduction.

Since the N-Boc group is part of certain target molecules of the invention, direct preparation of compound 4 may also be efected by use of $BocNH_2$ instead of benzylamine in the reductive amination step. Screening of various reducing agents demonstrated that the combination of $Et_3SiH$ and TFA in $CH_3CN$ represents the preferred method for effecting reductive amination using $BocNH_2$.

The N-Boc isoindolinecarboxylic acid 5 may also be prepared from 3 as the carbamate, by an intra-molecular Michael addition and ester hydrolysis. The resolution of the isoindolinecarboxylic acids 4 by crystallization afforded enantio-pure compounds 5.

Two alternate asymmetric approaches have also been developed for the synthesis of isoindolinecarboxylic acid 5 i.e. asymmetric Michael additions and asymmetric hydrogenation. In the asymmetric Michael addition approach, -methylbenzyl amine is used as a chiral auxiliary to induce the enantio-selectivity. In the asymmetric hydrogenation approach, compound 4' could be converted to 5 stereoselectively in the presence of chiral ligands.

Finally the coupling of the isoindolines 5 with the "B" domain piece, i.e. D-Cl-Phe to afford compound 6 ("BC" piece) is accomplished by standard amino acid coupling reactions such as, for example, by the use of EDC or EDCI or other activating agents in the presence of suitable base such as for example, dimethylaminopyridine (DMAP). The product (6) is then coupled with an "A" domain piece such as for example, 4-benzyl-4-bromo-1-methylpiperidinyl piperazine (compound 3D), as discussed herein to afford the target MC4R agonist compound of formula I by coupling reactions known to one of skill in the art.

Preferably, the isoindole or other "C" domain piece is coupled to an "AB" coupled domain piece to form the compound of formula I.

Compound of formula I having the isoquinoline functionality in the "C" domain may be prepared following Scheme 4 below, or modifications thereof:

Scheme 4

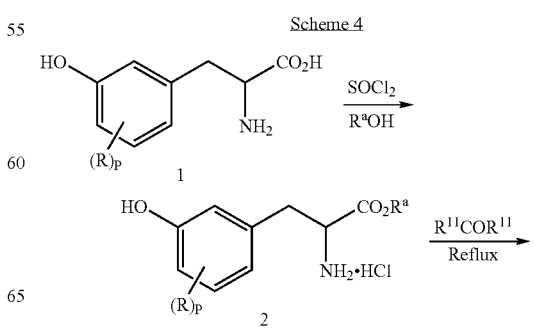

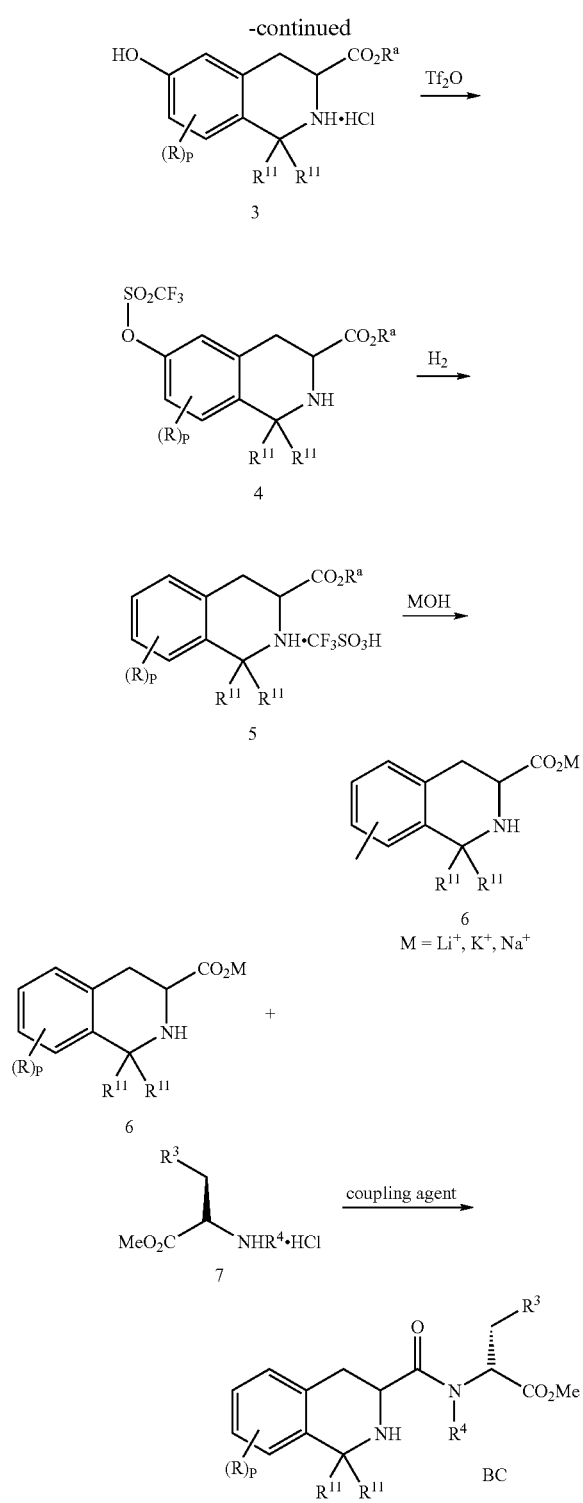

As shown in Scheme 4, m-tyrosine ester or analogs, including substituted analogs thereof, may be esterified by forming the acid halide followed by nucleophilic displacement the group OR⁻ from an alcohol, i.e. methanol or ethanol. Where thionyl chloride or other halide source is used the product may be isolated as the acid addition salt (2). The resulting ester (2) is subjected to a Pictet-Spengler reaction by heating with a suitable ketone or aldehyde in refluxing conditions. For example, an unsubstituted isoquinoline backbone (3) may be formed by employing formaldehyde in the pictet-Spengler reaction. On the other hand, a gem-dimethyl substituted isoquinoline wherein $R^{11}$ is methyl, may be formed by using acetone as the ketone source and solvent. The product isoquinoline (3) may be isolated preferably as the acid addition salt. Where m-tyrosine is used as the starting material, the free hydroxyl group is removed first by protection/activation with a good leaving group such as, for example, reaction with triflic anhydride (trifluoromethane sulfonic anhydride) or methanesulfonic acid to form the triflate or mesylate in the presence of a base. The triflate is a preferred group used to set up the compound (3) for deoxygenation because of the extra electron withdrawing effect of the trifluoromethane substituent. The deoxygenation reaction is effected by hydrogenation at pressures of about 50 psi. The product (4) may be isolated as the acid addition salt. The product (4) is hydrolyzed under basic conditions to afford the acid salt. Suitable bases for the above hydrolysis include aqueous sodium hydroxide, potassium hydroxide and lithium hydroxide. The reaction is preferably performed in a mixture of aqueous and organic solvents. An exotherm during addition of base may be regulated (i.e. less than about 35° C.) to avoid overheating or "runaway reactions." The reaction product may be isolated by aqueous work up. Alternatively, the entire mixture may be concentrated and washed with organic solvents to afford the desired product (6) after crystallization.

The product (6) is then reacted with a "B" domain substrate such as, for example, 4-chloro-D-phenylanine as described previously and in the experimental section. The resulting "BC" combination product is then reacted with an "A" domain such as, for example, diethyl-(2-phenyl-2-piperazin-1yl-ethyl)-amine to form the respective compound of formula I. Alternatively, the product (6) may be reacted with an "AB" domain combination product to afford a compound of formula I.

One of skill is aware that certain protections and deprotections of intermediates in Scheme 4, to form the carbamate, substituted amine or free amine at the isoquinolinyl nitrogen are possible and contemplated as within the scope of this invention. Unless otherwise specified, reagents and procedures for effecting the reactions described herein are known to one of skill in the art and may be found in general reference texts such as *Advanced Organic Chemistry* by J. March, 5th edition, Wiley Interscience Publishers, New York, N.Y., and references therein.

In an alternate procedure, the isoquinoline product i.e. compound (3) or (5) including their protected analogs may be resolved by reaction with a resolving agent such as for example, L-tartaric acid, dehydroabietylamine or other resolving agents known to one of skill in the art.

Alternatively, asymmetric analogs of product (6) may be prepared by using asymmetric starting materials. For example, L-DOPA may be used in place of m-tyrosine ester in reactions essentially similar to those described and illustrated in Scheme 4, and in the examples to afford the asymmetric analog of compound (6).

Tetrahydroisoquinoline acetic acid derivates may be prepared and utilized as shown in Scheme 10a below:

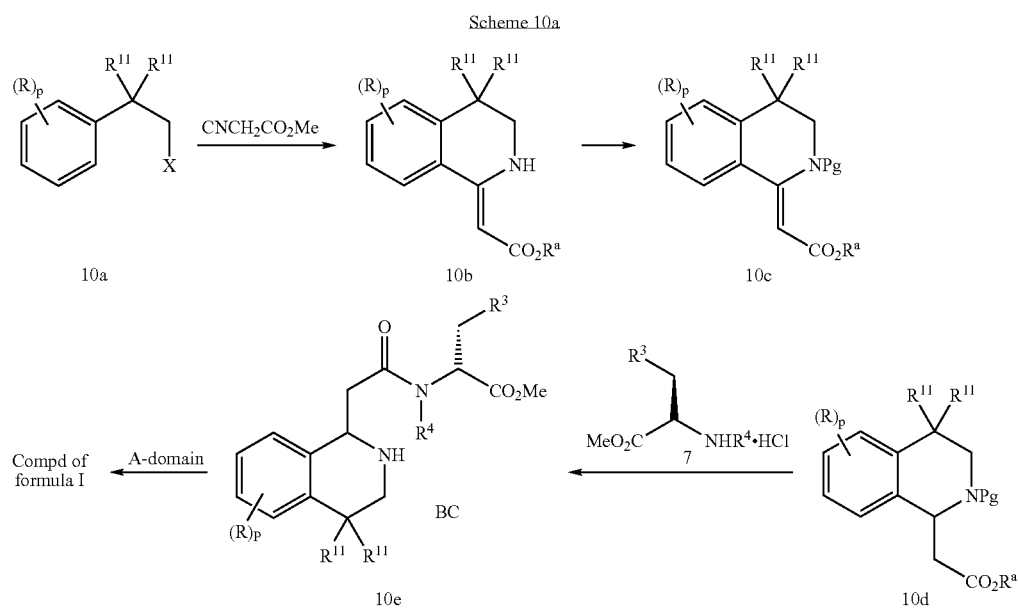

Scheme 10a

As shown in Scheme 10a, a compound of formula 10a wherein X is halogen, preferably bromo or chloro, and R and $R^{11}$ are as defined previously, and which is obtained commercially or prepared from commercial starting materials is reacted with cyanomethylethylacetate to afford a compound of formula 10b. The compound of formula 10b may be protected as the compound 10c with a suitable protecting group (Pg) and then subjected to hydrogenation conditions including for example asymmetric hydrogenation to form a compound of formula 10d which may be chiral (depending on hydrogenation conditions, i.e. asymmetric versus non-assymetric hydrogenation). The compound of formula 10d or steroisomer thereof, is reacted with a B-domain piece such as, for example, 4-chloro-D-phe to afford a BC piece (10e). The compound of formula 10e is then reacted with an A-domain piece to afford a compound of formula I. The details of the specific reaction steps are similar to or analogous to reactions taught herein, and in the experimental section. Furthermore, one of skill in the art is aware of that such intermediate reactions as hydrolysis and deprotection may be necessary to achieve optimum yields in certain steps of the scheme as shown. One of skill in the art is also aware of further common manipulations such as N-alkylation or acylation, and alkylations on the benzene ring to afford other compounds of formula I.

Formulation

The compound of formula I is preferably formulated in a unit dosage form prior to administration. Therefore, yet another embodiment of the present invention is a pharmaceutical composition comprising a compound of formula I and one or more pharmaceutically acceptable carriers, diluents or excipients.

The present pharmaceutical compositions are prepared by known procedures using well-known and readily available ingredients. In making the formulations of the present invention, the active ingredient (formula I compound) will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

Dose

The specific dose administered is determined by the particular circumstances surrounding each situation. These circumstances include, the route of administration, the prior medical history of the recipient, the pathological condition or symptom being treated, the severity of the condition/symptom being treated, and the age and sex of the recipient. However, it will be understood that the appropriate caregiver in light of the particular circumstances of the patient or recipient will determine the therapeutic dosage administered.

Generally, an effective minimum daily dose of a compound of formula I is about 1, 5, 10, 15, or 20 mg. Typically, an effective maximum dose is about 500, 100, 60, 50, or 40 mg. The exact dose may be determined, in accordance with the standard practice in the medical or veterinary arts of "dose titrating" the recipient; that is, initially administering a low dose of the compound, and gradually increasing the does until the desired therapeutic effect is observed.

Route of Administration

The compounds may be administered by a variety of routes including the oral, rectal, transdermal, subcutaneous, topical, intravenous, intramuscular or intranasal routes.

Combination Therapy

Compounds of Formula I may be used in combination with other drugs that are used in the treatment of the diseases or conditions for which compounds of formula I are useful. Such other drugs may be administered, by a route and in an amount commonly used therefor, contemporaneously or sequentially with a compound of formula I. When a compound of formula I is used contemporaneously with one or more other drugs, a pharmaceutical composition containing such other drugs in addition to the compound of formula I is preferred. Accordingly, the pharmaceutical compositions of the present invention include those that also contain one or more other active ingredients, in addition to a compound of formula I. Examples of other active ingredients that may be combined with a compound of formula I, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide;

(d) alpha glucosidase inhibitors (such as acarbose), (e) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (iii) nicotinyl alcohol nicotinic acid or a salt thereof, (iv) proliferator-activater receptor alpha agonists such as fenofibric acid derivatives (gemfibrozil, clofibrat, fenofibrate and benzafibrate), (v) inhibitors of cholesterol absorption for example beta-sitosterol and (acyl CoA:cholesterol acyltransferase) inhibitors for example melinamide, (vi) probucol, (vii) vitamin E, and (viii) thyromimetics;

(f) PPARδ agonists such as those disclosed in WO97/28149;

(g) antiobesity compounds such as fenfluramine, dexfenfluramine, phentermine, sibutramine, orlistat, and other beta-3 adrenergic receptor agonists such as those described in U.S. patent application Ser. Nos. 60/217,965, 60/241,614 and 60/247,304;

(h) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(i) PPAR alpha agonists such as described in WO 97/36579 by Glaxo;

(j) PPARγ antagonists as described in WO97/10813;

(k) serotonin reuptake inhibitors such as fluoxetine and sertraline;

(l) growth hormone secretagogues such as MK-0677; and (m) agents useful in the treatment of male and/or female sexual dysfunction such as phosphodiester V inhibitors such as sildenafil and ICI-351, and alpha-2 adrenergic receptor antagonists, such as phentolamine mesylate; and dopamine-receptor agonists, such as apomorphine.

Demonstration of Function:

A. Binding Assay.

The radioligand binding assay is used to identify competitive inhibitors of $^{125}$I-NDP-alpha-MSH binding to cloned human MCRs using membranes from stably transfected human embryonic kidney (HEK) 293 cells.

HEK 293 cells transfected with human or rat melanocortinin receptors are grown either as adherent monolayers or suspension culture. Monolayer cells are grown in roller bottle cultures at 37° C. and 5% $CO_2$/air atmosphere in a 3:1 mixture of Dulbecco's modified Eagle medium (DMEM) and Ham's F12 containing 25 mM L-glucose, 100 units/ml penicillin G, 100 microgram/ml streptomycin, 250 nanogram/ml amphoterin B, 300 microgram/ml genticin and supplemented with 5% fetal bovine serum. Monolayer cells are adapted to suspension culture (Berg et al., Biotechniques Vol. 14, No.6, 1993) and are grown in spinner or shaker flasks (37° C. and 7.5% $CO_2$/air overlay) in a modified DME/F12 medium containing 0.1 mM $CaCl_2$, 2% equine serum and 100 microgram/ml sodium heparin (to prevent cell-cell aggregation). Cells are harvested by centrifugation, washed in PBS, and pellets are stored frozen at −80° C. until membrane preparations.

The cell pellets are resuspended in 10 volumes of membrane preparation buffer (i.e., 1 g pellet to 10 ml buffer) having the following composition: 50 mM Tris pH 7.5 @ 4° C., 250 mM sucrose, 1 mM $MgCl_2$, Complete® EDTA-free protease inhibitor tablet (Boehringer Mannheim), and 24 micrograms/ml DNase I (Sigma, St. Louis, Mo.). The cells are homogenized with a motor-driven dounce using 20 strokes, and the homogenate is centrifuged at 38,000×g at 4° C. for 40 minutes. The pellets are resuspended in membrane preparation buffer at a concentration of 2.5-7.5 mg/ml and 1 milliliter aliquots of membrane homogenates are quickly frozen in liquid nitrogen and then stored at −80° C.

Solutions of a compound of formula I (300 picomolar to 30 micromolar) or unlabelled NDP-alpha-MSH (1 picomolar to 100 nanomolar) are added to 150 microliters of membrane binding buffer to yield final concentrations (listed in parantheses). The membrane binding buffer has the following composition: 25 mM HEPES pH 7.5; 10 mM $CaCl_2$; 0.3% BSA). One hundred fifty microliters of membrane binding buffer containing 0.5-5.0 microgram membrane protein is added, followed by 50 nanomolar $^{125}$I-NDP-alpha-MSH to final concentration of 100 picomolar. Additionally, fifty microliters of SPA beads (5 mg/ml) are added and the resulting mixture is agitated briefly and incubated for 10 hours at room temperature. The radioactivity is quantified in a Wallac Trilux Microplate Scintillation counter. $IC_{50}$ values obtained in competition assays are converted to affinity constants ($K_i$ values) using the Cheng-Prusoff equation:

$$K_i = IC_{50}/(1+D/K_d).$$

B. Functional Assays.

Functional cell based assays are developed to discriminate agonists and antagonists.

Agonist Assay: HEK 293 cells stably expressing a human melanocortin receptor (see e.g., Yang, et al., *Mol-Endocrinol.*, 11(3): 274-80, 1997) are dissociated from tissue culture flasks using a trypsin/EDTA solution (0.25%; Life Technologies, Rockville, Md.). Cells are collected by centrifugation and resuspended in DMEM (Life Technologies, Rockville, Md.) supplemented with 1% L-glutamine and 0.5% fetal bovine serum. Cells are counted and diluted to 4.5×10$^5$/ml.

A compound of formula I is diluted in dimethylsulfoxide (DMSO) ($3\times10^{-5}$ to $3\times10^{-10}$ M final concentrations) and 0.05 volume of compound solution is added to 0.95 volumes of cell suspension; the final DMSO concentration is 0.5%. After incubation at 37° C./5% $CO_2$ for 5 hours, cells are lysed by addition of luciferin solution (50 mM Tris, 1 mM $MgCl_2$, 0.2% Triton-X100, 5 mM DTT, 500 micromolar Coenzyme A, 150 micromolar ATP, and 440 micromolar luciferin) to quantify the activity of the reporter gene luciferase, an indirect measurement of intracellular cAMP production.

Luciferase activity is measured from the cell lysate using a Wallac Victor 2 luminometer. The amount of lumen production which results from a compound of formula I is compared to that amount of lumens produced in response to NDP-alpha-MSH, defined as a 100% agonist, to obtain the relative efficacy of a compound. The $EC_{50}$ is defined as the compound concentration that results in half maximal stimulation, when compared to its own maximal level of stimulation.

Melanocortin Receptor Whole Cell cAMP Accumulation Assay Compound Preparation:

In the agonist assay, compounds are prepared as 10 mM and NDP-aMSH (control) as 33.3 µM stock solutions in 100% DMSO. These are serially diluted in 100% DMSO. The compound plate is further diluted 1:200 in compound dilution buffer (HBSS-092, 1 mM Ascorbic Acid, 1 mM IBMX, 0.6% DMSO, 0.1% BSA). The final concentration range being 10 µM-100 pM for compound and 33.33 nM-0.3 pM for control in 0.5% DMSO. Transfer 20 µl from this plate into four PET 96-well plates (all assays are performed in duplicate for each receptor).

Cell Culture and Cell Stimulation:

HEK 293 cells stably transfected with the MC3R and MC4R were grown in DMEM containing 10% FBS and 1% Antibiotic/Antimycotic Solution. On the day of the assay the cells were dislodged with enzyme free cell dissociation solution and resuspended in cell buffer (HBSS-092, 0.1% BSA, 10 mM HEPES) at 1×e6 cells/ml. Add 40 µl of cells/well to the PET 96-well plates containing 20 ul diluted compound and control. Incubate @ 37° C. in a waterbath for 20 minutes. Stop the assay by adding 50 µl Quench Buffer (50 mM Na Acetate, 0.25% Triton X-100).

Radioligand Binding Assays:

Radioligand binding assays were run in SPA buffer (50 mM Sodium Acetate, 0.1% BSA). The beads, antibody and radioligand were diluted in SPA buffer to provide sufficient volume for each 96-well plate. To each quenched assay well was added 100 ul cocktail containing 33.33 ul of beads, 33.33 µl antibody and 33.33 µl $^{125}$I-cAMP. This was based on a final concentration of 6.3 mg/ml beads, 0.65% anti-goat antibody and 61 pM of $^{125}$I-cAMP (containing 25000-30000 CPM) in a final assay volume of 210 µl. The plates were counted in a Wallac MicroBeta counter after a 12-hour incubation.

The data was converted to pmoles cAMP using a standard curve assayed under the same conditions. The data was analyzed using Activity Base software to generate agonist potencies ($EC_{50}$) and percent relative efficacy data to NDP-aMSH.

C. In Vivo Food Intake Models.

1) Overnight food intake. Sprague Dawley rats are injected intracerebroventricularly with a test compound in 400 nL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 hours post compound administration is measured.

2) Food intake in diet induced obese mice. Male C57/B16J mice maintained on a high fat diet (60% fat calories) for 6.5 months from 4 weeks of age are dosed intraperitoneally with a compound of formula I. Food intake and body weight are measured over an eight day period. Biochemical parameters relating to obesity, including leptin, insulin, triglyceride, free fatty acid, cholesterol and serum glucose levels are determined.

D. Rat Ex Copula Assay.

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests. This conditioning takes about 4 days. Day 1, the animals are placed in a darkened restrainer and left for 15-30 minutes. Day 2, the animals are restrained in a supine position in the restrainer for 15-30 minutes. Day 3, the animals are restrained in the supine position with the penile sheath retracted for 15-30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation, animals are given a treat to ensure positive reinforcement.

2) Ex Copula Reflex Tests. Rats are gently restrained in a supine position with their anterior torso placed inside a cylinder of adequate size to allow for normal head and paw grooming. For a 400-500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copulu genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and/or vehicle evaluations are conducted to determine how and if an animal will respond. Some animals have a long duration until the first response while others are non-responders altogether. During this baseline evaluation, latency to first response time, number and type of responses are recorded. The testing time frame is 15 minutes after the first response.

After a minimum of 1 day between evaluations, these same animals are administered a compound of formula I at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICY).

E. Models of Female Sexual Dysfunction.

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna, et al., *Am. J. Physiol.*, (Regulatory Integrative Comp. Physiol 30):R1276-R1285, 1991; McKenna, et al., *Pharm. Bioch. Behav.*, 40:151-156, 1991; and Takahashi, et al., *Brain Res.*, 359:194-207, 1985.

Sample assay results for compounds of the invention is provided in the results table below:

Results

| Compound | MC4 Ki (nM) | MC4 EC$_{50}$ (nM) | % Rel. Eff. |
|---|---|---|---|
| 5I | 9 | 4.3 | 104 |
| 4I | 24.3 | 18.9 | 114 |
| 8I | 28.8 | 99.8 | 124 |
| 10I | 6.5 | 25.4 | 112 |

Experimental Section

The following abbreviations have been used in this application for brevity.

| | |
|---|---|
| BINAP | 2,2'-Bis(diphenylphosphino)-1,1'-binaphthyl |
| Boc | t-butoxycarbonyl |
| CBZ | benzyloxycarbonyl |
| DCM | dichloromethane |
| DEAD | diethyl azodicarboxylate |
| DIPEA | diisopropylethylamine (also DIEA) |
| DMAP | 4-dimethylamino pyridine |
| DMF | N,N-dimethylformamide |
| DMSO | dimethylsulfoxide |
| eq. | equivalent(s) |
| EDC | 1-(3-dimethylaminopropyl)-3-ethylcarbodiimide HCl |
| ESI-MS | electron spray ion-mass spectroscopy |
| Et | ethyl |
| EtOAc | ethyl acetate |
| HATU | O-(7-azabenzotriazol-1-yl)-N,N,N',N' tetramethyluronium hexafluorophosphate |
| HOAT: | 1-hydroxy-7-azabenzotriazole |
| HOBT | 1-hydroxybenzotriazole hydrate |
| HPLC | high performance liquid chromatography |
| HRMS | high resolution mass |
| MS | mass spectroscopy |
| | LRMS low resolution mass |
| Me | methyl |
| Ms | methylsulfonyl |
| Pd$_2$(dba)$_3$ | tris(dibenzylideneacetone)-dipalladium(0) |
| Ph | phenyl |
| Phe | phenylalanine |
| Pr | propyl |
| TBS | tertbutyldimethylsilyl |
| TFA | trifluoroacetic acid |
| TEA | triethylamine |
| THF | tetrahydrofuran |
| Tic | 1,2,3,4-tetrahydroisoquinoline-3-carboxylic acid |
| TLC | thin-layer chromatography |
| h | hour |
| rt | room temperature also r.t. or RT |

The following experimentals describe the synthesis of mc4 agonists of formula I of the motif below. In general B and C pieces were prepared as described and coupled to form coupled B-C pieces (see preparations BC1 to BC18 for example). The B-C coupled pieces were in turn coupled to A-pieces prepared as described infra.

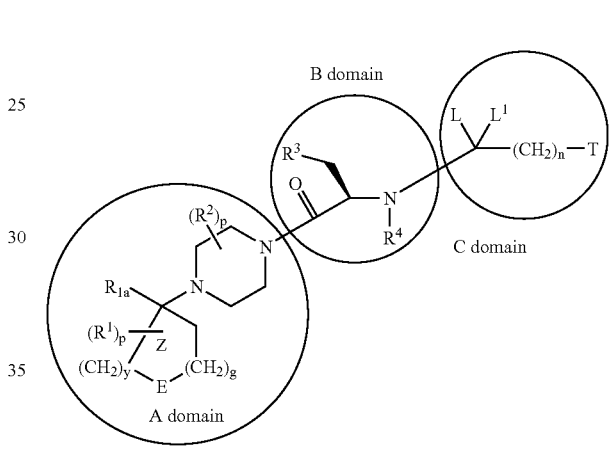

Preparation of Novel C-Domain Pieces

Heck Coupling

Preparation PP1

Synthesis of Compound (2a) by a Heck Coupling of 2-bromobenzaldehyde (1a) with Methyl Acrylate(Pd(OAc)$_2$/PPh$_3$ as the catalyst)

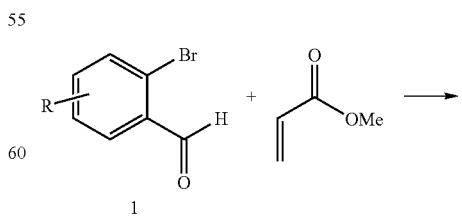

1

1a R = H
1b R = 5-OMe
1c R = 4,5-OMe
1d R = 5-NO$_2$

-continued

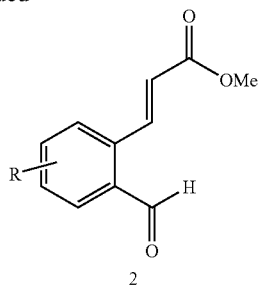

2a R = H
2b R = 5-OMe
2c R = 4,5-OMe
2d R = 5-NO₂

A mixture of 2-bromobenzaldehye (1a) (24.5 g, 132 mmol), methyl acrylate (17.9 mL, 199 mmol), Pd(OAc)₂ (590 mg, 2.65 mmol, 2 mol %), PPh₃ (1.39 g, 5.30 mmol, 4 mol %) and Et₃N (46 mL, 331 mmol) was stirred at 80° C. for 15 h. Large amount of yellow solid was formed after the reaction was done. The mixture was cooled to rt, concentrated, and mixed with H₂O (200 mL). The organic solid was collected by filtration, and then applied to a plug of silica gel (25 g) (EtOAc/hexane 1:1) to give a dark yellow solid. The solid was purified by crystallization (100 mL EtOAc bottom layer, 120 mL hexane top layer) to provide 17.57 g (70%) (100% pure by NMR) of the first crop and 5.23 g (21%) (95% by NMR) of the second crop of 2a.

Preparation PP2

Synthesis of Compound (2a) by a Heck Coupling of 2-bromobenzaldehyde (1a) with Methyl Acrylate (R=H)(Pd(OAc)₂/P(O-Tolyl)₃ as the catalyst)

Compound 1a (9.998 g, 54.04 mmol) was dissolved in toluene (20 mL) at RT. Methylacrylate (5.996 g, 69.65 mmol, 1.29 eq.), NEt₃ (15 mL), Pd(OAc)₂ and P(O-Tolyl)₃ were successively added and the mixture was stirred under reflux. After 2 hours, the reaction mixture was allowed to cool to RT. Then the precipitated yellow catalyst was removed by filtration. The catalyst was rinsed with toluene (2×10 mL) and the filtrates were concentrated to dryness under reduced pressure. The residual oil was dried under vacuum over the weekend to give a crude solid (11.449 g). The solid was taken-up with isopropanol (25 mL) and stirred overnight at RT. Then, the precipitate was filtered and rinsed with isopropanol (5 mL). The wet cake (8.240 g) was dried overnight at RT affording the highly pure 2-carboxaldehyde-methyl-cinnamate with 74% yield (7.627 g, 40.1 mmol).

Preparation PP3

Heck Coupling of 1b and Methyl Acrylate to Form 2b (R=5-OMe)

A mixture of 2-bromo-5-methoxybenzaldehyde (1b) (4.5 g, 20.9 mmol, Aldrich), methyl acrylate (2.7 g, 1.5 eq, 2.83 mL), Et₃N (7.4 g, 3.5 eq, 10.2 mL), Pd(OAc)₂ (93 mg, 0.02 eq), and P(O-Tol)₃ was stirred and heated to 80° C. over 2-3 days. The reaction mixture was cooled to RT, partitioned between EtOAc (50 mL) and brine (50 mL). The aqueous was extracted with EtOAc (2×50 mL). The combined organic was washed with brine (1×50 mL), dried over MgSO₄, filtered, concentrated to yield a yellow brown oil (5.01 g, 109%). This crude oil was purified in a hot solvent Hex/EtOAc (80 mL/15 mL) to yield 2b as a pale yellow solid (3.5 g, 76%).

Preparation PP4

Heck Coupling of 1c and Methyl Acrylate to Form 2c (R=4,5-OMe)

To a solution of 1c (906 mg, 3.70 mmol) in toluene (2 mL) was added Pd(OAc)₂ (17 mg, 0.074 mmol, 2 mol %), P(O-Tolyl)₃ (45 mg, 0.148 mmol, 4 mol %), methyl acrylate (0.5 mL, 5.55 mmol) and Et₃N (1.5 mL, 11.1 mmol). The mixture was stirred at 80° C. for 21 h, cooled to rt, and mixed with H₂O (40 mL). The organic compounds were extracted with EtOAc (50 mL), washed with brine (40 mL), dried (Na₂SO₄), and concentrated. The residue was purified by flash chromatography to provide 466 mg (47%) of recovered 1c followed by 450 mg (49%) of 2c (4,5-Ome).

Preparation PP5

Heck Coupling of 1d and Methyl Acrylate to Form 2d (R=5-NO₂)

The procedure is same as that of 2c, yielding 82% of 2d after purification.

Reductive Amination

Preparation PP6

Reductive amination of (2a) with benzyl amine to form isoindoline (10a)

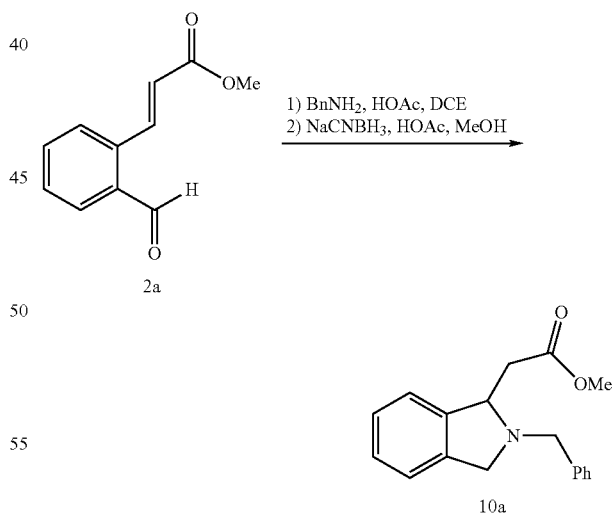

To a solution of 2a (11.27 g, 59.2 mmol) in ClCH₂CH₂Cl (60 mL) was added BnNH₂ (6.47 mL, 59.2 mmol), followed by HOAc (5.1 mL, 89 mmol). The mixture was stirred at rt for 1 h. NaCNBH₃ (5.58 g, 88.8 mmol) and MeOH (30 mL) were then added to the above solution. The resulting mixture was stirred at rt for another 2 h and quenched with sat. NaHCO₃ solution (150 mL). The mixture was extracted with EtOAc (2×100 mL) and the combined organic layers were washed with brine (150 mL), dried (Na₂SO₄), and concentrated to provide 15.3 g of crude product of 10a which was carried out for the next hydrogenolysis reaction.

Preparation PP7

One-pot process from 2-carboxaldehyde-methyl-cinnamate to target cyclized isoindoline product using NaBH₃CN

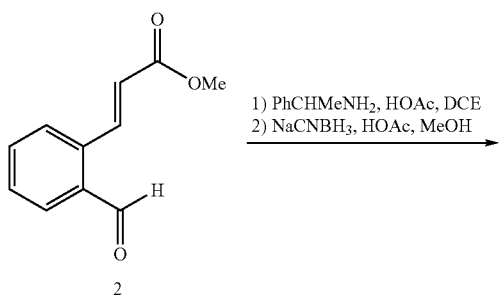

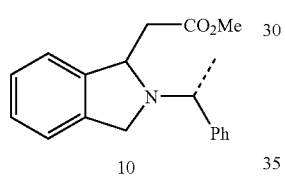

2-carboxaldehyde-methyl-cinnamate 2a (3.254 g, 17.1 mmol) was dissolved in a 1:1 MeOH: PhCH₃ mixture (20 mL) at RT. R-(+)-phenethylamine (2.073 g, 17.1 mmol) was added and the solution was heated under reflux for 2 hours. HPLC in process control indicated that the imine formation was completed. Then, AcOH (2.055 g, 34.2 mmol) and NaBH₃CN (2.15 g, 34.2 mmol) were successively added at RT, the reaction mixture being cooled with a water-bath. The reaction mixture was post-agitated overnight. Water (10 mL), MeOH (20 mL) and 37% HCl (2.8 mL) were successively added and the organic layer was extracted. The aqueous layer was washed with PhCH₃ (10 mL). Then, the aqueous layer was made basic with 5N NaOH (20 mL) and MeOH was concentrated to partly remove MeOH. Extraction with EtOAc (2×25 mL) was performed. The combined organic layers were dried over MgSO4, filtered and rinsed with EtOAc (10 mL). The filtrates were concentrated under reduced pressure and the residual oil was dried under vacuum overnight at RT to afford the target cyclized isoindoline product 10b with 92% yield (4.642 g, 15.7 mmol). HPLC % area indicated that the 2 diastereomers were produced in a 55:45 ratio. ¹H NMR confirmed this result by integration of the methyl group of the phenethyl substituent.

Note: The Heck or Heck-type coupling was performed in toluene with a slight excess of methylacrylate which was removed by distillation before the MeOH and the R-(+)-phenethylamine addition.

Preparation PP8

Reductive amination of (2a) with t-butyl carbamate to form (11a)

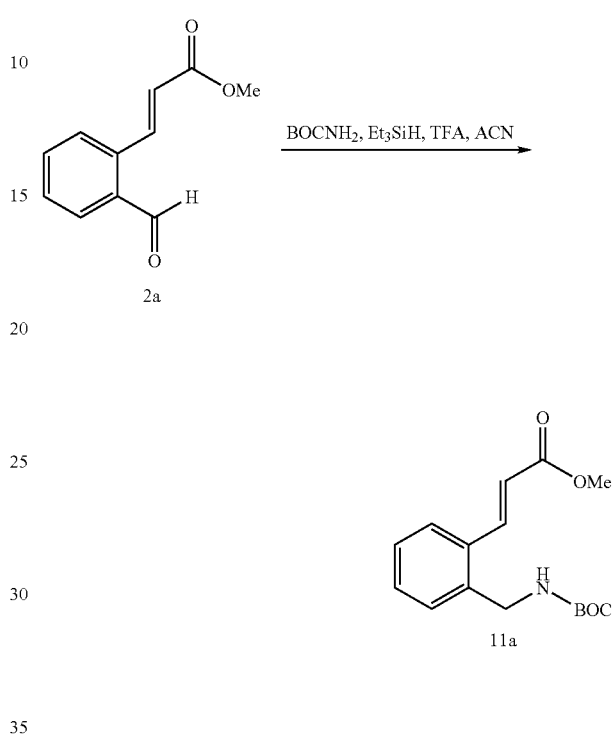

To a solution of aldehyde 2a (238 mg, 1.25 mmol) in CH₃CN (8 mL) was added t-butyl carbamate (439 mg, 3.75 mmol), followed by triethylsilane (0.6 mL, 3.75 mmol) and TFA (0.19 mL, 2.5 mmol). The mixture was stirred at rt overnight, quenched with sat. NaHCO₃ solution (20 mL) and extracted with EtOAc (2×30 mL). The combined organic layers were washed with brine (30 mL), dried (Na₂SO₄) and concentrated. The residue was purified by flash chromatography (hexane/EtOAc 3:1) to provide 317 mg (87%) of 11a.

Preparation PP9

Reductive amination of 2b with t-butyl carbamate to form 11b

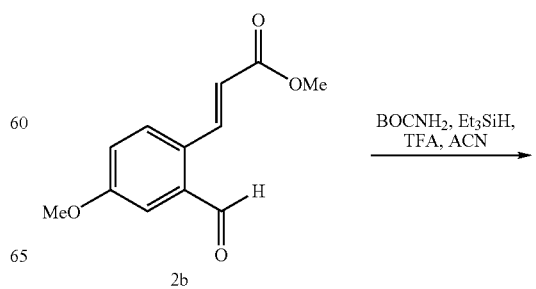

-continued

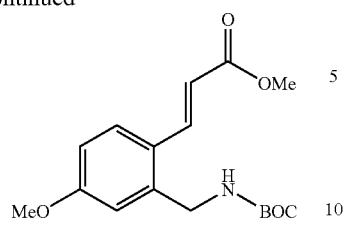

11b

A mixture of aldehyde 2b (600 mg, 2.72 mmol) Et₃SiH (955 mg, 3 eq, 1.31 mL), TFA (620 mg, 2 eq, 420 uL), t-butyl carbamate (980 mg, 3 eq) in acetonitrile (15 mL) was stirred at room temperature over 2 days. Removed the solvent on a Rotary evaporator and purified the crude residue on a flash column (100 g SiO₂, 7:1→6:1 Hex/EtOAc). Collected 307 mg good desired product 11b (35%); 195 mg product contaminated with aldehyde SM (22%).

Preparation PP10

Reductive amination of (2c) with t-butyl carbamate to form (11c)

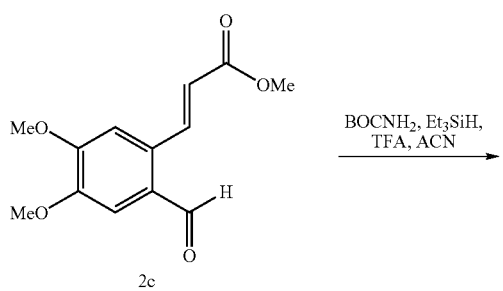

To a solution of aldehyde 2c (411 mg, 1.64 mmol) in CH₃CN (10 mL) was added t-butyl carbamate (580 mg, 4.93 mmol), followed by triethylsilane (0.8 mL, 4.93 mmol) and TFA (0.25 mL, 3.28 mmol). The mixture was stirred at rt overnight, quenched with sat. NaHCO₃ solution (30 mL) and extracted with EtOAc (2×30 mL). The combined organic layers were washed with brine (30 mL), dried (Na₂SO₄) and concentrated. The residue was purified by flash chromatography (hexane/EtOAc 3:1, hexane/EtOAc 1:1) to provide 535 mg (93%) of 11c.

Preparation PP11

Synthesis of 14d

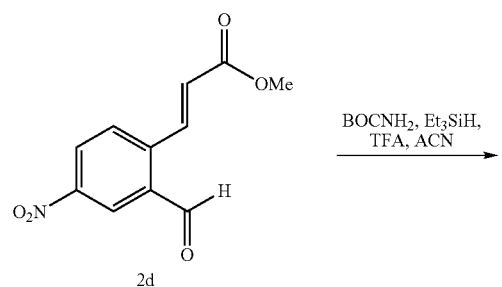

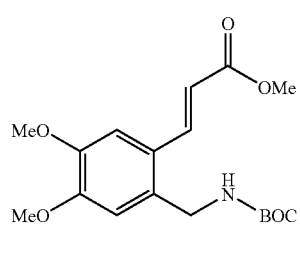

14d

To a solution of 2d (1.02 g, 4.34 mg) in CH₂Cl₂/CH₃CN (1:1 24 mL) was added BocNH₂ (1.5 g, 13.02 mmol), Et₃SiH (2.1 mL, 13.02 mmol), and TFA (0.67 mL, 8.67 mmol). The mixture was stirred at rt for 7 h. A precipitate was formed during the reaction. The reaction mixture was quenched with sat. NaHCO₃ solution (30 mL), and diluted with CH₂Cl₂ (40 mL). The organic layer was washed with brine (30 mL), dried (Na₂SO₄), and concentrated. The residue was purified by flash chromatography (hexane/EtOAc 3:1, then CH₂Cl₂/EtOAc 10:1) to provide 2.08 g yellow solid which still containing BocNH₂. The product is not the desired Boc-carbamate 14d. LC-MS result showed that the product is the Schiff base intermediate.

To the above product (420 mg) in CH₂Cl₂ (10 mL) was added Et₃SiH (1 mL) and TFA (0.4 mL). The mixture was stirred at rt for 1 h and small amount of sample was taken for NMR. NMR analysis demonstrated that the starting material was consumed and the product was 14d. TFA (0.7 mL) was then added to the above mixture and the resultant solution was stirred at rt for another 5 h and concentrated. The residue was dissolved in EtOAc (20 mL) and washed with H₂O (10 mL). The aqueous layer was basified with sat. NaHCO₃ (30 mL) and the organic compounds were extracted with CH₂Cl₂ (2×25 mL). The combined organic layers were washed with brine (20 mL), dried (Na₂SO₄) and concentrated to provide 218 mg of the cyclized compound 14d.

Preparation PP12

Condensation of 2a with -Methylbenzylamine to Form Imine 9

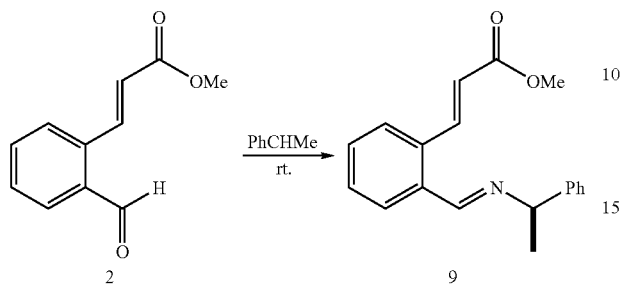

2-carboxaldehyde-methyl-cinnamate 2a (0.897 g, 4.72 mmol) was dissolved in MeOH (10 mL) at RT. R-(+)-phenethylamine (0.577 g, 4.76 mmol) was added and the solution was heated under reflux for 2 hours. HPLC In process control indicated that the imine formation was completed. The solvent was stripped on a rotary evaporator and the resulting oil was dried at RT under vacuum overnight. The Schiff base 9 was obtained almost quantitatively (1.412 g, 4.81 mmol).

Preparation PP13

Michael Addition

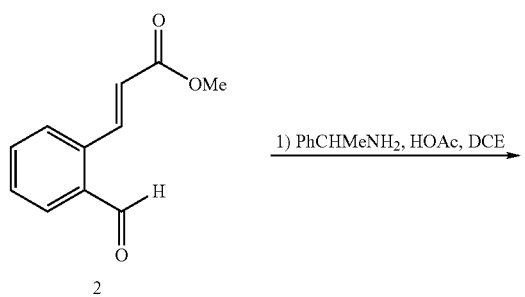

-Methyl benzylamine was applied as the auxiliary. As shown above, the one-pot reaction of aldehyde 2a and -Methyl benzylamine gave 90% of 10b with a ratio of 1.2:1.

Step-wise reduction, amination, and cyclization:

Condensation of aldehyde 2a with -methylbenzylamine in acetonitile or toluene afforded imine 9 in excellent yield. Reduction of the imine was initially carried out at RT with NaCNBH$_3$/HOAc. As a result, a poor ee ratio (1.2:1) was obtained, similarly to the previous described one-pot procedure. But when the reaction was carried out with NaBH$_4$/TFA at RT, the ratio was elevated to 2:1. By lowering the reaction temperature to −78° C., the ratio was increased to 5-6:1.

| Conditions | Ratio |
| --- | --- |
| NaCNBH$_3$, HOAc, rt | 1.2:1 |
| NaBH$_4$, TFA, rt | 2:1 |
| NaBH$_4$, TFA, −78° C. | 5-6:1 |

Preparation PP14

Cyclization of t-butyl carbamate (11a)

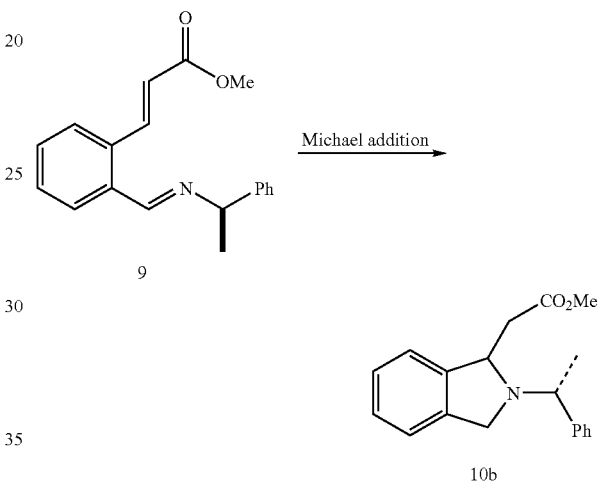

The N-Boc isoindoline methyl ester 12 was originally synthesized from 11a via deprotection of Boc with TFA, followed by basic workup, and protection with a Boc group. This procedure has been greatly improved by a one-step procedure.

Preparation PP15

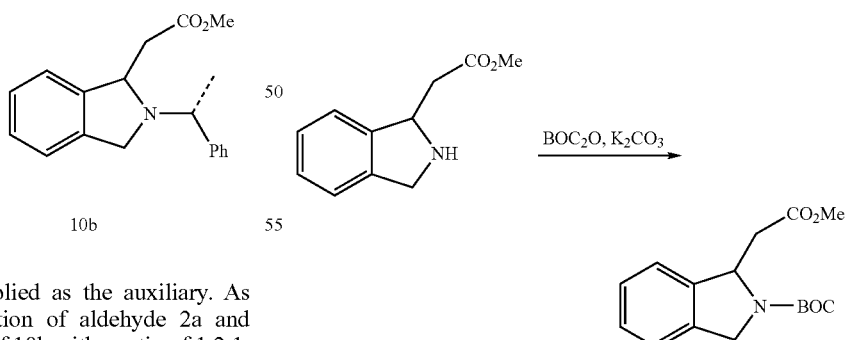

In a 3 L 3-neck round bottom flask equipped with a nitrogen inlet, thermocouple and mechanical stirrer, a solution of 160 g (1.15 moles) of K$_2$CO$_3$ in 180 mL of water was stirred at rt. Solid BOC anhydride 120 g (0.55 moles) was added in one portion forming a semi-solution. To the reaction mixture, a solution of the crude amino ester starting material, 87 g (0.46 moles) in 120 mL of THF was added slowly at such a rate to keep the internal temperature below 35° C. A mild effervescence was observed. The reaction mixture was stirred for 18 hours at rt. Analysis of a reaction aliquot via NMR (DMSO$_6$) indicates the desired product. The reaction was diluted with brine and the product extracted with EtOAc. The organic layer was dried over Na$_2$SO$_4$, filtered, and concentrated to yield a dark oil, 150.1 g, >100% yield. The crude material was taken on to the next step.

Preparation PP16

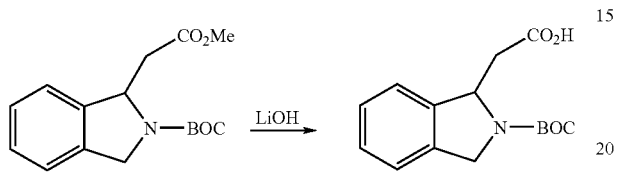

In a 3 L 3-neck round bottom flask equipped with a mechanical stirrer, thermocouple, and reflux condenser, a solution of 150 g (approx. 0.46 moles) of crude N-BOC ester starting material in 750 mL of methanol was stirred at rt. To the solution, 750 mL of water was added and the cloudy mixture was stirred vigorously. Solid LiOH 25 g (1.03 moles) was added in small portions at such a rate to maintain the internal temperature below 45° C. Upon completion of addition, the reaction was stirred overnight at rt becoming a dark green color. After 18 hours the reaction was concentrated to yield a thick semisolid. The crude product was dissolved in EtOAc and washed with 1 N HCl quickly, followed by two brine washes. The organic layer was dried with Na$_2$SO$_4$, filtered and concentrated to yield 81 g of a dark green solid. The aqueous layers were combined and back extracted with methylene chloride, dried over Na$_2$SO$_4$, filtered, and concentrated to yield 6 g of a dark green solid. Both solids were combined to yield 87 g of desired product confirmed via NMR (DMSO$_6$).

Preparation PP17

Synthesis of 14b

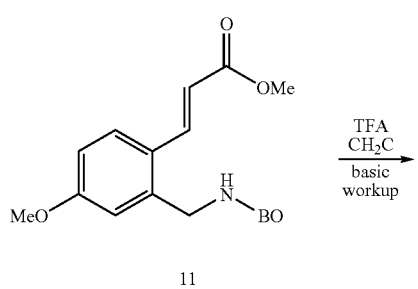

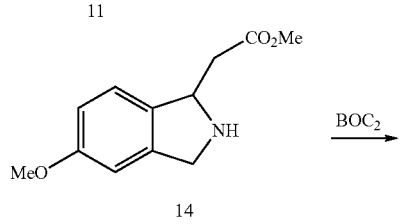

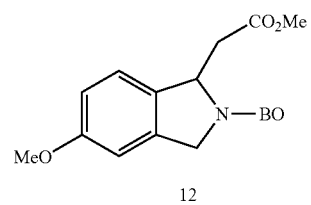

Dissolved the N-boc compound 11b (200 mg, 0.62 mmol) in CH$_2$Cl$_2$ (1.0 mL). Cooled the clear light yellow solution to 0° C. Added slowly TFA (~710 mg, 10 eq, 500 µL) via a syringe. Removed the cooling bath and stirred the clear light brown solution at RT overnight. TLC (3:1 Hex/EtOAc, UV) confirmed a complete reaction. Removed the TFA on a rotavapor. Added EtOAc and concentrated again (twice). The crude residue was partitioned between EtOAc (10-15 mL) and a sat. NaHCO$_3$ (10-15 mL). The aqueous was extracted with EtOAc (2×10 mL). The combined organic was dried over MgSO$_4$, filtered, and concentrated to yield a light brown wet solid (212 mg, 138%). NMR (CD$_3$OD) confirmed the desired isoindoline 14b. This crude isoindoline was used in the next protection step without purification.

Preparation PP18

Synthesis of 12b

To a mixture of the isoindoline 14b (190 mg, 0.859 mmol), K$_2$CO$_3$ (189 mg, 1.5 eq) in a solvent 1:1 THF/H$_2$O (1.0 mL) at RT was added BOC$_{20}$ (210 mg, 1.1 eq). The reaction mixture was stirred at RT overnight. TLC (3:1 Hex/EtOAc, UV) confirmed a complete reaction. Diluted the mixture with EtOAc (15 mL), and washed with H$_2$O (1×20 mL). The aqueous was extracted with EtOAc (1×20 mL). The combined organic was washed with brine (1×20 mL), dried over MgSO$_4$, filtered, concentrated to yield a clear brown oil (340 mg, 123%). This crude oil was purified on a prep TLC plate (2×1,000 micron, solvent 2:1.5:0.5 CHCl$_3$/Hex/EtOAc) to yield 12b a clear yellow oil (190 mg, 69%). $^1$H and $^{13}$C NMR (CDCl$_3$) were obtained.

Procedure PP19

Synthesis of 12d (5-NO$_2$) by Boc-protection

The procedure is same as that of 12b.

Preparation PP20

Synthesis of 10b

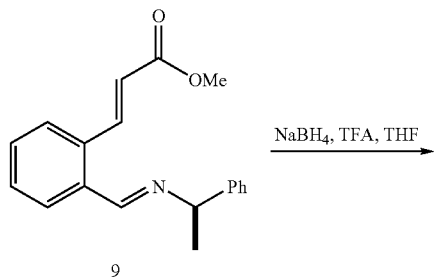

9

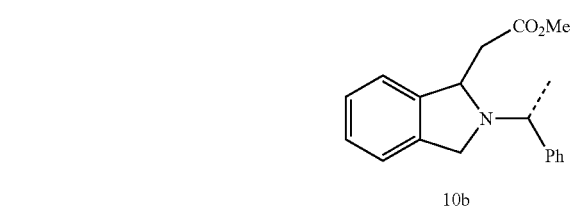

10b

The imine 9 (1.412 g, 4.81 mmol) was dissolved in anhydrous THF (10 mL) at RT and TFA (5 mL) was added. The black solution was then cooled to −78° C. (dry ice bath) and NaBH$_4$ (0.893 g, 23.6 mmol, 5 eq.) was added in 2 portions over 5 minutes. Then, the reaction mixture was post-agitated at −78° C. for 3 hours and allowed to gently warm at RT overnight. Water (20 mL), cyclohexane (10 mL) and EtOH (20 mL) were successively added and the organic layer was extracted and discarded. The aqueous layer was made basic with 5N NaOH (20 mL) and extrated two times with a 2:1 EtOAC/PhCH$_3$ mixture (30 mL). The combined organic layers were dried over MgSO4, filtered and rinsed with EtOAc (10 mL). The filtrates were concentrated under reduced pressure and the residual oil was dried under vacuum overnight at RT to afford the target cyclized isoindoline product 10b (1.273 g, 4.31 mmol) with 91.4% yield. HPLC % area indicated that the 2 diastereomers were produced in a 84:16 ratio (de 68%). $^1$H NMR confirmed this result by integration of the methyl group of the phenethyl substituent.

Preparation PP21

Cyclization of (11a)/Formation of (12a)

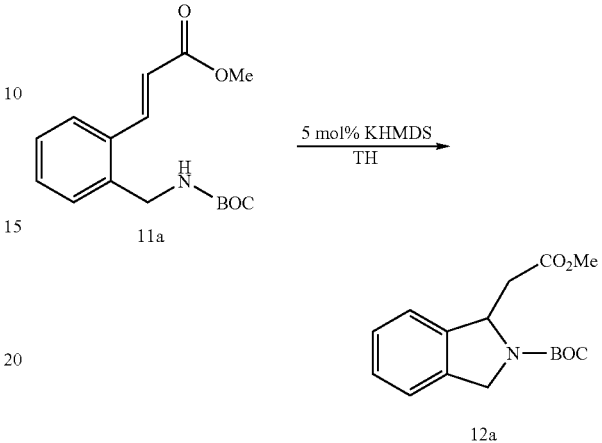

Dissolved the N-Boc methyl ester 11a (36.3 g, 0.125 mol) in THF (250 mL). Cooled the solution to 0° C. Added slowly a solution of potassium bis(trimethylsilyl)amide (1.24 g, 0.05 mol. Eq.) via a syringe under nitrogen atmosphere. The temperature was raised about 8 degrees during the addition. Removed the cooling bath and stirred the clear brown solution at room temperature for 30-45 min. TLC (3:1 Hex/EtOAc) confirmed a complete reaction. Poured the clear brown solution into a separation funnel containing about 100 mL of a saturated NH$_4$Cl and a few crushed ice. The layers were separated. The aqueous layer was extracted with EtOAc (2×50 mL). The combined organic was washed with brine (1×100 mL), dried over Na$_2$SO$_4$, filtered, concentrated on a Rotary evaporator to a clear yellow oil (37.3 g). This crude oil was purified on a flash column (600 g SiO$_2$), with a gradient solvent 6:1 Hex/EtOAc (2.1 L), 5:1 Hex/EtOAc (1.2 L), 4:1 Hex/EtOAc (1.5 L) to yield 12a as a clean yellow oil (34.5 g, 95%).

Preparation PP22

Cyclization of (11c). Formation of (12c)

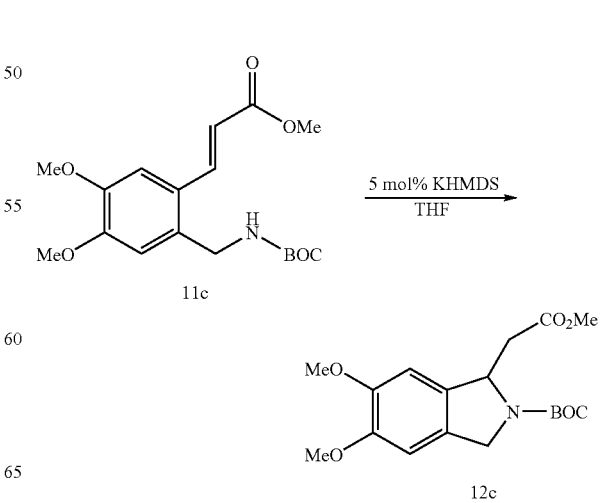

To a solution of 11c (535 mg, 1.52 mmol) in THF (10 mL) was added KHMDS (0.5 M in toluene, 0.1 mL, 0.05 mmol, 2 mol %). The mixture was stirred at rt for 20 min, quenched with sat. NH$_4$Cl solution (20 mL), and diluted with EtOAc (20 mL). The organic layer was separated, washed with brine (20 mL), dried (Na$_2$SO$_4$), and concentrated. The residue was filtered through a plug of silica gel (EtOAc/CH$_2$Cl$_2$ 1:10) to give 530 mg (99%) of 12c as an off white soild.

Preparation PP23

Hydrogenolysis of 10a (R=Bn) to Form (14a)

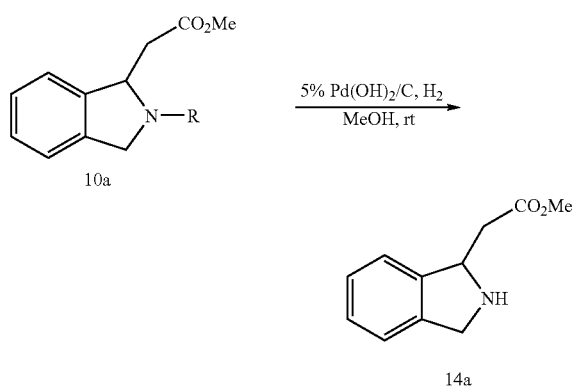

Deprotections:

To a solution of crude 10a (15.3 g, 54.4 mmol) in MeOH (100 mL) was added Pd(OH)$_2$/C (Pearlman's catalyst, 1.02 g, 6 mol %) in a par-shaker bottle. The suspension was shaken under 30 psi H$_2$ pressure overnight in the par-shaker, and filtered through a plug of celite. The filtrate was concentrated to provide 10.1 g of crude 14a as brown oil. (The procedure is same for the methyl benzylamine isoindoline substrate 10b).

Preparation PP24

Hydrolysis of Isoindoline Methyl Ester (12a). Formation of Isoindolinecarboxylic Acid (16a)

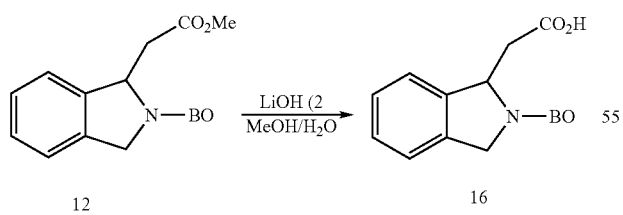

In a typical reaction a mixture of the isoindoline ester 12a (92 mg, 0.316 mmol) in 1:1 MeOH/H$_2$O (2 ml) was treated with LiOH (15 mg, 2 eq) at RT overnight. Diluted the mixture with CH$_2$Cl$_2$ (5 ml) and water (5 ml). Adjusted the pH of the reaction mixture to 1-3 with a 10% NaHSO$_4$ solution. Separated the layers. The aqueous was extracted with CH$_2$Cl$_2$ (1×10 ml). The combined organic was dried over Na$_2$SO$_4$, filtered, concentrated to yield 16a as a pale yellow foam (76 mg, 87%). NMR (CDCl$_3$) showed a clean desired acid product.

Note: 1. Rreaction time must be more than 6 hours.
2. The crude foam can be purified by slurry in warm hexane and then filter to yield a tan solid.
3. Hydrolysis using KOH (2-5 eq) in 1:1 MeOH/H$_2$O overnight will give the same result.

Preparation PP25

Purification of Partially Resolved Isoindolinecaboxylic Acid Methyl Ester

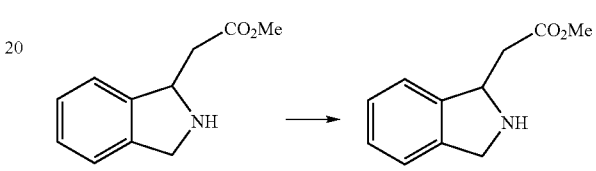

Resolution:

A solution of the crude material (97.62 g) isoindolinecaboxylic acid methyl ester in CH$_2$Cl$_2$ (350 mL) was extracted with 1M HCl (400 mL, 200 mL). The combined aqueous portions were washed with CH$_2$Cl$_2$ (4×250 mL) and then made basic with K$_2$CO$_3$ solution (85 g in 150 mL of water). The mixture was extracted with CH$_2$Cl$_2$ (6×100 mL) and the combined organic extracts were dried (Na$_2$SO$_4$) and concentrated to give partially resolved Isoindolinecaboxylic acid methyl ester as an oil (33.2 g). 60% ee by chiral CE.

Preparation PP26

Resolution of Partially Resolved Isoindolinecaboxylic Acid Methyl Ester

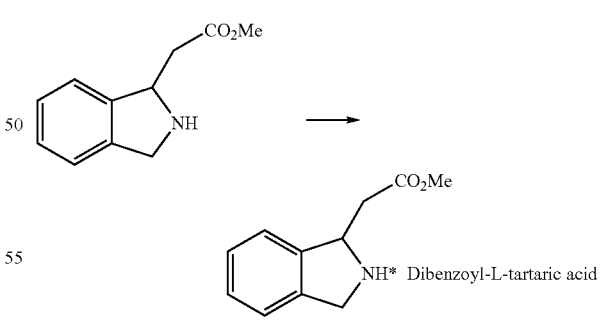

A solution of partially resolved isoindolinecaboxylic acid methyl ester (33.24 g, 0.174 mol) in EtOH (130 mL) was treated slowly with a solution of dibenzoyl-L-tartaric acid (56.06 g, 0.156 mol) in EtOH (200 mL). The solution was seeded with seeded with product and stirred at RT for 4 hours. Pure product was collected by filtration, washed with EtOH (30 mL) and dried to off-white crystals (60.49 g). 96.5% ee by chiral CE.

Preparation PP27

Resolution of N-BOC Isoindolinecaboxylic Acid

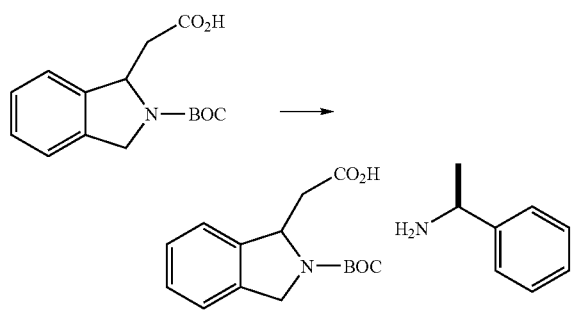

A solution/slurry of racemic N-BOC Isoindolinecaboxylic acid (114.5 g, 0.413 mol) in EtOAc (1000 mL) was treated slowly with triethylamine (28.8 mL, 0.206 mol), followed by (S)-(−)-α-methylbenzylamine. The solution was seeded with product and stirred at RT overnight. Product was collected by filtration, washed with EtOAc (200 mL) and dried to a white powder (62.98 g). 97.6% ee by chiral CE.

Preparation PP28

Part I. Synthesis of the Z-isomer (precursor of asymmetric hydrogenation)

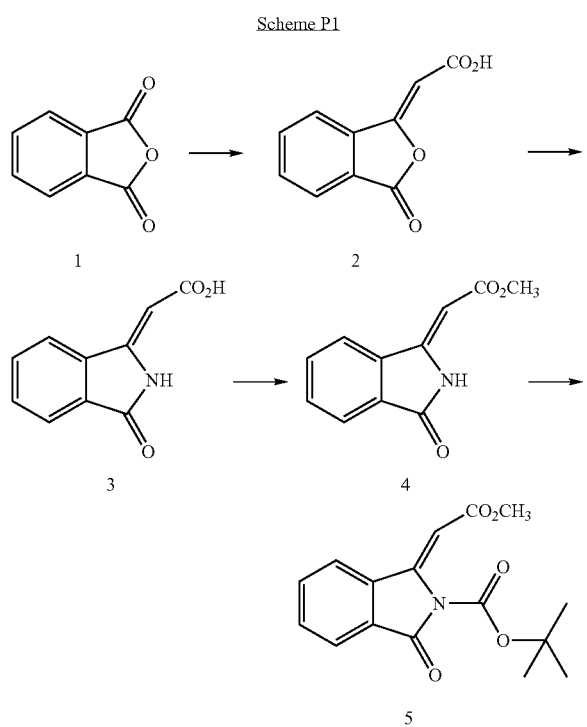

Asymmetric Hydrogenation Routes:

Z-isomer 5 was synthesized as outlined in Scheme P1. Compound 5 was shown to be a single isomer by HPLC and H-1 nmr. The double bond stereochemistry was derived from comparative NOE data using the purported E-isomer (Scheme P1). The best chiral induction was achieved using compound 8/Ferrotane/MeOH-THF. With regard to the conversion of 9 to 10, which would constitute a formal asymmetric synthesis of isoindolene 10, this has been achieved using Super hydride-$BF_3.OEt_2$. However, the product was a mixture of 10 and the corresponding de-BOC (deprotected) compound.

Preparation PP29

Compound 2 (Scheme P1)

Phthalic anhydride (751.5 g, 5.014 mole), potassium acetate (498 g, 5.014 mole) and acetic anhydride (1 L) were stirred together under nitrogen. The mixture was slowly warmed to 145-150° C. and stirred for 10 minutes, then at 140° C. for 20 minutes. The mixture was allowed to slowly cool to 80° C. over 1 hour. Three volumes of water were added causing precipitation of a solid. After filtration, the filtered solid was washed with warm water and pulled as dry as possible for 30 minutes. The solid was then washed with ethanol and acetone respectively. If required further purification could be achieved by slurrying the solid in acetone, at room temperature, for 15 minutes, then filtration. Drying in vacuo at 50° C. for 20 hours gave compound 2 as an off-white solid, 470 g (48%) with an NMR purity of approx. 90%.

Preparation PP30

Compound 3 (Scheme P1)

Compound 2 (470 g, 2.47 mole) was added to stirred aqueous ammonia (470 ml conc. $NH_3$ in 4.7 L water). The resultant mixture was stirred at room temperature for 1 hour then filtered. The filtered solid was washed with water. The combined aqueous filtrate and washings were carefully acidified with 6M aq. HCl (2.35 L). The precipitate was removed by filtration and dried in vacuo at 50° C. to give compound 3 as a yellow solid, 259 g (52%).

Preparation PP31

Compound 4 (Scheme P1)

Compound 3 (511 g, 2.7 mole) was slurried in toluene (10 vol). Thionyl chloride (385 g, 3.24 mole) was added over 10 minutes to the stirred mixture, which was then heated to reflux for 1.5 hours. H-1 NMR analysis indicated approx. 80% conversion to acid chloride). DMF (3.7 ml) was added and the mixture refluxed an additional 3 hours. The resultant mixture was allowed to cool to 35° C. and methanol (1.27 L) added at such a rate that the reaction temperature was maintained at 30-35° C. The reaction mixture was kept at this temperature a further 15 minutes then concentrated in vacuo to give compound 4 as a brown solid, 536 g (quantitative).

Preparation PP32

Compound 5 (Scheme P1)

Compound 4 (750 g, 3.65 mole) was dissolved in acetonitrile (15 L). The stirred mixture was cooled to 0-5° C. and DMAP (624 g, 5.11 mole) added in one portion. After 10 minutes BOC anhydride (1115 g, 5.11 mole) was added in one portion: there was a slight exotherm accompanied by gas evolution. The mixture was stirred at room temperature for 5 hours, and then concentrated in vacuo. The residue was dissolved in EtOAc and washed with 10% aqueous citric acid, satd. aq. $Na_2CO_3$ and water respectively. After drying, concentration of the organics gave a thick syrup. This material was run through a plug of silica gel (1.5 kg) eluting with 1:1 EtOAc-hexane. Compound 5 was isolated as a dark solid, 619 g (55%). Careful chromatography on silica gel eluting with 20% EtOAc-hexane gave 5 as a fluffy white solid.

Preparation PP33

Part II. Synthesis of the E-isomer (precursor of asymmetric hydrogenation)

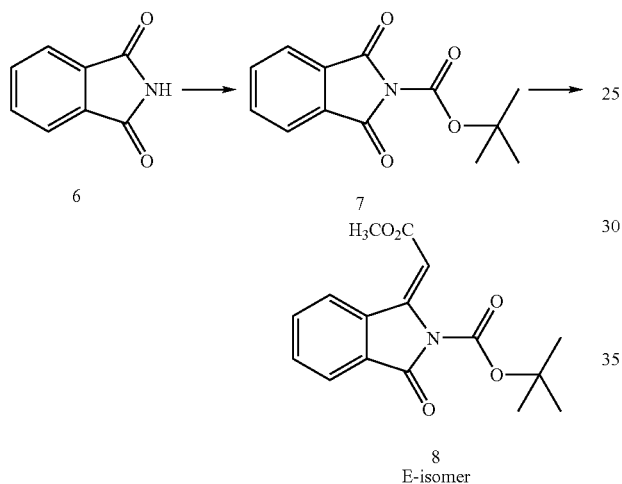

The E-isomer of Compound 8 (Scheme P2), was prepared as shown in Scheme P2.

Preparation PP33

Compound 7 (Scheme P2)

Compound 7 was prepared according to the procedure of Einhorn et al, *Synth. Commun.* 2001, 31(5), 741-748.

Preparation PP34

Compound 8 (Scheme P2)

Compound 7 (15.00 g, 60.7 mmole) and methyl(triphenylphosphoranylidene)acetate (41.40 g, 121.3 mmole) were slurried in toluene (150 ml). The mixture was stirred at reflux and monitored for reaction of 7 by GC. After 1.5 hours the reaction appears complete by GC. After cooling to room temperature, the mixture was filtered. The solid on the filter was washed with toluene until colorless. The combined filtrate/washings were concentrated in vacuo to leave a tan solid. This material was coated on silica gel and chromatographed on silica gel (1 kg) eluting with 10% EtOAc-hexane. Compound 8 was isolated as a white or pale yellow powder, 5.52 g (30%).

Asymmetric Hydrogenation:

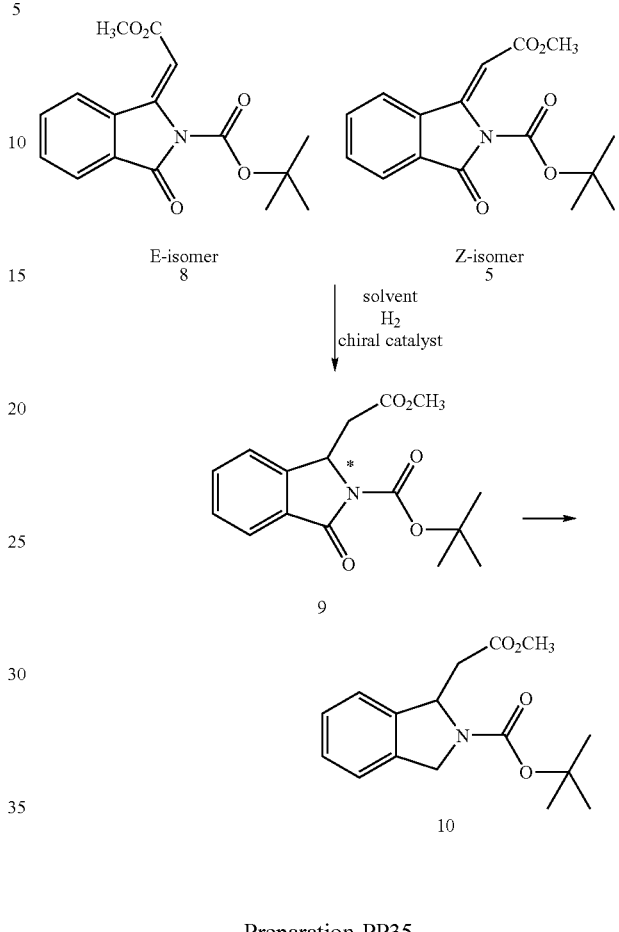

Preparation PP35

Screening of chiral hydrogenation conditions indicated that the best chiral induction was achieved using compound 8/Ferrotane/MeOH-THF. With regard to the conversion of 9 to 10, which would constitute a formal asymmetric synthesis of isoindolene 10, this has been achieved using Super hydride-$BF_3.OEt_2$. However, the product was a mixture of 10 and the corresponding de-BOC (deprotected) compound.

Coupling of chiral isoindoline with d-4-chloro-phenylalanine:

(Using Tartrate Salt)

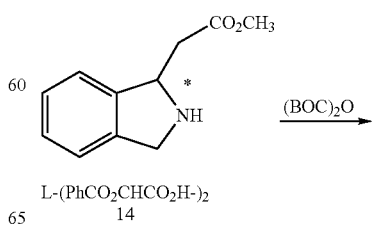

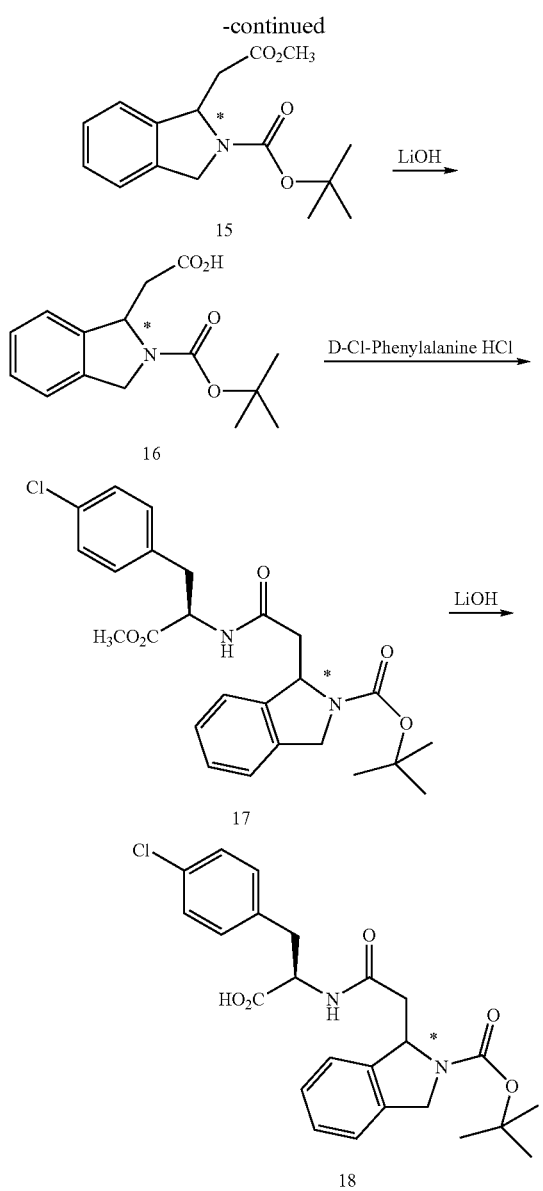

Preparation PP37

Compound 16 (Scheme P4)

Ester 15 (29.21 g, 100.26 mmole) was dissolved in 3:1 THF-water (100 ml). LiOH (6.00 g, 250.65 mmole) was added in 1 portion to the stirred solution. After 17 hours, the mixture was stripped to dryness and the residue dissolved in water (500 ml). EtOAc (250 ml) was added and solid $NaHSO_4$ added to the stirred mixture until the pH=3. The organic layer was separated and the aqueous layer extracted with EtOAc (250 ml). The combined EtOAc layers were dried ($MgSO_4$). Filtration and concentration in vacuo gave acid 16 as a light tan solid, 27.10 g (97%).

(From alpha-methyl benzylamine salt):

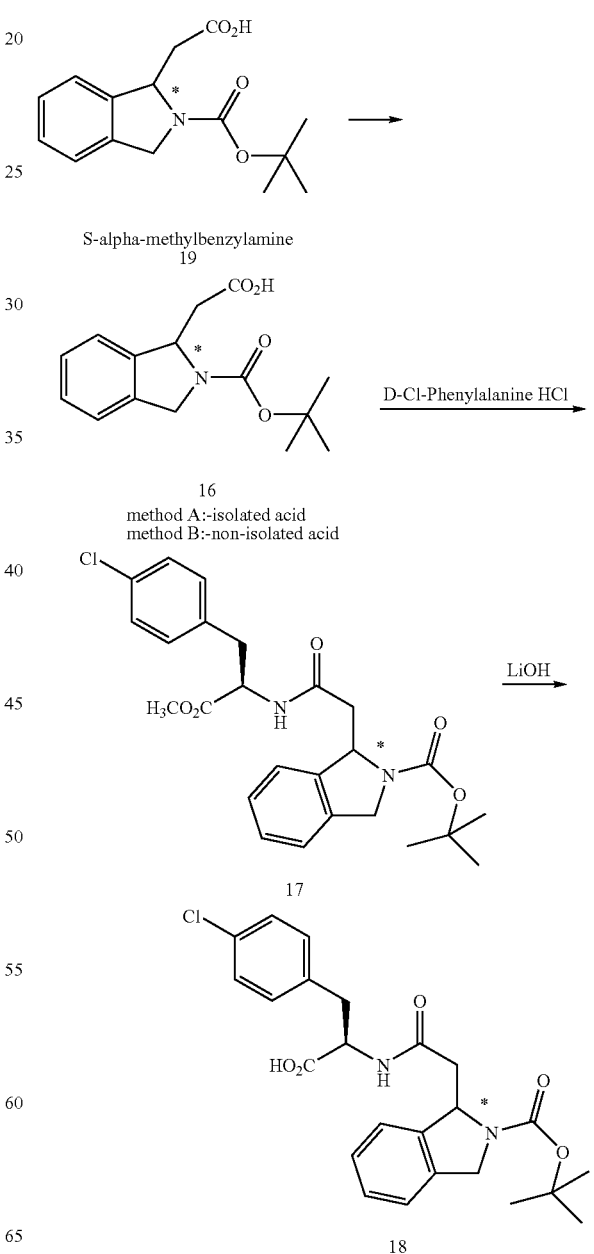

Preparation PP36

Compound 15 (Scheme P4)

Tartrate salt 14 (58.00 g, 100.27 mmole) was slurried in water (580 ml). Solid $NaHCO_3$ (25.27 g, 300.8 mmole) was carefully added. BOC anhydride (22.98 g, 105.28 mmole) was added in one portion and the progress of the reaction monitored by reverse phase HPLC. After 1 hour additional BOC anhydride (2.18 g, 10.00 mmole) was added. The reaction was complete (by HPLC) after 3 hours. The mixture was extracted with EtOAc (2×250 ml). The combined organic extracts were washed with water (250 ml) and dried ($MgSO_4$). Filtration and concentration in vacuo gave 15 as a clear light brown oil (31.33 g) contaminated with a small amount of t-BuOH and BOC anhydride. This material was used directly in the next reaction.

The chemistry used is shown in Scheme P5. Two protocols were used: method A used isolated 16, method B used a solution of 16 derived from resolved salt 19.

Preparation PP38

Compound 17 (Scheme P5, method A)

Acid 16 (24.18 g, 87.2 mmole) and D-chloro-phenylalanine hydrochloride (21.81 g, 87.2 mmole) were dissolved in CH$_2$Cl$_2$ (100 ml) and DMF (25 ml). The mixture was stirred at ambient temperature. HOBT (13.55 g, 100.3 mmole) and Hunig's base (45.6 ml, 33.81 g, 261.6 mmole) were added. HATU (38.13 g, 100.3 mmole) was added in 1 portion (there was a rapid exotherm to 50° C.). The mixture was stirred for 90 minutes then diluted with EtOAc (750 ml). The resulting mixture was washed with water, 5% KHSO$_4$, brine and satd. NaHCO$_3$ respectively, then dried. Filtration and concentration in vacuo gave crude 17 as a brown foam. The product was purified by chromatography on silica gel (1 kg) eluting with 1:1 EtOAc-hexane. Ester 17 was isolated as a tan powder, 38.85 g (94%).

Preparation PP39

Compound 17 (Scheme P5, Method B)

Resolved salt 19 (96.27 g, 232.5 mmole) was partitioned between water (500 ml) and CH$_2$Cl$_2$ (250 ml) Solid KHSO$_4$ was added portion wise until pH=2.5. Separate the organic layer and extract the aqueous layer with CH$_2$Cl$_2$ (150 ml). The combined organic layers were dried (MgSO$_4$) then filtered. To this solution was added 4-chloro-D-phenylalanine (58.16 g, 232.5 mmole), HOBT (34.57 g, 255.8 mmole), Hunig's base (93.2 ml, 69.13 g, 534.9 mmole) and finally HATU (97.26 g, 255.8 mmole). The resultant mixture was stirred at room temperature for 18.5 hours, and then poured onto a plug of silica gel (1 kg). This was washed with 1:1 EtOAc-hexane until no more product elutes. Ester 17 was isolated as a pink foam, 101.79 g (93%): contains about 1% unreacted 16.

Preparation PP40

Compound 18 (Scheme P5)

Ester 17 (38.64 g, 81.7 mmole) was dissolved in 3:1 THF-water (200 ml). LiOH (2.15 g, 89.9 mmole) was added to the mixture, which was stirred at room temperature for 2 hours. The solvent was then removed in vacuo and the residual solid taken up in water (600 ml). This was extracted with MTBE (250 ml). The aqueous layer was separated and stirred with EtOAc (250 ml), and solid KHSO$_4$ was added portion wise until pH=3. The layers were separated and the aqueous extracted with EtOAc (250 ml). The combined organic layers were dried over MgSO$_4$. Filtration and concentration in vacuo gave acid 18 as a light pink foam, 38.41 g (35.71 g corrected for residual solvent, 95%).

Procedures for Preparing Isoquinoline Carboxylate Intermediates:

Preparation PP41

Step 1 Esterification:

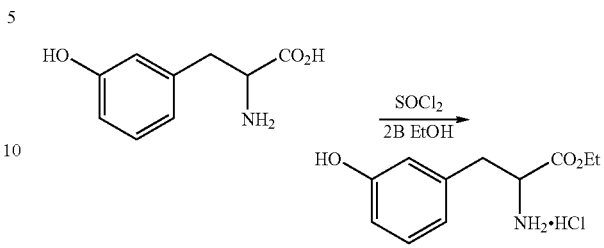

In a 22 L 4-neck round bottom flask equipped with a reflux condenser, thermocouple and nitrogen inlet, a slurry of 1000 g (5.4 moles) of m-tyrosine in 10 L of 2B-3 EtOH was cooled to 5° C. To the slurry, 350 mL (12.4 moles) of thionyl chloride were added dropwise via an addition funnel at such a rate to maintain the reaction temperature below 20° C. Upon completion of addition, the reaction was heated to reflux temperature and stirred for 18 hrs. The reaction was concentrated to one-third the volume and 8 L of MTBE were charged. The resulting thick slurry was stirred for 14 hrs in a rotary evaporator at rt. The resulting solid was isolated on a filter pad and dried at 40° C. for 48 his yielding 1288 g (95%). NMR (DMSOd$_6$) indicated desired material.

Preparation PP42

Step 2 Pictet-Spengler:

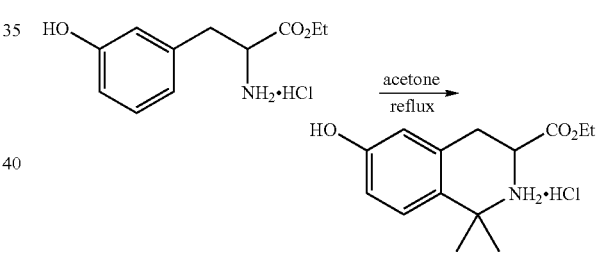

In a 22 L 4 neck round bottom flask equipped with a mechanical stirrer, thermocouple, and reflux condenser placed on top of a Soxhlet extractor charged with 4° A sieves, a semi-solution of m-tyrosine ethyl ester hydrochloride 1288 g (5.26 moles) in 13 L of acetone was heated to reflux temperature. The condensate was filtered through the sieves to remove water. The reaction was stirred vigorously at reflux for 48 hrs. An NMR sample in DMSOd$_6$ indicated the absence of starting material. The reaction was cooled to rt and concentrated to yield an off-white solid, 1411 g (94%).

Preparation PP43

Step 3 Triflation:

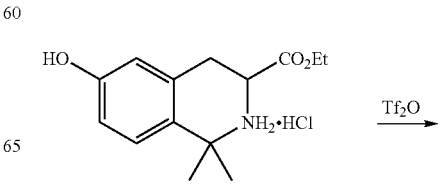

-continued

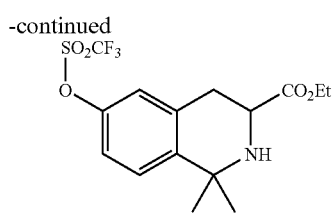

In a 22 L 4 neck round bottom flask equipped with a reflux condenser, mechanical stirrer, nitrogen inlet, and a thermocouple, 1240 g (4.35 moles) of the starting material salt in 12.4 L of methylene chloride was cooled to 4° C. To the mixture, 1452 mL (10.4 moles) of triethylamine were added and stirred into solution. Triflic anhydride, 1472 mL (5.22 moles) was added dropwise to the reaction at such a rate to maintain the internal temperature below 10° C. The ice bath was removed and the reaction warmed to rt. and stirred for 18 hrs. The reaction was concentrated to a oil then dissolved in 4 L of EtOAc and concentrated again to an oil in an effort to remove excess triflic anhydride The crude residue was dissolved in 4 L of EtOAc and washed with water and saturated sodium bicarbonate solution. The organic layer was isolated and dried with sodium sulfate, filtered and concentrated to yield 1720 g (>100%) of a crude dark oil which was used without further purification.

Preparation PP44

Step 4 Deoxygenation:

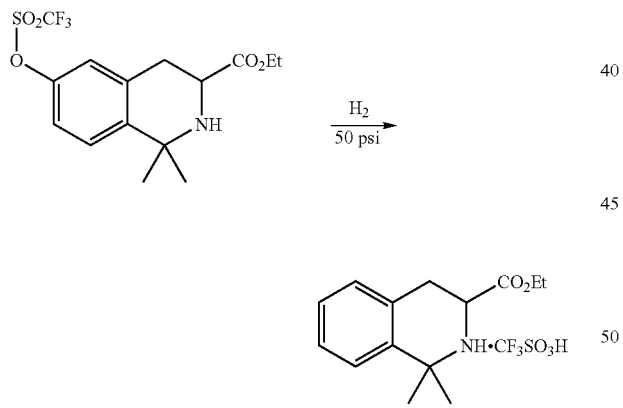

A solution of 1720 g (4.35 moles) of crude starting material in 14 L of acetone was charged to a 10 gallon stainless steel autoclave. To the solution, a slurry of 5% Pd/C in 1.2 L of toluene was added. The reaction mixture was evacuated and purged with $H_2$ gas at 50 psi two times. The reaction was stirred overnight at 50° C. with $H_2$ at 50 psi. A sample aliquot indicated no reaction had occurred. The mixture was filtered and concentrated to a thick oil and resubjected to reaction conditions. After 18 hrs, NMR of a sample aliquot indicated absence of starting material. The reaction mixture was filtered and the filtrate concentrated to yield 1581 g of an off-white solid (95%).

Preparation PP45

Step 5 Hydrolysis/Salt Formation:

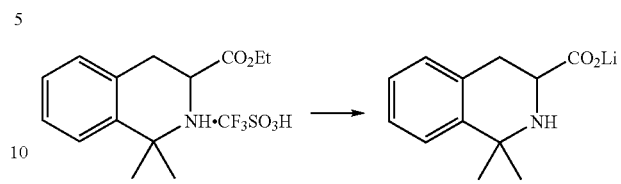

To a 2 L 3 neck round bottom flask equipped with a mechanical stirrer, thermocouple, and nitrogen inlet, a mixture of 700 g (1.83 moles) of the triflate salt starting material was charged. A solution of 427 g (1.83 moles) of the starting material free base in 13.3 L of THF was added followed by 700 mL of water. The semi-solution was stirred vigorously at rt. To the reaction flask, 43.7 g (1.83 moles) of solid LiOH were added in small portions at such a rate to maintain the internal temperature below 35° C. The reaction was stirred for 18 hrs at rt and concentrated to yield a thick oil. THF (4 L) was added and the semi-solution was concentrated. This was repeated with toluene and the semi-solid was placed under house vacuum on the roto vap with stirring for 18 hrs. to yield 650 g of a crude solid. The solid was reslurried in EtOAc, filtered, isolated and dried to yield 525 g (68%) of the lithium salt as an off-white solid.

Preparation PP46

Step 6 Coupling:

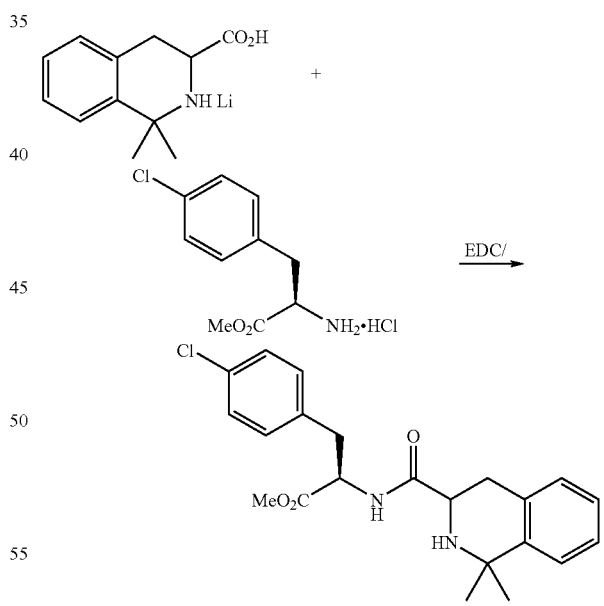

To a 12 L 4 neck flask equipped with a mechanical stirrer, water-cooled reflux condenser, thermocouple, and nitrogen inlet, a mixture of 400 g (1.62 mole) of the starting material free acid, 2 L of DMF, and 2 L of methylene chloride were stirred vigorously. Solid d-chloro-phenylalanine 446 g (1.78 moles) was added to the semi-solution followed by 20 g (0.162 moles) of DMAP. The resulting mixture was stirred for 15 minutes then solid EDCl (1-(3-dimethylaminopropyl)-3-ethylcarbodiimide hydrochloride) 390 g (2.03 moles)

was added. The reaction mixture was heated to 80° C. and stirred for 18 hours. Thin layer chromatography (1:1 EtOAc: Hex) indicated very little starting material present. The reaction was cooled to rt and concentrated to yield a thick oil. The crude oil was dissolved in EtOAc and washed with water, and brine. The solution was dried with sodium sulfate, filtered and concentrated to yield a thick oil, 426 g. The crude oil was chromatographed in several lots using a Waters Prep 500 chromatography apparatus. The eluent consisted of a gradient system, 5%-80% EtOAc in heptane at a flow rate of 240 ml/min over 38 minutes. The two diasteromers were separated and isolated to yield 119.04 g for the top spot and 111.3 g for the bottom spot. Conformation of both desired diastereomers was achieved via NMR (DMSO₆).

Preparation PP47

Resolution

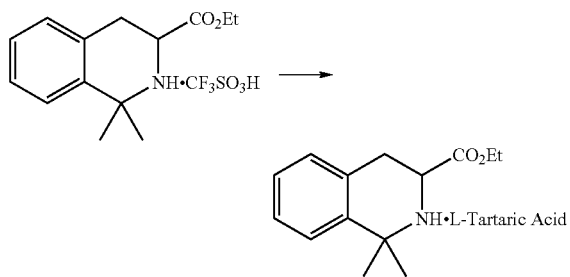

Resolution of Tetrahydroisoquinolinecarboxylic Acid Ethyl Ester to Prepare 1-tartaric Acid Salt:

Preparation of free-base: A racemic mixture of tetrahydroisoquinolinecarboxylic acid (7.43 g) in EtOAc (60 mL) was treated with saturated NaHCO₃ solution (60 mL) and saturated Na₂CO₃ solution (10 mL). The mixture was agitated and the layers were separarted. The organic phase was dried (Na₂SO₄) and concentrated to give the corresponding free-base as an oil (4.85 g).

Resolution: A mixture of the above free base (467 mg, 2.0 mmol), and L-tartaric acid (300 mg, 2.0 mmol) in acetone (4 mL) was stirred at RT overnight. The title L-tartaric acid salt was collected by filtration, washed with acetone (about 2 mL) and dried to a white powder (367 mg). 100% ee by chiral CE.

Preparation PP48

2-{2-[(tert-butyl)oxycarbonyl]-1,2,3,4-tetrahydroisoquinolyl}acetic acid dehydroabietylamine salt

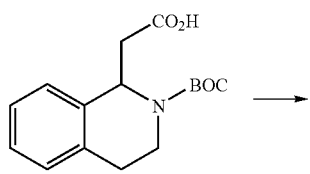

-continued

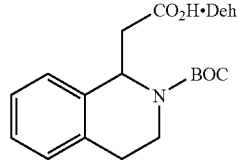

Resolution of N-BOC Tetrahydroisoquinolinecarboxylic Acid to Prepare:

Racemic 2-{2-[(tert-butyl)oxycarbonyl]-1,2,3,4-tetrahydroisoquinolyl}acetic acid (30.15 g, 103.5 mmol) was dissolved in i-PA (300 mL). Dehydroabietylamine (22.11 g, 52.7 mmol of a 68 weight % mixture) was added to the solution, which was then agitated on a multi-arm shaker for 63 h. The resultant thick paste was filtered and rinsed with i-PA (50 mL, 25 mL). Dried in a 50° C. vacuum oven to obtain a white solid (27.73 g, 52% ee by chiral CE analysis). The product was reslurried in i-PA (266 mL) and agitated on a multi-arm shaker for 23.5 h. Filtered the thick slurry and rinsed with cold i-PA (50 mL, 30 mL). Dried the cake in a 50° C. vacuum oven and obtained the product as a white solid (23.63 g, 40% yield, 94% ee by chiral CE analysis).

Preparation PP49

Scheme P6

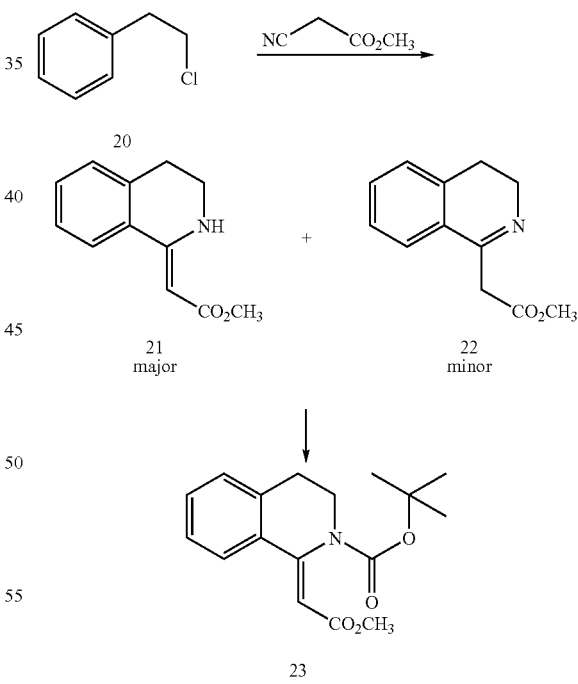

Asymmetric Hydrogenation:

Enamine 21 (Scheme P6) was prepared as a substrate for asymmetric hydrogenation screening studies. It is formed as an approx. 10:1 mixture with imine 22. The enamine (21) may be NH-protected i.e. by a Boc protecting group. The resulting compound 23 may be subjected to asymmetric hydrogenation to afford the acetic acid or methylacetate substituted isoquinoline, which may be processed into a compound of formula I as demonstrated previously.

Preparation PP50

Compound 21 (Scheme P6)

Prepared as published W Sobotka et al, *J. Org. Chem.*, 1965, 30, 3667.

Synthesis of Gem-dimethyl TIC

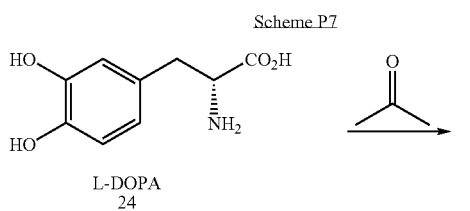

L-DOPA
24

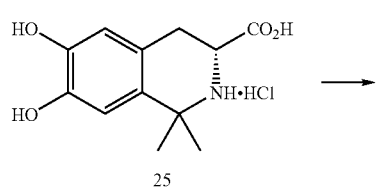

25

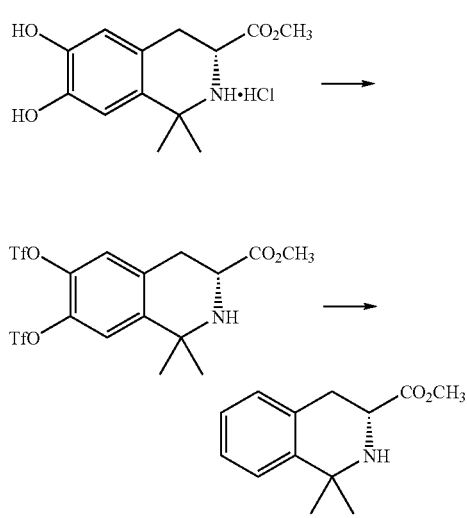

Preparation PP51

The chiral synthesis of gem-dimethyl TIC using L-Dopa as the starting material instead of tyrosine was successfully demonstrated up to the Pictet-Spengler reaction with L-DOPA and acetone. The product is a mixture of starting material 24 and product 25 (major component). The product was isolated by using common isolation procedures. An alternative isolation method is to react the mixture (24 and 25) with BOC anhydride wherein the less hindered N-H in 24 leads to preferential BOC protection of 24, allowing for ready separation of 25. Chemistry for the rest of the sequence has been demonstrated herein i.e. deoxygenation reaction, etc.

Preparation BC1

3-[2-(4-Chloro-phenyl)-1-methoxycarbonyl-ethyl-carbamoyl]-3,4-dihydro-1H-isoquinoline-2-carboxylic acid tert-butyl ester

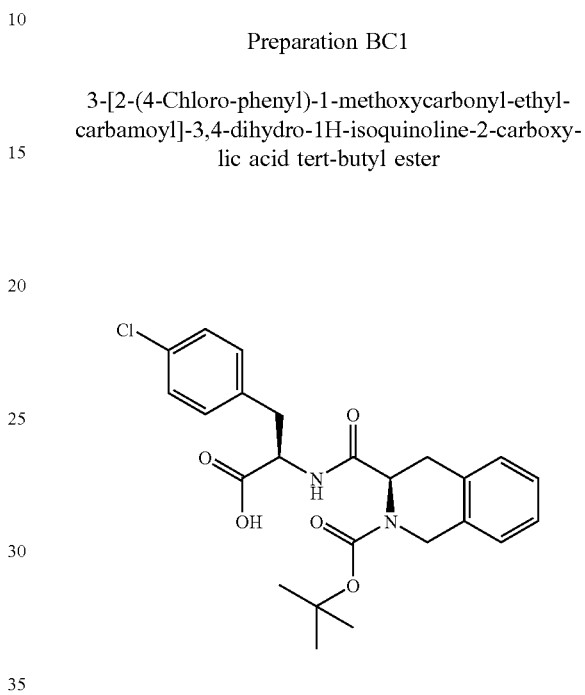

Preparation of Novel "B-C" Pieces:

A. To a 0° C. solution of 4-Chloro-D-Phe methyl ester (23.8 g, 111.0 mmol), Boc protected D-Tic (30.8 g, 111.0 mmol) and 4-DMAP (75 mg, 0.61 mmol) in 200 mL of DCM was added EDC (30.8 g, 111.0 mmol) and the mixture stirred for 20 minutes. The ice bath was removed and the mixture stirred at room temperature for 4 h. After washing with water (4×200 mL), the combined aqueous portions were back extracted with DCM (2×200 mL). The combined organic portions were washed with brine, dried ($MgSO_4$), and concentrated to dryness. The desired product was purified by flash chromatography ($SiO_2$, eluting with 35% EtOAc in Hexanes) affording 43.0 g (83%) of the ester. EIS MS 473 [M+1].

B. To the above-formed ester (43.0 g, 91.0 mmol), in MeOH (170 mL) at 0° C., was added 1N NaOH (227.0 mL, 227.0 mmol), dropwise. After 20 minutes the ice bath was removed and the mixture stirred at room temperature for 3 h. The mixture was concentrated to dryness, and the resulting residue suspended in 200 mL of water. The aqueous layer was made acidic (pH 1) with 5 N hydrochloric acid and extracted with EtOAc (4×200 mL). The combined organics were dried ($MgSO_4$), filtered, and concentrated to dryness, affording 39.0 g (93%) of the title compound. EIS-MS 459 [M+1].

Preparation C1

1-Methoxycarbonylmethyl-1,3-dihydro-isoindole-2-carboxylic acid tert-butyl ester

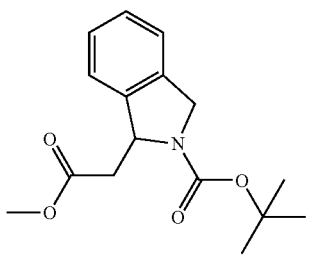

A. (2-Bromo-benzyl)-carbamic acid tert-butyl ester:

To 2-bromobenzylamine hydrochloride (125.0 g, 561.8 mmol), in THF/water (1:1, 300 mL), was added potassium carbonate (170.7 g, 1236.0 mmol) and di-tert-butyl dicarbonate (134.9 g, 618.0 mmol), in four portions over 20 minutes. The mixture was stirred at room temperature for 16 h and diluted with 300 mL of EtOAc and 300 mL of water. The organic portion was separated and the aqueous portion was extracted with EtOAc (3×200 mL). The combined EtOAc portions were washed with 250 mL of 10% aqueous sodium bisulfate, dried (MgSO4), and concentrated to dryness to afford 161.0 g of the title compound.

B. 3-[2-(tert-Butoxycarbonylamino-methyl)-phenyl]-acrylic acid methyl ester:

To the product from part A (161.0 g, 561.8 mmol), in DMF (800 mL), was added methyl acrylate (58.0 g, 674.2 mmol), TEA (170.5 g, 1685.4 mmol), and dichlorobis(triphenylphosphine)palladium(II) (7.9 g, 11.2 mmol) and the mixture was heated at 80° C. for 32 h. The mixture was cooled, diluted with 1000 mL of EtOAc and washed with 10% aqueous sodium bisulfate. The aqueous portion was extracted three times with EtOAc and the combined organics were dried ($Na_2SO_4$) and concentrated to dryness. The residue was dissolved in a small amount of DCM and filtered through 7 in. of silica gel in a 2 L sintered glass funnel eluting with 25% EtOAc/hexanes. The eluent was concentrated to dryness and recrystallized from EtOAc/hexanes to afford 116.9 g (71%) of the title compound.

C. To a 0° C. solution of the material from Part B (116.9 g, 401.2 mmol) in 800 mL of DCM was added 200 mL of TFA dropwise over 15 min. After removing the cooling bath, the mixture was stirred for 2.5 h and concentrated to dryness. The residue was dissolved in 500 mL of DCM and saturated aqueous sodium bicarbonate was slowly added until the mixture was slightly basic. The organic portion was separated and the aqueous portion was extracted two times with DCM. The combined organic portions were dried ($Na_2SO_4$) and concentrated to dryness. The residue was dissolved in 800 mL of DCM and to the mixture was added DIPEA (57.0 g, 441.4 mmol) and di-tert-butyl dicarbonate (96.3 g, 441.4 mmol) in five portions over 45 minutes and the mixture stirred at room temperature for 16 h. The mixture was washed with 10% aqueous sodium bisulfate, the organic portion was separated and the aqueous portion extracted two times with DCM. The combined organic extracts were dried ($Na_2SO_4$) and concentrated. The residue was dissolved in a small amount of DCM and filtered through 7 in. of silica gel in a 2 L sintered glass funnel eluting with 25% EtOAc/hexanes. The eluent was concentrated to dryness and the enantiomers separated by chiral chromatography (Chiralcel OD). The first eluting isomer was labeled isomer #1 and the second eluting isomer #2; affording 52.6 g (45%) of the title compound (isomer 2).

EIS-MS 292 [M+1].

Preparation C2

1-Carboxymethyl-1,3-dihydro-isoindole-2-carboxylic acid tert-butyl ester

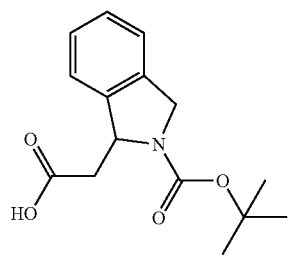

To the product from Preparation C1 (52.6 g, 180.5 mmol), in MeOH (500 mL), was added 1 N NaOH (199 mL, 199.0 mmol). The mixture was stirred at room temperature for 48 h and then concentrated to dryness. The resulting residue was dissolved in water (300 mL) and extracted with diethyl ether (2×). The aqueous portion was acidified to pH 2 with 10% aqueous sodium bisulfate and extracted with EtOAc. The combined organic extracts were dried ($MgSO_4$) and concentrated to dryness. Yield: 49.8 g, 99%. EIS-MS 276 [M−1].

Preparation BC2

1-{[1-Carboxy-2-(4-chloro-phenyl)-ethylcarbamoyl]-methyl}-1,3-dihydro-isoindole-2-carboxylic acid tert-butyl ester

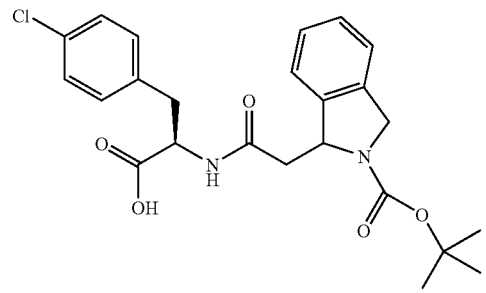

A. To a suspension of 4-Cl-D-Phe methyl ester hydrochloride (40.4 g, 161.5 mmol), in DCM (250 mL), was added saturated aqueous sodium bicarbonate (250 mL) and the mixture stirred at room temperature for 1 h. The organic portion was separated and the aqueous portion was extracted with DCM (2×). The combined organic portions were dried ($Na_2SO_4$) and concentrated to dryness. To the free amine, in DCM (400 mL) at 0° C., was added example C2 (isomer 2, 44.8 g, 161.5 mmol), EDC (31.0 g, 161.5 mmol) and 4-DMAP (2.0 g, 16.1 mmol). The reaction mixture was stirred at 0° C. for 30 minutes whereupon the cooling bath was removed and the reaction mixture was stirred for another 5 h at room temperature. The mixture was then washed with saturated aqueous sodium bicarbonate (200 mL), 10% aqueous sodium bisulfate (200 mL), dried (Na$_2$SO$_4$), and the organic phase was concentrated to dryness to afford 76.4 g (100%) of the ester. EIS-MS 471 [M−1].

B. To the ester from Part A (76.4 g, 161.5 mmol), in MeOH (760 mL), was added 1 N NaOH (242.0 mL, 242.0 mmol) and the mixture heated at 50° C. for 4 h. then stirred for another 16 h at room temperature. After concentrating to dryness, the resulting residue was taken up in 500 mL of water and washed with diethyl ether (2×). The aqueous portion was acidified to pH 2 with 10% aqueous sodium bisulfate and extracted with EtOAc (4×200 mL). The combined organic extracts were dried (MgSO$_4$) and concentrated to dryness. The resulting solid was suspended in hexanes, filtered, and dried to afford 67.7 g (91%) of the title compound. EIS-MS 457 [M−1].

Preparation C3

1-Carboxymethyl-3,4-dihydro-1H-isoquinoline-2-carboxylic acid tert-butyl ester, lithium salt

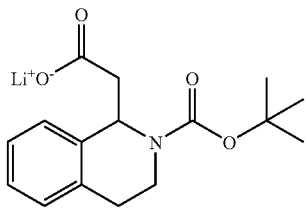

A. (1,2,3,4-Tetrahydro-isoquinolin-1-yl)-acetic acid methyl ester:

To Boc-tetrahydoisoquinoline-1-acetic acid (100.4 g, 520.0 mmol), in MeOH (200 mL), was added 400 mL of 2.3 M HCl in methanol. The mixture was stirred overnight and then concentrated to dryness. The resulting residue was dissolved in EtOAc, washed with saturated sodium bicarbonate, brine, dried (Na$_2$SO$_4$), and concentrated to dryness; affording 109.5 g (100%) of the ester. EIS-MS 206 [M+1].

B. 1-Methoxycarbonylmethyl-3,4-dihydro-1H-isoquinoline-2-carboxylic acid tert-butyl ester:

To a 0° C. solution of material from part A (50.5 g, 240.0 mmol), in THF (250 mL), was added di-tert-butyl dicarbonate (59.3 g, 270.0 mmol), in THF (50 mL), dropwise. After stirring 45 minutes, the mixture was concentrated to dryness. The resulting residue was dissolved in EtOAc, washed with saturated sodium bicarbonate, brine, dried (Na$_2$SO$_4$), and concentrated to dryness. Chiral chromatography (Chiracel OD) of the residue afforded both enantiomers, with the first eluting isomer labeled isomer 1 and the second isomer 2. EIS-MS 306 [M+].

C. To a solution of material from part B (10.2 g, 33.4 mmol), in dioxane (220 mL), was added a solution of lithium hydroxide monohydrate (1.67 g, 39.8 mmol), in water (110 mL), portionwise so as to maintain a temperature below 30° C. The mixture was stirred for 16 h and then concentrated to dryness; affording 11.2 g of the lithium salt. EIS-MS 292 [M+1].

Preparation BC3

Lithium 2-[(2-tert-butoxycarbonyl-1,2,3,4-tetrahydro-isoquinolin-3-ylmethyl)-amino]-3-(4-chlorophenyl)-propionate

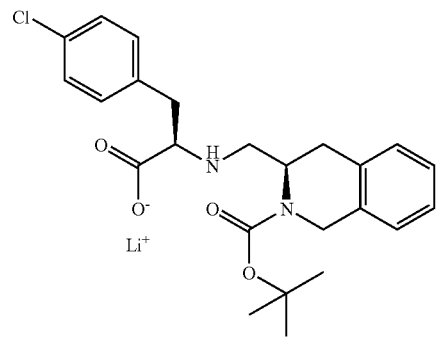

A. 3-(Methoxy-methyl-carbamoyl)-3,4-dihydro-1H isoquinoline-2-carboxylic acid tert-butyl ester:

To Boc-D-1,2,3,4-tetrahydroisoquinoline carboxylic acid (14.9 g, 53.7 mmol), in THF (500 mL), was added N,O-dimethylhydroxylamine hydrochloride (5.24 g, 53.7 mmol), EDC (11.3 g, 59.1 mmol), HOBT (7.98 g, 59.1 mmol) and DIPEA (9.83 ml, 56.4 mmol) The mixture was stirred for 16 h, at room temperature and under nitrogen and then concentrated to dryness. The resulting residue was taken up in EtOAc, washed with 1M HCl, saturated sodium bicarbonate, brine, and dried (Na$_2$SO$_4$). After concentrating to dryness, the resulting residue was purified by flash chromatography (SiO$_2$, eluting with 1:1 EtOAc/hexane) to give 12.3 g (71%) of the ester. EIS-MS 321 [M+1].

B. 3-Formyl-3,4-dihydro-1H-isoquinoline-2-carboxylic acid tert-butyl ester:

To a 0° C. solution of material from part A (1.28 g, 4.00 mmol) in THF (30 mL), was slowly added 1.0 M LAH (in THF, 5.1 ml, 5.1 mmol). The reaction mixture was stirred at 0° C. for another 15 minutes. To the mixture was slowly added 20 mL of 5% aqueous potassium hydrogensulfate and the mixture extracted with Et$_2$O (2×). The combined organic portions were washed with 1M hydrochloric acid, saturated sodium bicarbonate, brine, dried (Na$_2$SO$_4$), and concentrated to dryness; affording 0.78 g (75%) of the title compound. EIS-MS 262 [M+1].

C. 3-{[2-(4-Chloro-phenyl)-1-methoxycarbonyl-ethylamino]-methyl}-3,4-dihydro-1H-isoquinoline-2-carboxylic acid tert-butyl ester:

To a 0° C. solution of 4-Cl-D-Phe methyl ester (6.27 g, 25.1 mmol) and sodium acetate (8.23 g, 100.0 mmol), in 850 ml dry MeOH, was added material from part B (9.8 g, 37.6 mmol), in 50 ml MeOH. The mixture was stirred for 15 minutes and then sodium cyanoborohydride (2.37 g, 37.6 mmol) added. The cooling bath was removed and the reaction stirred for 16 h at room temperature. The mixture was concentrated to dryness and the resulting residue taken up in water and 1 ml of 1M HCl. The mixture was extracted with EtOAc and the organics washed with saturated sodium bicarbonate, brine, dried (Na₂SO₄), and concentrated to dryness. The resulting residue was purified by flash chromatography (SiO₂, eluting with 2:1 hexane/EtOAc) affording 8.62 g (75%) of the title compound. EIS-MS 459 [M+1].

D. To a 12° C. solution of material from part C (1.11 g, 2.42 mmol), in dioxane (15 ml), was added a solution of lithium hydroxide (0.10 g, 2.42 mmol), in water (7.5 mL). The mixture was stirred for 16 h and then concentrated to dryness; affording 1.08 g (100%) of the title compound. EIS-MS 445 [M+1].

Preparation C4

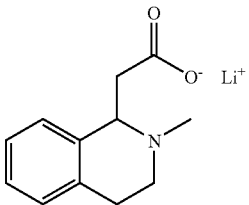

A. (1,2,3,4-Tetrahydro-isoquinolin-1-yl)-acetic acid methyl ester:

To the product from Preparation C3, part B (9.98 g, 32.7 mmol) was added 500 mL of cold 4M HCl in dioxane. After one hour, the mixture was concentrated to dryness. The resulting residue was dissolved in EtOAc, the organics washed with saturated sodium bicarbonate, brine, dried (Na₂SO₄), and concentrated to dryness; affording 6.9 g (100%) of the amine. EIS-MS 206 [M+1].

B. (2-Methyl-1,2,3,4-tetrahydro-isoquinolin-1-yl)-acetic acid methyl ester:

To the product from part A (6.71 g, 32.0 mmol), in dichloroethane (175 mL), was added 37% aqueous formaldehyde (22.6 mL, 300 mmol). After 10 minutes, sodium triacetoxyborohydride (31.2 g, 147.0 mmol) was added in 2-3 g portions, with cooling maintain so as to maintain ambient temperature. Upon completion of addition, the mixture was stirred for 16 h at room temperature. DCM and water was then added and the mixture adjusted to pH 9-10 with 5N NaOH. The organic layer was separated, washed with brine, dried (Na₂SO₄), and concentrated to dryness. The resulting residue was purified by flash chromatography (SiO₂, eluting with DCM/2N ammonia in methanol, 95:5); affording 6.9 g (96%) of the title compound. EIS-MS 220 [M+1].

C. To part B (4.45 g, 18.9 mmol), in dioxane (120 mL), was added lithium hydroxide monohydrate (1.02 g, 22.7 mmol), in water (65 mL) portion-wise; thereby keeping the temperature below 30° C. After 16 h the mixture was concentrated to dryness; affording 8.12 g of the title compound. EIS-MS 206 [M+1].

Preparation C5

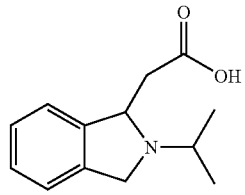

A. (2,3-dihydro-1H-isoindol-1-yl)-acetic acid methyl ester:

To the product from Preparation C1 (11.75 g., 40.41 mmol), in DCM (50 mL), was added TFA (50 mL) dropwise. After 2 hr, the solution was concentrated to dryness and the resulting residue partioned with saturated aqueous sodium bicarbonate (200 mL) and EtOAc (300 mL). The organic portion was separated and the aqueous layer was extracted with DCM (4×500 mL). The combined DCM extracts were combined, dried (Na₂SO₄), and concentrated to dryness to afford 3.97 g (51%) of the title compound.

B. (2-Isopropyl-2,3-dihydro-1H-isoindol-1-yl)-acetic acid methyl ester:

To the product from part A (0.50 g, 2.61 mmol), in dichloroethane (46 mL), was added acetone (1.76 mL, 24.01 mmol) and sodium triacetoxyborohydride (2.48 g., 11.74 mmol). After 6 h, the mixture was diluted with 1.0N NaOH (100 mL), the organic portion was separated and the aqueous layer extracted with DCM (3×100 mL). The combined DCM extracts were combined, dried (MgSO₄), and concentrated to dryness to afford 0.60 g (99%) of the title compound. EIS-MS 235 [M+1].

C. To the product from part B (0.53 g., 2.30 mmol), in MeOH (5.1 mL), was added 1.0N NaOH (2.53 mL, 2.53 mmol). After two days, the solution was concentrated to dryness. The resulting residue was diluted with 1.0N HCl and water then loaded onto a strong cation exchange resin. The resin was washed with water, THF/water (1:1), water, and the product eluted from the resin with pyridine/water (1:9). The eluent was concentrated to dryness to afford 0.43 g (85%) of the title compound. EIS-MS 220 [M+1].

Preparation C6

(2-Methyl-2,3-dihydro-1H-isoindol-1-yl)-acetic acid

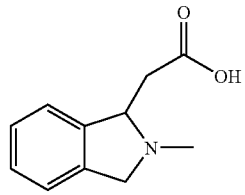

A. (2-Methyl-2,3-dihydro-1H-isoindol-1-yl)-acetic acid methyl ester:

The product from Preparation C1 (0.50 g, 2.61 mmol) with the Boc-carbamate removed as described in step A of preparation C5, was dissolved in dichloroethane (46 mL). This was followed by addition of 37% aqueous formaldehyde solution (1.80 mL, 24.01 mmol) and sodium triac-etoxyborohydride (2.48 g., 11.74 mmol) with stirring. After 3 days, the mixture was diluted with 1.0N NaOH (100 mL). The organic portion was separated and the aqueous layer extracted with DCM (3×100 mL). The combined DCM extacts were dried (Na$_2$SO$_4$) and concentrated to dryness. The resulting residue was purified by flash chromatography (SiO$_2$, eluting with 100% EtOAc); affording 0.43 g (79%) of the alkylated isoindole. EIS-MS 206 [M+1].

B. To the product from part A (0.34 g., 1.66 mmol), in MeOH (3.7 mL), was added 1.0N NaOH (1.82 mL, 1.82 mmol). After 2 days, the solution was concentrated to dryness. The resulting residue was diluted with 1.0N HCl and water then loaded onto a strong cation exchange resin. The resin was washed with water, THF/water (1:1), water, and the product eluted from the resin with pyridine/water (1:9). The eluent was concentrated to dryness to afford 0.31 g (98%) of the title compound. EIS-MS 192 [M+1].

Preparation C7

(2-Butyl-2,3-dihydro-1H-isoindol-1-yl)-acetic acid

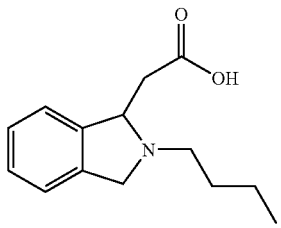

A. (2-Butyl-2,3-dihydro-1H-isoindol-1-yl)-acetic acid methyl ester:

The product from Preparation C1 (0.50 g, 2.61 mmol), with the Boc carbamate (boc group) removed as described in Step A of Preparation C5 was dissolved in dichloroethane (46 mL)followed by addition of butyraldehyde (2.16 mL, 24.01 mmol) and sodium triacetoxyborohydride (2.48 g., 11.74 mmol). After 3 days, the mixture was diluted with 1.0N NaOH (100 mL). The organic portion was separated and the aqueous layer extracted with DCM (3×75 mL). The combined DCM layers were dried (Na$_2$SO$_4$) and concentrated to dryness. The resulting residue was purified by flash chromatography (SiO$_2$, eluting with 1:3, EtOAc/hexanes); affording 0.51 g (77%) of the alkylated isoindole. EIS-MS 249 [M+1].

B. To the product from part A (0.47 g., 1.89 mmol) in MeOH (4.2 mL) was added 1.0N NaOH (2.08 mL, 2.08 mmol). After 2 days, the solution was concentrated to dryness. The residue was diluted with 1.0N HCl and water then loaded onto a strong cation exchange resin. The resin was washed with water, THF/water (1:1), water, and the product eluted from the resin with pyridine/water (1:9). The eluent was concentrated to dryness to afford 0.28 g (64%) of the title compound. EIS-MS 234 [M+1].

Preparation C8

Potassium(2-methyl-2,3-dihydro-1H-isoindol-1-yl)-acetate

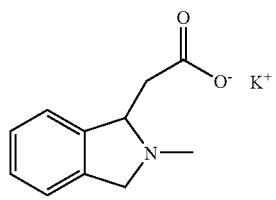

To Preparation C6, part A (2.65 gm, 12.9 mmol), in THF (27 mL) was added potassium trimethysilanolate (1.66 gm, 12.9 mmol) and the reaction stirred for two days. After concentrating to dryness the resulting thick solid was triturated with diethyl ether, filtered, washed with diethyl ether, and dried at room temperature to afford 2.73 g (92%) of the title compound. EIS-MS 192 [M+1].

Preparation C9

7-Fluoro-3,4-dihydro-1H-isoquinoline-2,3-dicarboxylic acid 2-tert-butyl ester

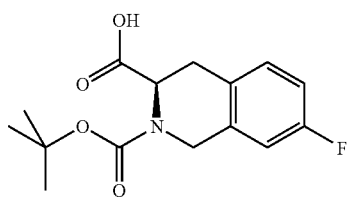

A. Amino-3-(4-fluoro-phenyl)-propionic acid:

To N-Boc-4-Fluoro-D-Phe (2.37 g, 8.366 mmol), in MeOH, 3 mL of concentrated sulfuric acid was added. The reaction mixtured was heated to reflux overnight then concentrated to dryness to afford the title compound. EIS-MS 198 [M+1].

B. Ethoxycarbonylamino-3-(4-fluoro-phenyl)-propionic acid:

To a 0° C. mixture of material from part A (1.65 g, 8.37 mmol) and pyridine (1.35 mL, 17.4 mmol), in DCM, was slowly added ethyl chloroformate (0.85 mL, 8.87 mmol). After 30 minutes the mixture was partitioned between water and EtOAc. The aqueous layer was extracted with EtOAc (2×). The combined organic extracts were dried (MgSO$_4$) and concentrated to dryness to afford 2.17 g (96%) of the title compound. EIS-MS 270 [M+1].

C. 7-Fluoro-3,4-dihydro-1H-isoquinoline-2,3-dicarboxylic acid 2-ethyl ester:

A mixture of material from part B (2.17 g, 8.06 mmol), paraformaldehyde (0.254 g, 8.46 mmol), and 10 mL of 3:1 glacial acetic acid/concentrated sulfuric acid was stirred at room temperature for 48 h. The mixture was then partitioned between water and EtOAc. The organic portion was separated and the aqueous layer extracted with EtOAc (3×). The combined EtOAc extracts were dried (MgSO$_4$), and concentrated to dryness. Flash chromatography of the resulting residue (SiO$_2$, eluting with 25% EtOAc/Hexane); affording 1.31 g (58%) of the title compound. EIS-MS 282 [M+1].

D. 7-Fluoro-1,2,3,4-tetrahydro-isoquinoline-3-carboxylic acid:

The product from Part C (1.31 g, 4.656 mmol), in 20 mL of 5N HCl, was heated at reflux for 24 h. The solution was then concentrated to dryness. The resulting white solid was washed with Et$_2$O to afford 0.87 g (81%) of the title compound. EIS-MS 196 [M+1].

E. To the product from part D (0.87 g, 3.75 mmol), in 20 ml of 1:1 dioxane/water, was added Di-t-butyl-dicarbonate (0.90 g, 4.13 mmol) and TEA (2.36 mL, 16.90 mmol). The mixture was stirred at room temperature for 16 h and then diluted with EtOAc. The organic portion was separated and the aqueous layer extracted with EtOAc (3×). The combined organic portions were dried (MgSO$_4$) and concentrated to dryness to give 0.64 g (58%) of the title compound. EIS-MS 294 [M+1].

Preparation C10

3-Methyl-3,4-dihydro-1H-isoquinoline-2,3-dicarboxylic acid 2-tert-butyl ester

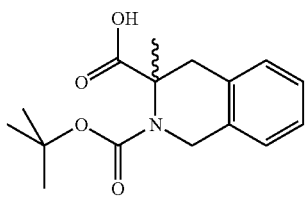

The compound of Preparation C10 was prepared from -methyl-D,L-Phe by following the substantially similar procedure described in Preparation C9; yielding 1.7 g, of the title compound. EIS-MS 292 [M+1].

Preparation C11

3-[2-(tert-Butoxycarbonylamino-methyl)-phenyl]-but-2-enoic acid ethyl ester

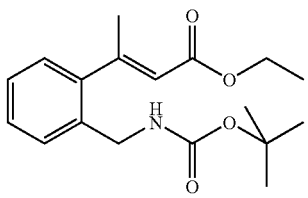

N-Boc-2-bromobenzylamine (7.15 g, 25 mmol) was dissolved into tributylamine (12 mL) and degassed under vacuum. Palladium acetate (224 mg, 1 mmol) and tri-o-tolylphosphine (608 mg, 2 mmol) was then added and the mixture degassed under vacuum. Trans-ethylcrotonate (6.25 mL, 50 mmol) was then added and the mixture was degassed with nitrogen. The tube was sealed and the mixture was heated to 110° C. for 48 h. The solution was cooled to room temperature, diluted with diethyl ether (200 mL) and filtered through celite. The solution was washed with 1N HCl (2×50 mL) and brine (50 mL) dried over magnesium sulfate and concentrated to dryness. Flash chromatography (9:1 hexanes/ethyl acetate) gave the title compound as a yellow oil (1.6 g, 20%). $^1$H NMR 7.22-7.37 (m, 3H), 7.08 (dd, J=7.4, 1.6 Hz, 1H), 5.75 (d, J=1.3 Hz, 1H), 4.29-4.31 (m, 2H), 4.20 (q, J=7.1 Hz, 2H), 2.45 (d, J=1.3 Hz, 3H), 1.44 (s, 9H), 1.30 (t, J=7.1 Hz, 3H).

Preparation C12

(1-Methyl-2,3-dihydro-1H-isoindol-1-yl)-acetic acid ethyl ester

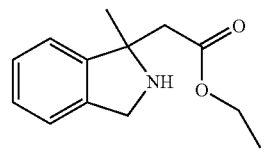

To Preparation C11 (1.6 g, 5 mmol), in CH$_2$Cl$_2$, was added TFA (10 mL). The mixture was stirred for 1 h at room temperature and concentrated to a yellow oil. TEA (5 mL) was added and the solution was stirred for 15 minutes and concentrated to dryness. Purification by flash chromatography (SiO$_2$, eluting with 5% 2N NH$_3$ in MeOH/EtOAc) gave the title compound as a clear oil (1.0 g, 92%).

Preparation C13

1-Ethoxycarbonylmethyl-1-methyl-1,3-dihydro-isoindole-2-carboxylic acid tert-butyl ester

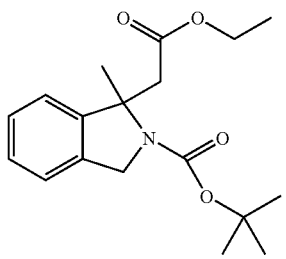

(1-Methyl-2,3-dihydro-1H-isoindol-1-yl)-acetic acid ethyl ester (1.0 g, 4.6 mmol) and di-tert-butyl dicarbonate (1.1 g, 5.06 mmol) were dissolved into DCM (10 mL) under nitrogen atmosphere. The solution was cooled to 0° C. followed by dropwise addition of TEA (0.71 mL, 5.06 mmol). The solution was warmed to room temperature and stirred 72 h. DCM (50 mL) was added and the solution washed with saturated sodium bicarbonate (5 mL), H$_2$O (5 mL) and brine (5 mL). The organic phase was dried over magnesium sulfate and concentrated to a clear oil. Purification by flash chromatography (SiO$_2$) gave the title compound as a clear oil (1.18 g, 81%). 1H NMR (CDCl$_3$) δ 7.10-7.30 (m, 4H), 4.65-4.70 (m, 2H), 3.84-3.92 (m, 2H), 3.42-3.48 (m, 0.5H), 2.65-2.80 (m, 1.5H), 1.75 (s, 1.6H), 1.68 (s, 1.4H), 1.55 (s, 5H), 1.48 (s, 4H).

Preparation C14

1-Carboxymethyl-1-methyl-1,3-dihydro-isoindole-2-carboxylic acid tert-butyl ester

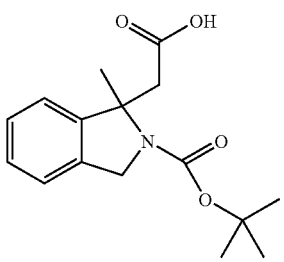

Compound of Preparation C13 (1.14 g, 3.56 mmol) was dissolved into ethanol (10 mL) and H₂O (2 mL) and cooled to 0° C. Lithium hydroxide (470 mg, 11.1 mmol) was added and the mixture was stirred at room temperature for 24 h. Lithium hydroxide (340 mg, 8 mmol) was added and the solution was stirred for about 24 h. A 1 N solution of NaOH (5 mL) was added and the solution was washed with hexanes (10 mL). The aqueous solution was acidified with 1N HCl to pH 1. The solution was extracted with EtOAc (3×20 mL), dried over magnesium sulfate and concentrated to a white solid. The residue was recrystallized from hexanes to give the title compound (850 mg, 82%). $^1$H NMR (CDCl₃) δ 7.10-7.30 (m, 4H), 4.60 (s, 2H), 3.65-3.80 (m, 0.6H), 3.30-3.40 (m, 0.4H), 2.70-2.80 (m, 1H), 1.65-75 (m, 3H), 1.45-1.60 (m, 9H).

Preparation BC4

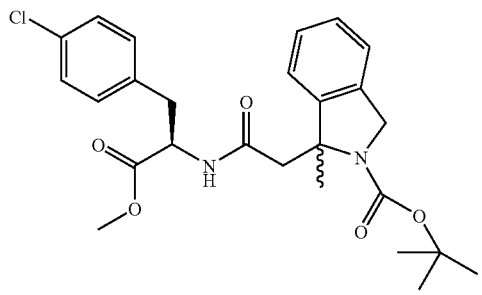

To 4-Chloro-D-Phenylalanine methyl ester hydrochloride (0.432 g, 1.73 mmol) was added Compound of preparation C13 (0.504 g, 1.73 mmol), EDC (0.330 g, 1.73 mmol) and HOBT (0.233 g, 1.73 mmol). This was followed by addition of dichloromethane (5 mL) and DIPEA (0.452 mL). The solution was stirred for 3 h then diluted with EtOAc (50 mL). The organics were washed with saturated NaHCO₃ (50 mL), water (50 mL), and concentrated to dryness. The crude product was purified by flash chromatography (SiO₂, eluting with Hexane/EtOAc, 80:20) yielding 0.724 g, 86% of the title compound as a white solid. EIS-MS 487.2 [M+1].

Preparation BC5

3-(4-Chloro-phenyl)-2-[2-(1-methyl-2,3-dihydro-1H-isoindol-1-yl)-acetylamino]-propionic acid methyl ester

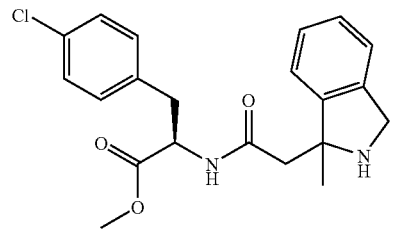

To compound of Preparation BC4 in DCM (3 mL), was added TFA (3 mL) and the mixture was allowed to stand for 2 h. After concentrating to dryness, the diastereomers were separated by reverse phase HPLC [Waters Symmetry C18 column, eluting with H₂O (0.05% HCl)/CH₃CN, 90:10 to 60:40, following a straight line gradient]. The first eluting isomer was labeled isomer 1 and the second isomer 2. EIS-MS 387.1 [M+1] for both isomers.

Preparation BC6

1-{[2-(4-Chloro-phenyl)-1-methoxycarbonyl-ethyl-carbamoyl]-methyl}-1-methyl-1,3-dihydro-isoindole-2-carboxylic acid tert-butyl ester, isomer 1

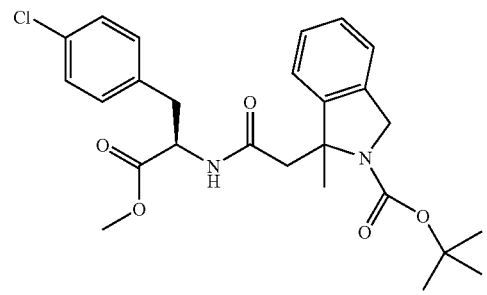

To the compound of Preparation BC5 (isomer 1, 0.321 g, 0.831 mmol), in THF/H2O 1:1, 4 mL) was added K₂CO₃ (0.253 g, 1.83 mmol) and BOC₂O. The mixture stirred for 12 h and then the crude mixture was diluted with EtOAc (25 mL), the organics washed with H₂O and concentrated to dryness; yielding the title compound (0.33 g, 81%). EIS-MS 487.1 [M+1].

Preparation BC7

1-{[2-(4-Chloro-phenyl)-1-methoxycarbonyl-ethyl-carbamoyl]-methyl}-1-methyl-1,3-dihydro-isoindole-2-carboxylic acid tert-butyl ester, isomer 2

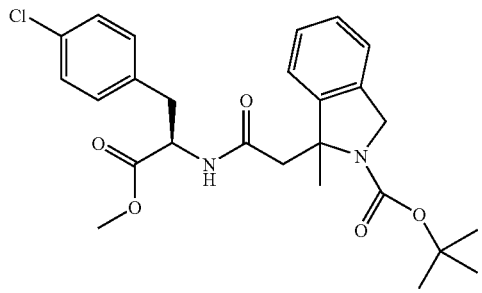

The compound of Preparation BC7 was prepared from the compound of Preparation BC5 (isomer 2) by following the substantially similar procedure described in Preparation BC6.

Preparation BC8

1-{[1-Carboxy-2-(4-chloro-phenyl)-ethylcarbamoyl]-methyl}-1-methyl-1,3-dihydro-isoindole-2-carboxylic acid tert-butyl ester, isomer 1

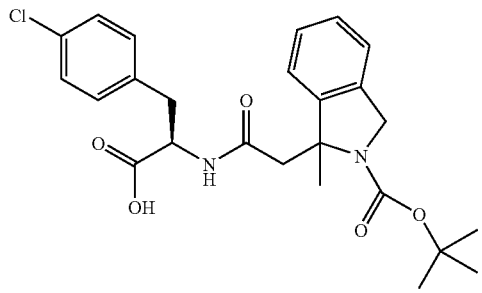

To the product from Preparation BC6 (isomer 1, 0.330 g, 0.679 mmol) in H$_2$O/THF 1:1 (10 mL) was added LiOH (0.050 g, 2.01 mmol). The mixture was stirred for 5 h, then diluted with H$_2$O (50 mL) and acidified to pH 4 with 25% KHSO$_4$. The aqueous mixture was extracted with EtOAc (100 mL) and concentrated to dryness; yielding the title compound (0.335 g). EIS-MS 473.2 [M+1].

Preparation BC9

1-{[1-Carboxy-2-(4-chloro-phenyl)-ethylcarbamoyl]-methyl}-1-methyl-1,3-dihydro-isoindole-2-carboxylic acid tert-butyl ester, isomer 2

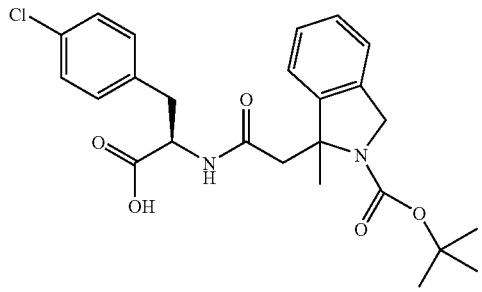

Preparation BC9 was prepared from the compound of Preparation BC7 (isomer 2) by following the substantially similar procedure described in Preparation BC8; yielding 0.26 g, 95% of the title compound.

EIS-MS 473.3 [M+1].

Preparation BC10

3-(4-Chloro-phenyl)-2-[(1,1-dimethyl-1,2,3,4-tetrahydro-isoquinoline-3-carbonyl)-amino]-propionic acid methyl ester

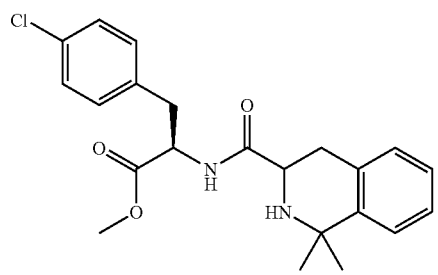

To a solution of 1,1-dimethyl TIC (240 mg, 1.17 mmol), 4-Cl-D-Phe methyl ester (322 mg, 1.28 mmol), HOBT (197 mg, 1.46 mmol), and DIPEA-(0.81 mL, 44.68 mmol, 4.0 eq) in CH$_2$Cl$_2$/DMF (1:1) was added EDC (280 mg, 1.46 mmol). The resulting mixture was stirred at room temperature overnight. The reaction mixture was then diluted with EtOAc (100 mL), washed with saturated aqueous NaHCO$_3$, brine, dried (Na$_2$SO$_4$) and concentrated to dryness. Purification and separation of diastereomers by flash chromatography (35 g SiO$_2$, linear gradient, 40 mL/min 10-50% EtOAc/hexane for 25 minutes and 50% EtOAc/hexane for 7 minutes) afforded title compound.

Preparation BC11

3-(4-Chloro-phenyl)-2-[(1,1-dimethyl-1,2,3,4-tetrahydro-isoquinoline-3-carbonyl)-amino]-propionic acid

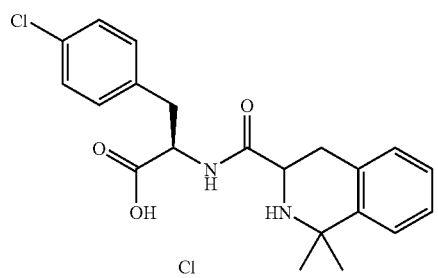

To Preparation BC10 (5.95 g, 14.88 mmol), in a 1:1 mixture of THF/H$_2$O (50 mL), was added lithium hydroxide hydrate (0.75 g, 17.87 mmol). The reaction was stirred at room temperature for 18 h. The mixture was then concentrated to dryness. The resulting residue was dissolved in water (50 mL), made acidic with 1N HCl (25 mL) and washed with Et$_2$O (100 mL). The aqueous layer was evaporated to dryness, yielding 6.18 g (98%) of the title compound. EIS-MS 387 [M+1].

Preparation BC12

1-{[1-Carboxy-2-(4-chloro-phenyl)-ethylcarbamoyl]-methyl}-3,4-dihydro-1H-isoquinoline-2-carboxylic acid tert-butyl ester, isomer 1

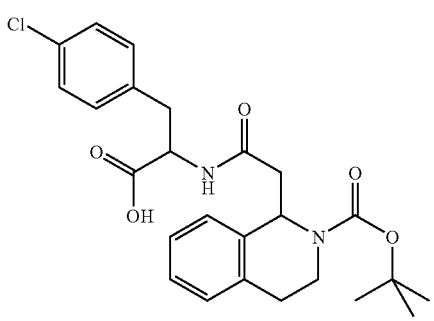

A. To a solution of D-4-chlorophenylalanine methyl ester hydrochloride (883 mg, 3.53 mmol), Preparation C3 (isomer 1) (1.0 g, 3.36 mmol), HOBT (568 mg, 4.2 mmol), and DIPEA (2.92 mL, 16.8 mmol) in $CH_2Cl_2$ (35 mL) was added EDC (805 mg, 4.2 mmol). The resulting mixture was stirred at room temperature for 48 h. The reaction mixture was poured into a mixture $CH_2Cl_2$-water (1:1) and the organic phase washed with water (2×), dried ($Na_2SO_4$), filtered, and concentrated to dryness. Final purification by flash chromatography EtOAc-hexane (3:7) afforded 1.38 g of desired compound as a white solid. MS m/z 485.2 ($M^+$−1)

B. To a solution of the above-formed ester (1.38 g, 2.83 mmol) in THF (15 mL), a 1M aqueous solution of $LiOH \cdot H_2O$ (14.15 mL, 14.15 mmol) was added and mixture stirred at room temperature for 1 h. Reaction was cooled to 0° C. and pH was adjusted to ≈1 upon addition of 1M HCl. Aqueous layer was extracted with EtOAc, dried ($Na_2SO_4$), and evaporated to afford 1.32 g of the title compound as a white solid. MS m/z 471.2 ($M^+$−1)

Preparation BC13

1-{[1-Carboxy-2-(4-chloro-phenyl)-ethylcarbamoyl]-methyl}-3,4-dihydro-1H-isoquinoline-2-carboxylic acid tert-butyl ester, isomer 2

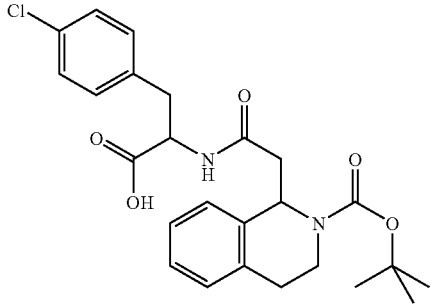

The compound of Preparation BC13 was prepared from Preparation C3 (isomer 2) by following a procedure substantially similar to that described in Preparation BC12. MS m/z 471.2 ($M^+$−1)

Preparation BC14

3-(4-Chloro-phenyl)-2-[2-(2-methyl-2,3-dihydro-1H-isoindol-1-yl)-acetylamino]-propionic acid

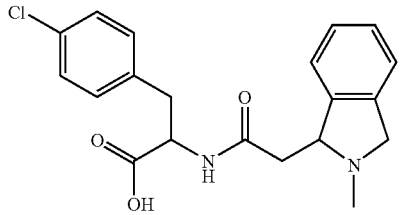

A. To a solution of D-4-chlorophenylalanine methyl ester hydrochloride (1.37 g, 5.49 mmol), Preparation C6 (1.2 g, 5.23 mmol), HOBT (883 mg, 6.54 mmol), and DIPEA (4.55 mL, 26.2 mmol) in $CH_2Cl_2$ (35 mL) was added EDC (1.25 g, 6.54 mmol). The resulting mixture was stirred at room temperature for 48 h. The reaction mixture was poured onto a mixture $CH_2Cl_2$-water (1:1) and the organic phase washed with water (2×), dried ($Na_2SO_4$), filtered, and concentrated to dryness. Final purification by flash chromatography (EtOAc, then EtOAc/MeOH/AcOH 95:5:5) afforded 1.71 g of desired compound as a solid. MS m/z 387.1 ($M^+$+1)

B. To a solution of the above-formed ester (1.71 g, 4.4 mmol) in THF (40 mL), a 1M aqueous solution of $LiOH \cdot H_2O$ (22.1 mL, 22.1 mmol) was added and mixture stirred at room temperature for 1 h. Reaction was cooled to 0° C. and pH was adjusted to ≈1 upon addition of 1M HCl. Aqueous layer was extracted with EtOAc, dried ($Na_2SO_4$), and evaporated to afford 1.6 g of the title compound as a solid. MS m/z 373.2 ($M^+$+1)

Preparation BC15

3-(4-Chloro-phenyl)-2-[(isoquinoline-3-carbonyl)-amino]-propionic acid

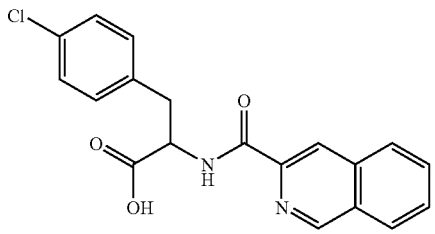

A. To a solution of D4-chlorophenylalanine methyl ester hydrochloride (758 Mg, 3.03 mmol), 3-isoquinolinecarboxylic acid hydrate (500 mg, 2.89 mmol), HOBT (488 mg, 3.61 mmol), and DIPEA (2.51 mL, 14.45 mmol) in $CH_2Cl_2$ (30 mL) was added EDC (692 g, 3.61 mmol). The resulting mixture was stirred at room temperature overnight. The reaction mixture was poured onto a mixture EtOAc (50 mL) and water (20 mL) and the organic phase washed with water (3×), dried ($Na_2SO_4$), filtered, and concentrated to dryness. Final purification by flash chromatography (EtOAc/hexane 1:2) afforded 820 mg of desired compound as a solid. MS m/z 369.1 ($M^+$+1).

B. To a solution of the above-formed ester (820 mg, 2.26 mmol) in THF (10 mL), a 1M aqueous solution of LiOH.H₂O (11.3 mL, 11.3 mmol) was added and mixture stirred at room temperature for 1 h. Reaction was cooled to 0° C. and pH was adjusted to =1 upon addition of 1M HCl. Aqueous layer was extracted with EtOAc, dried (Na₂SO₄), and evaporated to afford 790 mg of the title compound as a solid. MS m/z 353.0 (M⁺−1)

Procedures for Preparing A-domain Pieces

Procedure I

Preparation 1A

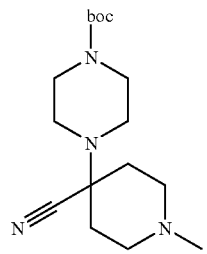

To a flask was added 1-Methyl-piperidin-4-one (5.00 g, 44.25 mmol), Trimethylsilyl cyanide (TMSCN) (4.38 g, 44.23 mmol) and Diethyl ether (5 mL) followed by addition of Zinc iodide (0.010 g, cat.) the subsequent exothermic reaction was controlled with an ice bath. The mixture was stirred at rt. for 15 minutes. To the solution was added a solution of Boc-piperzine (8.23 g, 44.23 mmol) in Methanol (60 mL). The solution was then refluxed for 3 h and stirred at room temperature for 12 h. the solution was then concentrated to dryness and crystallized from EtOAc/Hexane. Yielding compound 1A (9.08 g, 67%). ES MS 309.3

Compounds 2A-10A were prepared from a mono-protected piperazine and the appropriate ketone by procedures substantial similar to that of procedure I.

TABLE A

| Preparation | Structure | ES MS (M + 1) |
|---|---|---|
| 2A | | 428.2 |
| 3A | 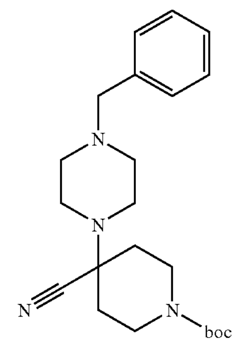 | 385.3 |
| 4A | 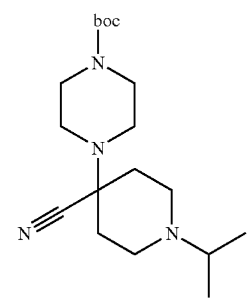 | 337.3 |
| 5A | 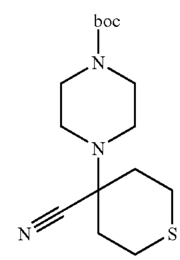 | 312.2 |
| 6A | 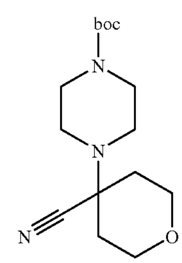 | 296.2 |
| 7A | 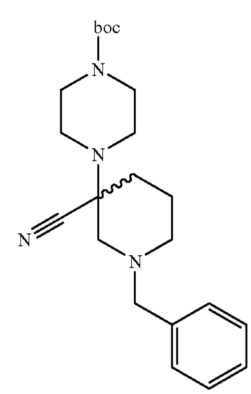 | 385.2 |

TABLE A-continued

| Preparation | Structure | ES MS (M + 1) |
|---|---|---|
| 8A | boc-piperazine-cyclohexane-CN | 394.2 |
| 9A | boc-piperazine-cyclopentane-CN | 253.2 |
| 10A | boc-piperazine-indane-CN | |

Procedure II

Preparation 1B

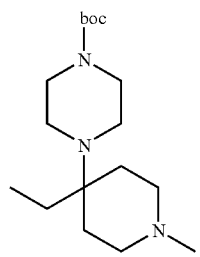

To a solution of Preparation 1A (0.500 g, 1.62 mmol) in THF (4.0 mL) was added ethyl magnesium bromide 3 molar in Et$_2$O (1.62 mL, 4.87 mmol). After stirring for 18 h the mixture was quenched by being poured into water (50 mL). The mixture was extracted with EtOAc (100 mL) and washed once with brine. Then concentrated to dryness yielding a yellow oil. Purification using Silica gel (60 mesh) eluting with CHCl$_3$:MeOH (9:1) yielded compound 1B as a clear oil (0.119 g, 24%) ES MS (M+1)=312.3

The compounds of examples 2B-18B shown in table B below, were prepared from the appropriate amino nitrile (1A-10A) by procedures substantially similar to the preparation of 1B. Where the grignard was not commercial, it was synthesized from the appropriate alkyl halide and magnesium turnings in either THF or Et$_2$O by common literature procedures.

TABLE B

| Prep. | Compound | ES MS (M + 1) | Prep. | Compound | ES MS (M + 1) |
|---|---|---|---|---|---|
| 2B | boc-piperazine-phenyl-N-methylpiperidine | 360.4 | 10B | boc-piperazine-isobutyl-N-isopropylpiperidine | 368.4 |
| 3B | boc-piperazine-benzyl-N-methylpiperidine | 374.4 | 11B | boc-piperazine-isobutyl-thiopyran | 343.3 |

TABLE B-continued

| Prep. | Compound | ES MS (M + 1) | Prep. | Compound | ES MS (M + 1) |
|---|---|---|---|---|---|
| 4B | | 368.4 | 12B | | 327.3 |
| 5B | | 324.3 | 13B | | 311.3 |
| 6B | | 456.4 | 14B | | 416.3 |
| 7B | | 392.3 | 15B | | 325.3 |
| 8B | | 416.4 | 16B | | 311.3 |

TABLE B-continued

| Prep. | Compound | ES MS (M + 1) | Prep. | Compound | ES MS (M + 1) |
|---|---|---|---|---|---|
| 9B | | 494.4 | 17B | | 309.3 |
| | | | 18B | | 359 |

Procedure III

Preparation 11C

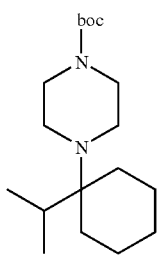

To a solution of compound 16B (0.164 g, 0.532 mmol) in EtOH (10 mL) was added a slurry of 20% Pt on carbon (0.164 g) in EtOH (10 mL). The mixture was then charged with $H_2$ gas via balloon. After vigorous stirring for 4 h the reaction atmosphere was exchanged for N2 gas. The mixture was filtered through a pad of Celite (~5 g) and solvent was removed in vacuo yielding compound 11C (0.133 g, 81%) as pure product.

Procedure IV

Preparation 3C

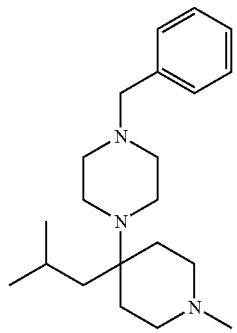

To a slurry of LAH (2.148 g, 56.59 mmol) in THF (100 mL) at room temperature was added compound 8B (11.76 g, 28.30 mmol) in THF (100 mL) dropwise. The reaction was allowed to stir at room temperature for 18 h then heated to reflux for 5 h. The reaction mixture was cooled to 0° C. and quenched carefully with water (8 mL), 15% NaOH (8 mL) and water (26 mL). The mixture was stirred at room temperature for 1 hr, then filtered. The filtrate was then concentrated in vacuo. The residue was partitioned between water and ethyl acetate. The ethyl acetate layer was separated and dried over anhydrous sodium sulfate. Then filtered and concentrated in vacuo. The crude product was purified by chromatography using 5% 2M $NH_3$ in MeOH/95% EtOAc as mobile phase to afford 3.24 g (38%) of pure compound.

Procedure V

Preparation 4C

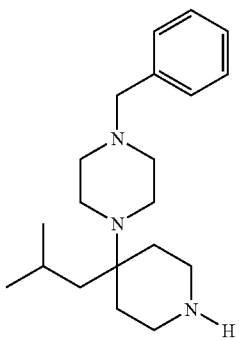

To a solution of compound 8B (2.330 g, 5.614 mmol) in CH$_2$Cl$_2$ (10 mL) was added TFA (10 mL). The solution sat for 2 h followed by concentration in vacuo. The resulting residue was diluted with water (100 mL) and made alkaline with 1M NaOH (100 mL). The aqueous phase was extracted with EtOAc (100 mL), separated and concentrated in vacuo. Compound 4C was obtained cleanly as an oil (1.72 g, 97%).

Procedure VI

Preparation 5C

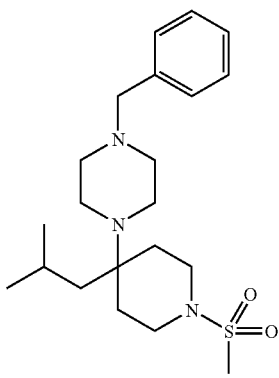

To a solution of compound 4C (0.108 g, 0.347 mmol) in THF at 0° C. was added DIPEA (0.066 mL, 0.377 mmol) followed by Methansulfonyl chloride (0.26 mL, 0.347 mmol). The solution was allowed to warm to room temperature and stir for 4 h. The solution was diluted with EtOAc (50 mL) and washed with water (100 mL). The EtOAc was separated and concentrated in vacuo. The resulting crude material was purified by column chromatography using silica gel (60 mesh) eluting with CHCl$_3$/MeOH (95/5). Compound 5C was collected cleanly (0.130 g, 88%)

Procedure VII

Preparation 6C

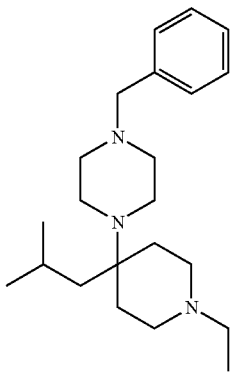

To a solution of compound 4C (0.242 g, 0.768 mmol) in DMF (2.0 mL) was added K$_2$CO$_3$ (0.424 g, 3.073 mmol) and Bromoethane (0.115 mL, 1.537 mmol). The mixture was stirred overnight, diluted with EtOAc (40 mL) and washed with water 3× (20 mL). The EtOAc was separated then concentrated in vacuo. Compound 6C was collected cleanly without further purification (0.218 g, 75%)

Procedure VIII

Preparation 7C

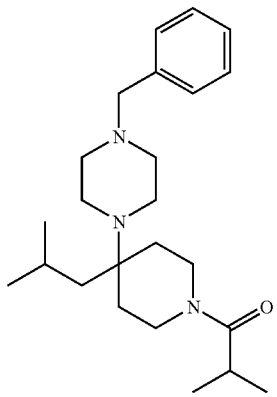

To a solution of compound 4C (0.700 g, 2.22 mmol) in CH$_2$Cl$_2$ was added isobutyric acid (0.21 mL, 2.22 mmol), EDCI (0.426 g, 2.22 mmol) and DMAP (0.005 g, cat.). The solution was stirred for 1 h followed by dilution with EtOAc (100 mL) and washed with water (100 mL). Compound 7C was collected cleanly and used with out further purification (0.83 g, 97%).

Procedure IX

Preparation 8C

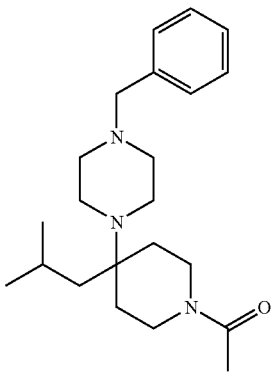

To compound 4C (0.387 g, 1.23 mmol) was added Ac₂O (5 mL) and pyridine (5 mL). The mixture was heated at 65° C. for 1 h and then allowed to cool to room temperature. After diluting with EtOAc (100 mL) the organics were washed with saturated NaHCO₃, H₂O, brine and then concentrated to dryness to afford 305 mg, 70% of compound 8C.

Procedure X

Preparation 9C

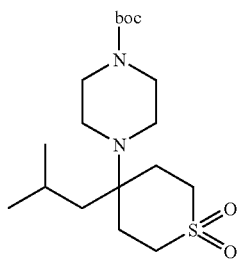

To compound 10B (5.00 g, 14.62 mmol) in CH₂Cl₂ (200 mL) was added methane sulfonic acid and let stir for 5 min. 3-chloroperoxybenzoic acid (70% pure) (7.18 g, 29.23 mmol) was then added portion wise. The mixture stirred for 2 h then poured into NaHCO3(aq) (200 mL). The organics were separated, dried over K2CO3 and concentrated to dryness in vacuo to afford 4.59 g, 84% of high purity compound 9C.

Procedure XI

Preparation 12C

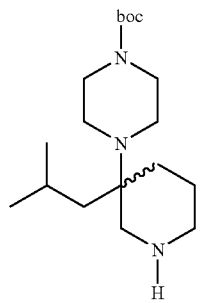

To compound 14B (3.06 g, 7.37 mmol) in EtOH (50 mL) was added a slurry of 10% Pd/C (3.06 g, 1 wt. Eq.) in EtOH (20 mL). The reaction atmosphere was exchanged via vacuum an H₂ balloon leaving the mixture under H₂ gas with vigorous stirring. After 5 h the H₂ gas was exchanged with N₂ gas. The mixture was filtered through celite and concentrated to dryness. Yield of Compound 12C was 2.07 g, or 86% of theory.

Procedure XII

Preparation 13C

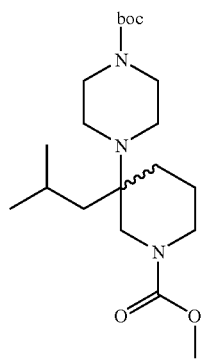

To compound 12C (1.00 g, 3.08 mmol) in THF/H₂O (8 mL/8 mL) was added NaOH (0.246 g, 6.16 mmol). To the mixture was added methyl chloroformate (0.26 mL, 3.38 mmol) dropwise. After vigorous stirring for 5 h the mixture was diluted with EtOAc (100 mL) and washed with water. The organics were separated and dried in vacuo. Compound 13C was collected and used without further purification. Yield: 1.17, 99% of theory.

Compounds 1C-14C were prepared from the appropriate starting material and by following the procedures substantially similar to Procedures III through VIII.

TABLE C

| Example | Compound | ES MS (M + 1) | Starting From | Procedure |
|---------|----------|---------------|---------------|-----------|
| 1C | *(4-boc-piperazinyl, 4-isopropyl, 1-methylpiperidine structure)* | 326.3 | 5B | III |
| 2C | *(4-benzyl-piperazinyl, 4-cyclohexylmethyl, 1-methylpiperidine structure)* | 370.3 | 6B | IV |
| 3C | *(4-benzyl-piperazinyl, 4-isobutyl, 1-methylpiperidine structure)* | 330.3 | 8B | IV |
| 4C | *(4-benzyl-piperazinyl, 4-isobutyl, piperidine NH structure)* | 316.3 | 8B | V |

TABLE C-continued

| Example | Compound | ES MS (M + 1) | Starting From | Procedure |
|---------|----------|---------------|---------------|-----------|
| 5C | | 394.3 | 4C | VI |
| 6C | | 344.4 | 4C | VII |
| 7C | | 386.4 | 4C | VIII |
| 8C | | 358.3 | 4C | IX |

TABLE C-continued

| Example | Compound | ES MS (M + 1) | Starting From | Procedure |
|---|---|---|---|---|
| 9C | [piperazine-boc linked to 4-isobutyl-tetrahydrothiopyran 1,1-dioxide] | 375.3 | 11B | X |
| 10C | [piperazine-boc linked to 4-isopropyl-tetrahydropyran] | 313.3 | 13B | III |
| 11C | [piperazine-boc linked to 1-isopropyl-cyclohexyl] | 311.3 | 17B | III |
| 12C | [piperazine-boc linked to 3-isopropyl-piperidine NH] | 326.3 | 14B | XI |
| 13C | [piperazine-boc linked to 3-isobutyl-piperidine N-CO2Me] | 384.3 | 12C | XII |

TABLE C-continued

| Example | Compound | ES MS (M + 1) | Starting From | Procedure |
|---------|----------|---------------|---------------|-----------|
| 14C | | 284.3 | 13C | V |

Procedure XIII

Preparation 19D

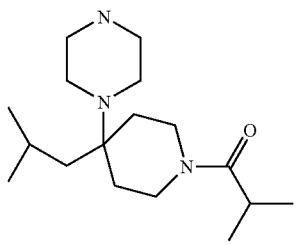

To Pd(OH)$_2$/C (20 wt. % on a dry basis, 300 mg) in EtOH (15 mL) was added compound 8C (0.304 g, 0.85 mmol), in EtOH (10 mL). The mixture was stirred under H$_2$ (1 atm.) for 4 h. The catalyst was removed by filtering over a pad of celite and the filtrate concentrated to dryness to afford 225 mg, 99% of theory of compound 19D.

Compounds 1D-24D were prepared from the appropriate starting material and by following procedures substantially similar to the procedure indicated below.

TABLE D

| Example | Compound | ES MS (M + 1) | Starting From | Procedure |
|---------|----------|---------------|---------------|-----------|
| 1D | | 212.3 | 1B | V |
| 2D | | 260.4 | 2B | V |

TABLE D-continued

| Example | Compound | ES MS (M + 1) | Starting From | Procedure |
|---------|----------|---------------|---------------|-----------|
| 3D | | 274.4 | 3B | V |
| 4D | | 268.4 | 4B | V |
| 5D | | 224.3 | 5B | V |
| 6D | | 292.3 | 7B | V |
| 7D | | 360.2 | 9B | XIII |
| 8D | | 268.4 | 10B | V |
| 9D | | 243.3 | 11B | V |

TABLE D-continued

| Example | Compound | ES MS (M + 1) | Starting From | Procedure |
|---------|----------|---------------|---------------|-----------|
| 10D | | 227.3 | 12B | V |
| 11D | | 225.3 | 15B | V |
| 12D | | 211.3 | 16B | V |
| 13D | | 226.3 | 1C | V |
| 14D | | 280.3 | 2C | XI |
| 15D | | 240.3 | 3C | XI |
| 16D | | 304.2 | 5C | XIII |

TABLE D-continued

| Example | Compound | ES MS (M + 1) | Starting From | Procedure |
|---|---|---|---|---|
| 17D | | 254.3 | 6C | XIII |
| 18D | | 295.3 | 7C | XIII |
| 19D | | 268.2 | 8C | XIII |
| 20D | | 275.3 | 9C | V |
| 21D | | 213.3 | 10C | V |
| 22D | | 211.3 | 11C | V |

TABLE D-continued

| Example | Compound | ES MS (M + 1) | Starting From | Procedure |
|---|---|---|---|---|
| 23D | | 240.2 | 14C | IV |
| 24D | | 259 | 18B | V |

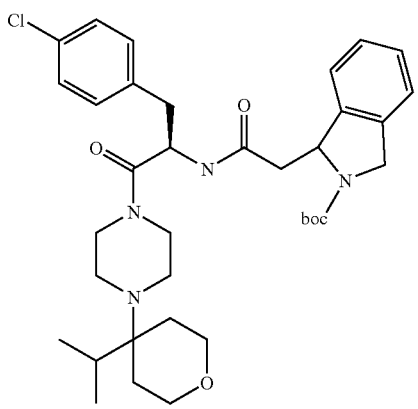

Procedure XIV

EXAMPLE 18E

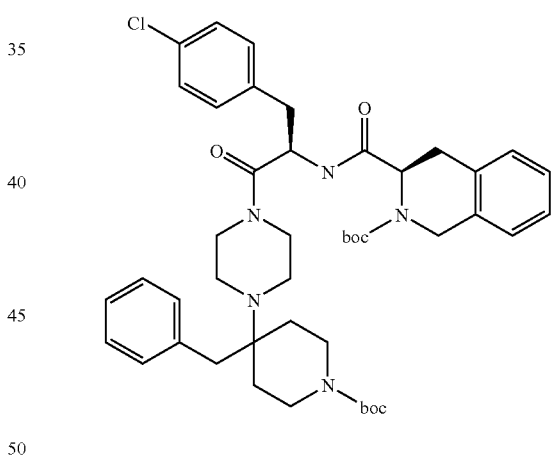

Procedure XV

EXAMPLE 5E

To Compound of preparation 21D (0.310 g, 1.45 mmol) was added compound BC2 (0.669 g, 1.45 mmol), O-(7-Azabenzotriazol-1-yl)-N,N,N',N'-tetramethyluronium hexaflurophosphate (0.554 g, 1.45 mmol), and CH$_2$Cl$_2$ (5 mL). Diisopropylethylamine (1.27 mL, 7.29 mmol) was then added and the mixture stirred at room temperature for 3 h.

After diluting 10 fold with EtOAc the organics were washed with saturated NaHCO$_3$, H$_2$O, brine, and concentrated to dryness. The desired product was purified by flash chromatography (SiO$_2$, eluting with 1:1 EtOAc/Hexanes to 100% EtOAc). Yield: 940 mg, 99% of theory of compound of example 18E. Ion spray MS: 653.3 [M+].

To Compound of Preparation 7D (0.274 g, 0.763 mmol) was added compound of preparation BC1 (0.360 g, 0.763 mmol), O-(7-Azabenzotriazol-1-yl)-N,N,N',N'-tetramethyluronium hexaflurorphosphate (0.290 g, 0.763 mmol), and CH$_2$Cl$_2$ (4 mL) and DMF (1 mL). Diisopropylethylamine (1.3 mL, 7.6 mmol) was then added and the mixture stirred at room temperature for 3 h. After diluting 10 fold with EtOAc the organics were washed with saturated NaHCO$_3$, H$_2$O, brine, and concentrated to dryness. The desired product was purified by flash chromatography (SiO$_2$, eluting with 7:3 Hexanes/EtOAc). The yield of compound of example 5E was 250 mg, or 41% of theory.

Compounds of examples 1E-20E were prepared from the appropriate N-substituted piperazines (1D-23D) and di-peptide acid (compound of preparation BC2 or BC1) by following the procedures substantial similar to XIV and XV.

TABLE E

| Example | Compound | ES MS (M + 1) | Starting From | Procedure |
|---|---|---|---|---|
| 1E | | 652.4 | 1d | XIV, X = BC2 and Y = BCl |
| 2E | | 708.4 | 4D | XIV |
| 3E | | 664.4 | 5D | XIV |
| 4E | | 732.4 | 6D | XIV |
| 5E | | 800.3 | 7D | XV |
| 6E | | 708.4 | 8D | XIV |

TABLE E-continued

| Example | Compound | ES MS (M + 1) | Starting From | Procedure |
|---------|----------|---------------|---------------|-----------|
| 7E | | 683.3 | 9D | XIV |
| 8E | | 665.3 | 11D | XIV |
| 9E | | 651.3 | 12D | XIV |
| 10E | | 666.4 | 13D | XIV |
| 11E | | 720.3 | 14D | XIV |
| 12E | | 680.3 | 15D | XIV |

TABLE E-continued

| Example | Compound | ES MS (M + 1) | Starting From | Procedure |
|---|---|---|---|---|
| 13E | piperazine-N-X, 4-isobutyl-4-(piperazinyl)-1-(methylsulfonyl)piperidine | 744.3 | 16D | XIV |
| 14E | piperazine-N-X, 4-isobutyl-4-(piperazinyl)-1-ethylpiperidine | 694.4 | 17D | XIV |
| 15E | piperazine-N-X, 4-isobutyl-4-(piperazinyl)-1-isobutyrylpiperidine | 736.2 | 18D | XIV |
| 16E | piperazine-N-X, 4-isobutyl-4-(piperazinyl)-1-acetylpiperidine | 708.3 | 19D | XIV |
| 17E | piperazine-N-X, 4-isobutyl-4-(piperazinyl)-thiopyran-1,1-dioxide | 715.3 | 20D | XIV |

TABLE E-continued

| Example | Compound | ES MS (M + 1) | Starting From | Procedure |
|---|---|---|---|---|
| 18E | [structure: piperazine with N-X and N-(4-isopropyl-tetrahydropyran-4-yl)] | 653.3 | 21D | XIV |
| 19E | [structure: piperazine with N-X and N-(1-isopropylcyclohexyl)] | 651.3 | 22D | XIV |
| 20E | [structure: piperazine with N-X and N-(3-isobutyl-1-methylpiperidin-3-yl)] | 680.4 | 23D | XIV |

Procedure XVI

Preparation 1F

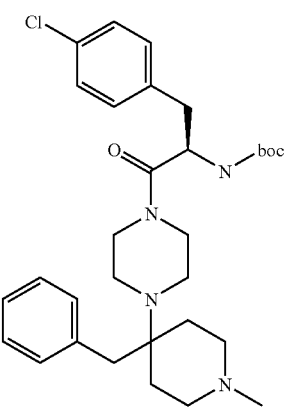

To compound 3D (0.404 g, 1.48 mmol) in CH$_2$Cl$_2$ (2 mL) was added Boc-4-Chloro-D-Phe (0.440 g, 1.48 mmol), EDCI (0.284 g, 1.48 mmol) and HOBT (0.199 g, 1.48 mmol). The mixture was stirred for 1 h, then diluted with EtOAc (50 mL) and washed with water (50 mL). The organics were separated and concentrated to dryness in vacuo. The resulting oil was purified by column chromatography (silica gel 60) eluting with EtOAc 100% to 90:5:5 (EtOAc:MeOH:Et$_3$N). The yield of compound 1F was 0.775 g, or 95% of theory.

Compounds 1F-3F were prepared from the appropriate N-substituted piperazines (1D-23D) and (Boc-4-Chloro-D-Phe acid) by following the procedure substantially similar to the Prcedure XVI.

TABLE F

| Example | Compound | ES MS (M + 1) | Starting From | Procedure |
|---------|----------|---------------|---------------|-----------|
| 1F | (4-Cl-phenyl)-CH2-CH(NHboc)-C(O)-N(piperazine)-C(4-phenyl-1-methylpiperidine) | 541.4 | 2D | XVI |
| 2F | (4-Cl-phenyl)-CH2-CH(NHboc)-C(O)-N(piperazine)-C(4-benzyl-1-methylpiperidine) | 555.3 | 3D | XVI |
| 3F | (4-Cl-phenyl)-CH2-CH(NHboc)-C(O)-N(piperazine)-C(4-isobutyl-tetrahydropyran) | 508.3 | 10D | XVI |

Procedure XVII

Preparation 2G

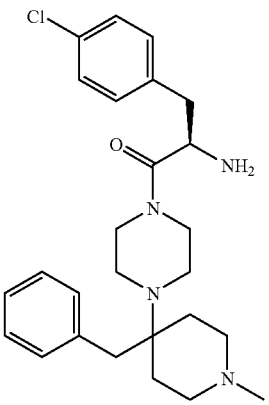

To a solution of compound 2F (0.775 g, 1.40 mmol) in CH$_2$Cl$_2$ (2 mL) was added TFA (2 mL). The solution sat for 2 h followed by concentration in vacuo. The resulting residue was diluted with water (20 mL) and made alkaline with 1M NaOH (20 mL). The aqueous phase was extracted with EtOAc (50 mL), separated and concentrated in vacuo. Compound 2G was collected cleanly as an oil (0.525 g, 83%).

Compounds 1G-3G were prepared from 1F-3F by following the procedure substantially similar to Prcedure XVII.

TABLE G

| Example | Compound | ES MS (M + 1) | Starting From | Procedure |
|---------|----------|---------------|---------------|-----------|
| 1G | | 441.4 | 1F | XVII |
| 2G | | 455.3 | 2F | XVII |

TABLE G-continued

| Example | Compound | ES MS (M + 1) | Starting From | Procedure |
|---------|----------|---------------|---------------|-----------|
| 3G | ![structure] | 408.3 | 3F | XVII |

Procedure XVIII

EXAMPLE 4H

N-[2-[4-(4-Benzyl-1-methyl-piperidin-4-yl)-piperazin-1-yl]-1-(4-chloro-benzyl)-2-oxo-ethyl]-2-(2-methyl-2,3-dihydro-1H-isoindol-1-yl)-acetamide (3HCl)

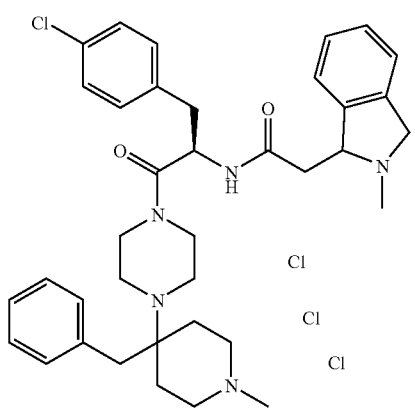

To compound 2G (0.525 g, 1.15 mmol) in $CH_2Cl_2$ (5 mL) was added EDCI (0.242 g, 1.27 mmol), HOBT (0.171 g, 1.27 mmol) and C7 (0.291 g, 1.27 mmol). The solution was stirred for 4 h then diluted with EtOAc (50 mL). Washed sequentially with $NaHCO_3$(aq) (50 mL) and water (50 mL). The organics were separated and concentrated to dryness. The resulting oil was purified by reverse phase column chromatography using a symmetry C18 column eluting with water (HCl buffer 0.05% and $CH_3CN$) 90:10 to 70:30. Compound of example 4H was collected as the HCl salt (0.450 g, 60%)

Compounds of examples 1H-5H were prepared from the appropriate primary amine of 1G-3G and acids C7, C2 and Boc-D-Tic by using the procedures substantially similar to XVI and XVIII as noted in the following table.

TABLE H
| Example | Compound | ES MS (M + 1) | Starting From | Procedure |
|---------|----------|---------------|---------------|-----------|
| 1H | 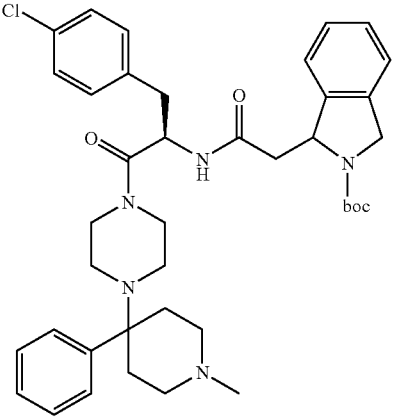 | 700.4 | 1G | XVI |
| 2H | 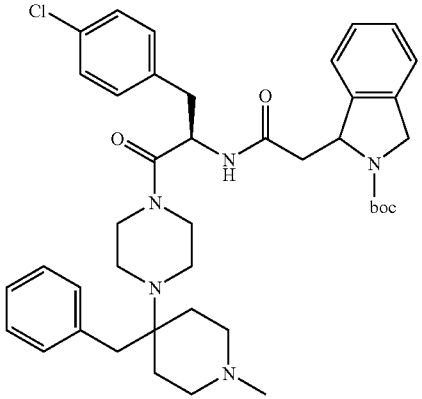 | 714.3 | 2G | XVI |
| 3H | 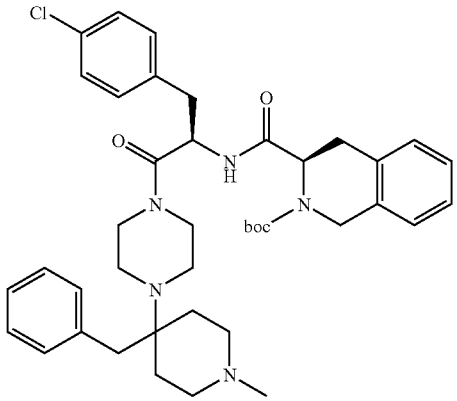 | 714.3 | 2G | XVI |

TABLE H-continued
| Example | Compound | ES MS (M + 1) | Starting From | Procedure |
|---|---|---|---|---|
| 4H | 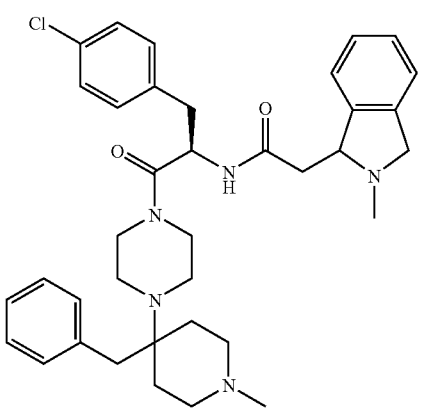 | 628.3 | 2G | XVIII |
| 5H | 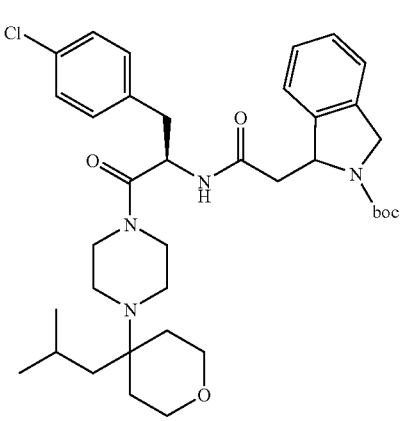 | 667.3 | 3G | XVI |

Procedure XIX

EXAMPLE 1I

N-{1-(4-Chloro-benzyl)-2-[4-(4-ethyl-1-methyl-piperidin-4-yl)-piperazin-1-yl]-2-oxo-ethyl}-2-(2,3-dihydro-1H-isoindol-1-yl)-acetamide

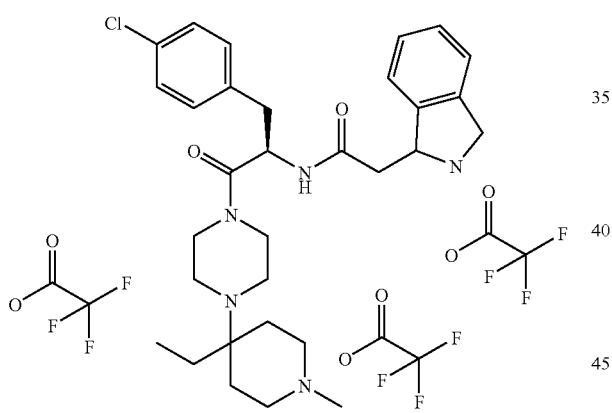

To a solution of compound 1E (0.150 g, 0.230 mmol) in CH$_2$Cl$_2$ (1 mL) was added TFA (1 mL). The solution stirred for 1 hour. The solution was concentrated to dryness in vacuo. The resulting oil was then triturated with Et$_2$O. The Et$_2$O was decanted and the solid dried under vacuum. Compound 1I was collected as a white solid (0.127 g, 62% of theory)

ES MS (M+1)=552.3

Procedure XX

EXAMPLE 24I

N-{1-(4-Chloro-benzyl)-2-[4-(2-isobutyl-indan-2-yl)-piperazin-1-yl]-2-oxo-ethyl}-2-(2,3-dihydro-1H-isoindol-1-yl)-acetamide dihydrochloride salt

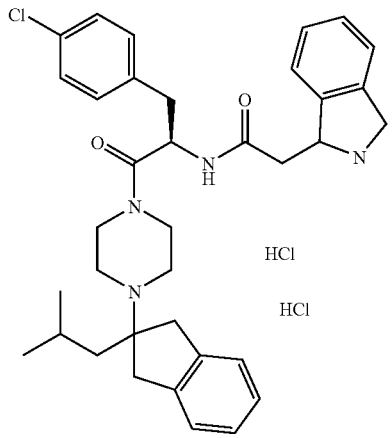

A solution of compound 24D (360 mg, 1.09 mmol), N-Boc-isoindoline-4-Cl-D-Phe (537 mg, 1.25 mmol), 1-hydroxy-7-azabenzotriazole (185 mg, 1.36 mmol), O-(7-azabenzotriazol-1-yl)-N,N,N',N'-tetramethyluronium hexafluorophosphate (516 mg, 1.36 mmol), and diisopropylethylamine (1.9 mL, 10.9 mmol) in CH$_2$Cl$_2$ (10 mL) and DMF (2.5 mL) was stirred at 23° C. for 16 h, diluted with CH$_2$Cl$_2$ and washed with brine, dried (Na$_2$SO$_4$), and evaporated. Purification by flash chromatography (hexane-EtOAc 4:1) gave rise to the coupled product. The Boc group was removed by stirring at room temperature in methylene chloride/TFA (1:1, 20 mL) for 2 hours. The solvent was evaporated and the residue purified by a SCX cartridge (MeOH→2M NH$_3$ in MeOH). The resulting oil was dissolved in 0.1 M HCl in EtOAc and stirred for 10 min. Final evaporation of the solvent afforded the desired product 2060431. MS m/z 599 (M$^+$+1).

Compounds of examples 2I-24I were prepared from the A-domain starting materials listed in table I below, using procedures substantially similar to Procedure XIX and XX. The hydrochloride salt can be prepared from the TFA salt by salt exchange in 0.5M HCl(aq) followed by lyophilization.

TABLE I

| Example | A | ES MS (M + 1) | Starting From | Procedure | Salt Form |
|---------|---|---------------|---------------|-----------|-----------|
| 1I | | 552.3 | 1E | XIX | TFA |
| 2I | | 608.3 | 2E | XIX | TFA |
| 3I | | 564.3 | 3E | XIX | TFA |
| 4I | | 632.3 | 4E | XIX | TFA |
| 5I | | 608.4 | 6E | XIX | TFA |
| 6I | | 583.3 | 7E | XIX | TFA |

TABLE I-continued

| Example | A | ES MS (M + 1) | Starting From | Procedure | Salt Form |
|---|---|---|---|---|---|
| 7I | | 565.3 | 8E | XIX | TFA |
| 8I | | 551.3 | 9E | XIX | TFA |
| 9I | | 566.3 | 10E | XIX | TFA |
| 10I | | 620.3 | 11E | XIX | HCl |
| 11I | | 580.3 | 12E | XIX | TFA |
| 12I | | 644.3 | 13E | XIX | TFA |

TABLE I-continued n*(salt form)

| Example | A | ES MS (M + 1) | Starting From | Procedure | Salt Form |
|---------|---|---------------|---------------|-----------|-----------|
| 13I | (4-(4-ethylpiperidin-1-yl)-4-isobutylpiperazine) | 594.4 | 14E | XIX | TFA |
| 14I | (4-(4-isobutyl-4-piperazin-1-yl-piperidin-1-yl)-2-methylpropan-1-one) | 636.3 | 15E | XIX | HCl |
| 15I | (1-(4-isobutyl-4-piperazin-1-yl-piperidin-1-yl)ethanone) | 608.3 | 16E | XIX | HCl |
| 16I | (4-isobutyl-4-piperazin-1-yl-tetrahydrothiopyran 1,1-dioxide) | 615.3 | 17E | XIX | HCl |
| 17I | (4-isopropyl-4-piperazin-1-yl-tetrahydropyran) | 553.3 | 18E | XIX | HGI |

TABLE I-continued n*(salt form)

| Example | A | ES MS (M + 1) | Starting From | Procedure | Salt Form |
|---|---|---|---|---|---|
| 18I | (piperazine-cyclohexyl-isopropyl) | 551.3 | 19E | XIX | TFA |
| 19I | (piperazine-piperidine-isobutyl, N-methyl) isomer 1 | 580.3 | 20E | XIX | HCl |
| 20I | (piperazine-piperidine-isobutyl, N-methyl) isomer 2 | 580.3 | 20E | XIX | HCl |
| 21I | (piperazine-piperidine-phenyl, N-methyl) | 600.4 | 1H | XIX | TFA |
| 22I | (piperazine-piperidine-benzyl, N-methyl) | 614.3 | 2H | XIX | TFA |

TABLE I-continued n*(salt form)

[Structure: 4-chlorobenzyl substituted compound with amide linkage to isoindoline, with variable group A]

| Example | A | ES MS (M + 1) | Starting From | Procedure | Salt Form |
|---------|---|---------------|---------------|-----------|-----------|
| 23I | [piperazine-tetrahydropyran with isobutyl] | 567.3 | 5H | XIX | TFA |
| 24I | [piperazine-indane with isobutyl] | 599 | 24D | XX | HCl |

Compounds 1J and 2J were prepared from compounds of examples 5E and 3H respectively by using the procedure substantially similar to Procedure XIX. The hydrochloride salt can be prepared from the TFA salt by salt exchange in 0.5M HCl(aq) followed by lyophilization.

TABLE J n*(salt form)

[Structure: 4-chlorobenzyl substituted compound with amide linkage to tetrahydroisoquinoline, with variable group A]

| Example | A | ES MS (M + 1) | Starting From | Procedure | Salt Form |
|---------|---|---------------|---------------|-----------|-----------|
| 1J | [piperazine-piperidine with benzyl] | 600.3 | 5E | XIX | TFA |

TABLE J-continued n*(salt form)

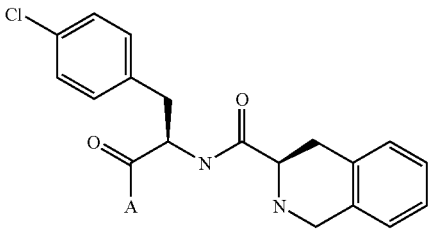

| Example | A | ES MS (M + 1) | Starting From | Procedure | Salt Form |
|---------|---|---------------|---------------|-----------|-----------|
| 2J | 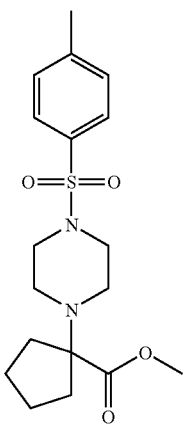 | 614.3 | 3H | XIX | TFA |

Procedure XXI

EXAMPLE 1EE

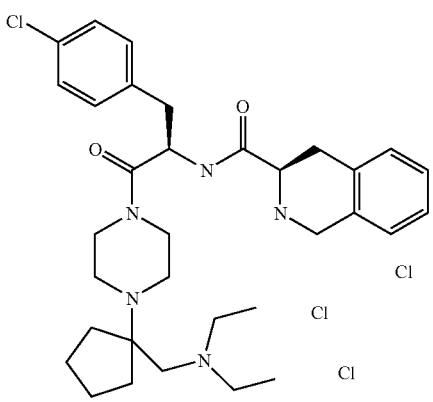

The compound of example 1EE was prepared using a procedure substantially similar to Procedure XX and starting materials originating from Preparations 1DD (below) and BC1.

Preparation 1AA

Compound 1AA

To a mixture of cyclopentanone (8.9 mL, 100.5 mmol) and $NH_4Cl$ (8.0 g, 150.8 mmol) at room temperature, a solution of KCN (9.8 g, 150.8 mmol) in $H_2O$ (75 mL) was added and the mixture was vigorously stirred for two days. Reaction was then poured onto a 2:1 mixture of $Et_2O$ and $H_2O$ (150 mL) and aqueous layer extracted with $Et_2O$ (3×50 mL). Combined organic layers were dried ($Na_2SO_4$), filtered and evaporated under reduced pressure to afford 1-amino-1-cyclopentanenitrile. This aminonitrile (2.0 g, 18.1 mmol) was dissolved in a saturated solution of HCl in methanol. To the resulting solution, $H_2O$ (0.98 mL, 54.5 mmol) was added and mixture stirred at room temperature for one week. Solvent was evaporated under reduced pressure, residue taken into MeOH (100 mL) and stirred for 5 minutes. Solvent was removed under reduced pressure and solid residue washed with $Et_2O$ to afford methyl 1-amino-1-cyclopentanecarboxylate hydrochloride. To a solution of methyl 1-amino-1-cyclopentanecarboxylate hydrochloride (3.2 g, 18.1 mmol) in anhydrous DMF (40 mL) and diisopropylethyl amine (100 mL), N,N-bis(2-chloroethyl)-p-toluenesulphonamide (5.9 g, 19.9 mmol) was added and reaction stirred under reflux (120° C.) for 3 days. Solvent was removed under reduced pressure and residue taken into ethyl acetate (200 mL). Organic layer was washed with H₂O (2×50 mL) and brine, dried (Na₂SO₄), filtered and evaporated. Residue was purified by column chromatography (hexane-AcOEt 1:4) to afford the title compound (10% overall yield) as a white solid. MS m/z 367.2 (M⁺+1).

Procedure XXII

Preparation 1BB

Compound 1BB

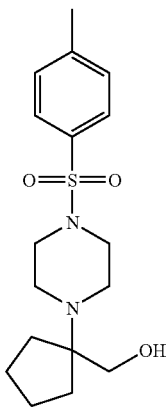

To an ice cooled solution of compound 1AA (550 mg, 1.5 mmol) in anhydrous THF (15 mL) under nitrogen was added lithium aluminum hydride (120 mg, 3.15 mmol) portion wise. After 10 minutes, mixture was allowed to react at room temperature for 1 h and then carefully quenched with H₂O (0.10 mL) and 2N NaOH (0.4 mL) at 0° C. The mixture was stirred for 30 minutes and then filtered through Celite. Solvent was removed under reduced pressure to afford the title compound (99%) as a white solid. MS m/z 339.2 (M⁺+1).

Procedure XXIII

Preparation 1CC

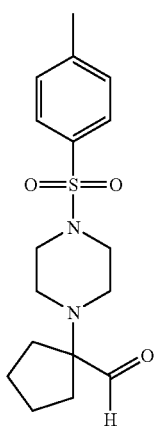

To a solution of oxalyl chloride (0.15 mL, 1.77 mmol) in anhydrous CH₂Cl₂ (15 mL) at −78° C. under nitrogen atmosphere, DMSO (0.27 mL, 3.75 mmol) was added dropwise and stirred for 30 minutes. To this mixture, a solution of the compound of Preparation 1BB in CH₂Cl₂ (3 mL) was added dropwise and reaction was stirred at the same temperature for 30 minutes. Then, Et₃N (1.05 mL, 7.5 mmol) was added and mixture allowed to react at room temperature. After 30 minutes, the reaction was quenched with H₂O, the layers were separated and the aqueous layer was extracted with CH₂Cl₂ (2×10 mL). The combined organic layers were dried (Na₂SO₄), filtered and evaporated to afford the title compound (99%). MS m/z 337.1 (M⁺+1).

Procedure XXIV

Preparation 1DD

Compound 1DD

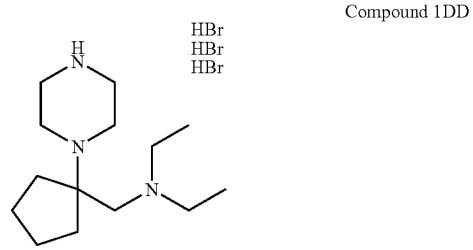

To a solution of Compound of preparation 1CC (450 mg, 1.34 mmol) and Et₂NH (0.15 mL, 1.47 mmol) in 1,2-dichloroethane (10 mL), sodium triacetoxyborohydride (400 mg, 1.9 mmol) was added in one portion. The mixture was stirred at room temperature for 3 days and then, additional Et₂NH (0.15 mL, 1.47 mmol) and sodium triacetoxyborohydride (400 mg, 1.9 mmol) were added. Reaction was stirred for 4 days and then quenched with saturated aqueous NaHCO₃ and extracted with CH₂Cl₂. Combined organic layers were dried (Na₂SO₄), filtered and evaporated to give a residue that was purified by column chromatography (hexane-EtOAc 1:1, then EtOAc, then EtOAc—MeOH-Et₃N 90:5:5) to afford the N-tosyl protected compound as a pale yellow oil. A solution of the N-tosyl derivative (220 mg, 0.56 mmol) in 30% HBr/AcOH (4.5 mL) was stirred at room temperature overnight. Solvent was evaporated under reduced pressure and solid residue washed with Et₂O to afford the title compound (38%) as a yellow solid. MS m/z 240.2 (M++1)

We claim:

1. A compound of formula I:

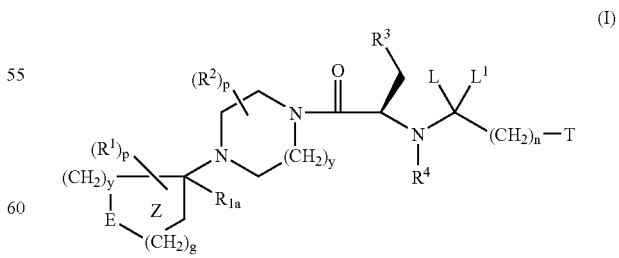

(I)

or a pharmaceutically acceptable salt, or stereoisomer thereof, wherein:

L and L¹ combine together to form an oxo group;

E is: O, S, NR$^{1b}$, SO, SO$_2$, CR$^9$, or C(R$^9$)$_2$ wherein R$^9$ combines with an adjacent R$^1$ to form a 5, 6, or 7-member saturated or unsaturated carbocycle;
wherein the Z ring has 0 or 1 double bond between the C(R$^9$) carbon and an adjacent carbon attached to R$^1$;
R$^1$ is selected from the group consisting of:
hydrogen, and
C$_1$-C$_8$ alkyl,
R$_{1a}$ is
C$_1$-C$_8$ alkyl,
(D)C$_3$-C$_7$ cycloalkyl,
(D)phenyl,
(D)aryl,
wherein C$_1$-C$_8$ alkyl, C$_3$-C$_7$ cycloalkyl, phenyl, and aryl are optionally substituted with one to five substituents independently selected from the group consisting of halo, hydroxy, C$_1$-C$_8$ alkyl, C$_1$-C$_4$ alkoxy, and C$_1$-C$_4$ haloalkyl; provided that halo and hydroxy groups are not substituted on a carbon atom adjacent to a heteroatom;
R$^{1b}$ is: hydrogen,
C$_1$-C$_8$ alkyl,
(D)C$_3$-C$_7$ cycloalkyl,
SO$_2$(C$_1$-C$_8$ alkyl),
(D)C(O)C$_1$-C$_4$ alkyl,
(D)C(O)OC$_1$-C$_4$ alkyl, or
SO$_2$(D)phenyl, wherein the phenyl group is optionally substituted with one to five substituents selected from halo, and C$_1$-C$_8$ alkyl;
R$^2$ is: hydrogen, or
C$_1$-C$_8$ alkyl;
R$^3$ is: phenyl, aryl or thienyl;
wherein phenyl, aryl and thienyl are optionally substituted with one to three substituents independently selected from the group consisting of:
cyano, perfluoroC$_1$-C$_4$ alkoxy, halo, C$_1$-C$_8$ alkyl, (D)C$_3$-C$_7$ cycloalkyl, C$_1$-C$_4$ alkoxy, C$_1$-C$_4$ haloalkyl;
R$^4$ is: hydrogen,
C$_1$-C$_8$ alkyl,
T is:

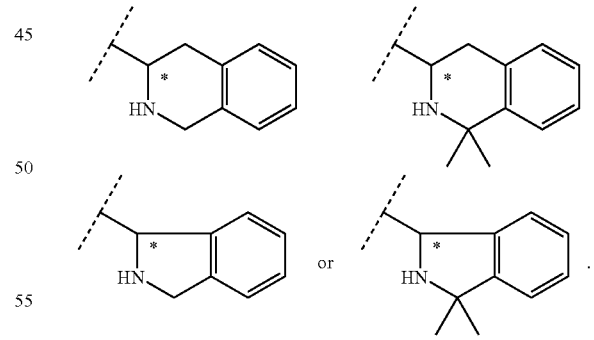

R$^9$ is independently:
hydrogen,
(C$_1$-C$_8$) alkyl,
C$_2$-C$_8$ alkenyl,
C(O)C$_1$-C$_8$ alkyl, or
phenyl,
R$^{10}$ is: hydrogen,
(C$_1$-C$_8$) alkyl,
C(O)C$_1$-C$_8$ alkyl, or
phenyl,
R$^{11}$ is independently:
hydrogen, (C$_1$-C$_8$) alkyl, (D)phenyl, or aryl;

R$^{12}$ is independently:
C$_1$-C$_8$ alkyl,
phenyl,
aryl;
D is: a bond or C$_1$-C$_4$ alkyl;
g is: 0, 1, or 2;
y is: 1
n is: 0-8; and
p is 0-4.

2. The compound according to claim 1 wherein the Z ring is saturated.

3. The compound according to claim 2 wherein E is O, S, NR$^{1b}$, or SO$_2$.

4. The compound according to claim 1 wherein for the Z ring R$^1$ is hydrogen.

5. The compound according to claim 1 wherein R$_{1a}$ is isopropyl, isobutyl, cyclohexylmethyl, phenyl, 2-fluorobenzyl or benzyl.

6. The compound according to claim 1 wherein E is selected from the group consisting of: —NCH$_3$, —NCH(CH$_3$)$_2$, S, CR$^9$, C(R$^9$)$_2$, —NCH$_2$CH$_3$, and O.

7. The compound according to claim 6 wherein E is C(R$^9$)$_2$, wherein one R$^9$ is selected from hydrogen and C$_1$-C$_4$ alkyl, and the other R$^9$ combines with an adjacent R$^1$ to form a 5 or 6-member carbocycle.

8. The compound according to claim 1 wherein R$^2$ is hydrogen.

9. The compound of claim 1 wherein R$^3$ is phenyl optionally being para-substituted with chloro, bromo, methoxy or methyl.

10. The compound of claim 9 wherein R$^3$ is phenyl para-substituted with chloro.

11. The compound of claim 1 wherein R$^{10}$ is hydrogen, C$_1$-C$_4$ alkyl, or C(O)C$_1$-C$_4$ alkyl.

12. The compound of claim 11 wherein R$^{10}$ is hydrogen at each occurrence.

13. The compound according to claim 1 wherein "T" is a moiety of the formula:

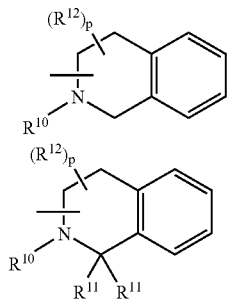

14. The compound according to claim 1 wherein "T" is a moiety selected from the group consisting of:

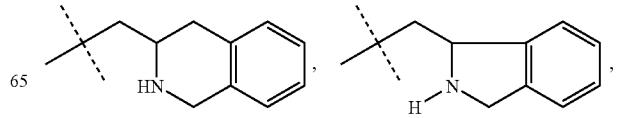

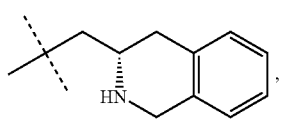

,and

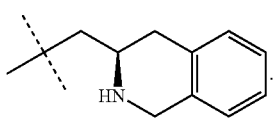

15. The compound of claim 1 wherein T is a moiety of the formula:

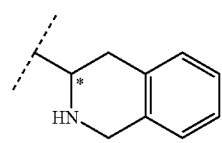

wherein the carbon atom marked * represents a chiral center.

16. A pharmaceutical composition comprising a compound of claim 1 and a pharmaceutical carrier.

17. The pharmaceutical composition of claim 16 further comprising a second active ingredient selected from the group consisting of an insulin sensitizer, insulin mimetic, sulfonylurea, alpha-glucosidase inhibitor, HMG-CoA reductase inhibitor, sequestrant cholesterol lowering agent, beta 3 adrenergic receptor agonist, neuropeptide Y antagonist, phosphodiester V inhibitor, and an alpha 2 adrenergic receptor antagonist.

18. A compound selected from the group consisting of:

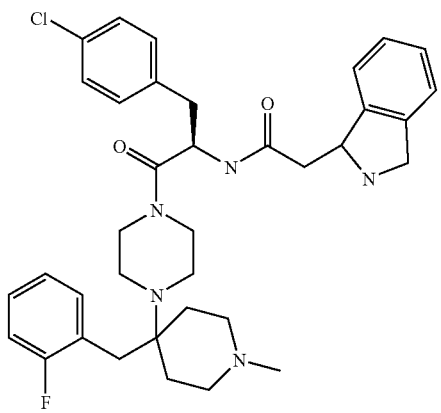

N-(1-(4-Chloro-benzyl)-2-{4-[4-(2-fluoro-benzyl)-1-methyl-piperidin-4-yl]-piperazin-1-yl}-2-oxo-ethyl)-2-(2,3-dihydro-1H-isoindol-1-yl)-acetamide,

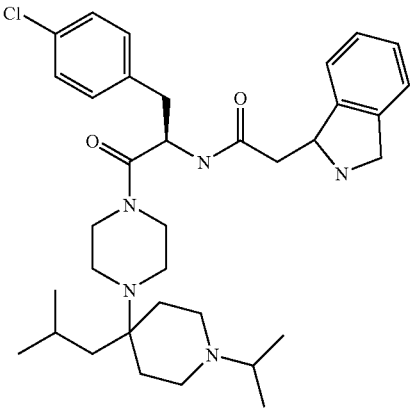

N-{1-(4-Chloro-benzyl)-2-[4-(4-isobutyl-1-isopropyl-piperidin-4-yl)-piperazin-1-yl]-2-oxo-ethyl}-2-(2,3-dihydro-1H-isoindol-1-yl)-acetamide,

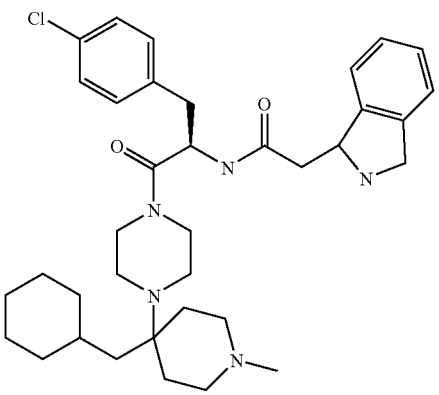

N-{1-(4-Chloro-benzyl)-2-[4-(4-cyclohexylmethyl-1-methyl-piperidin-4-yl)-piperazin-1-yl]-2-oxo-ethyl}-2-(2,3-dihydro-1H-isoindol-1-yl)-acetamide,

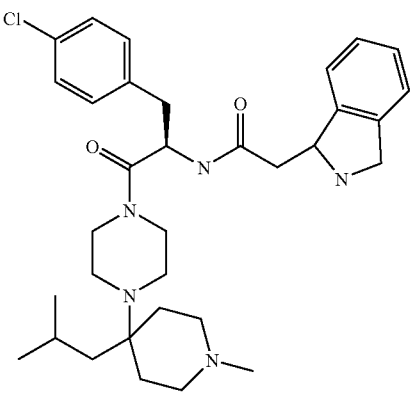

161

N-{1-(4-Chloro-benzyl)-2-[4-(4-isobutyl-1-methyl-piperidin-4-yl)-piperazin-1-yl]-2-oxo-ethyl}-2-(2,3-dihydro-1H-isoindol-1-yl)-acetamide,

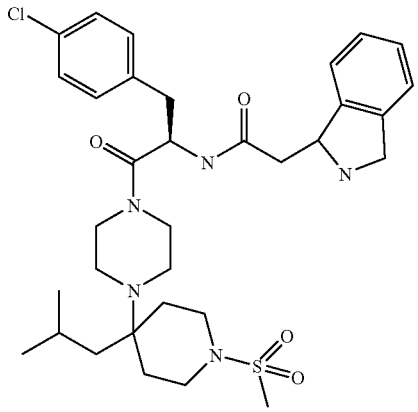

N-{1-(4-Chloro-benzyl)-2-[4-(4-isobutyl-1-methanesulfonyl-piperidin-4-yl)-piperazin-1-yl]-2-oxo-ethyl}-2-(2,3-dihydro-1H-isoindol-1-yl)-acetamide,

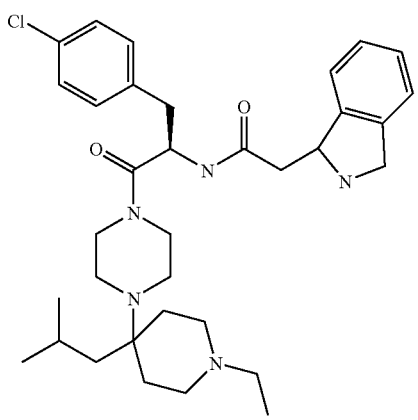

N-{1-(4-Chloro-benzyl)-2-[4-(1-ethyl-4-isobutyl-piperidin-4-yl)-piperazin-1-yl]-2-oxo-ethyl}-2-(2,3-dihydro-1H-isoindol-1-yl)-acetamide,

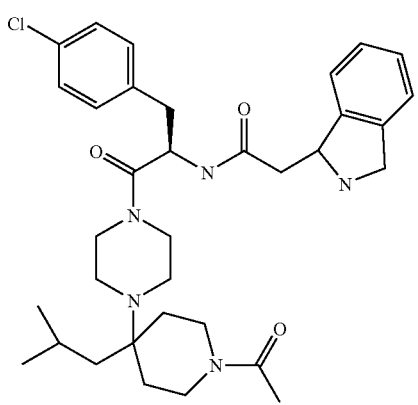

162

N-[2-[4-(1-Acetyl-4-isobutyl-piperidin-4-yl)-piperazin-1-yl]-1-(4-chloro-benzyl)-2-oxo-ethyl]-2-(2,3-dihydro-1H-isoindol-1-yl)-acetamide,

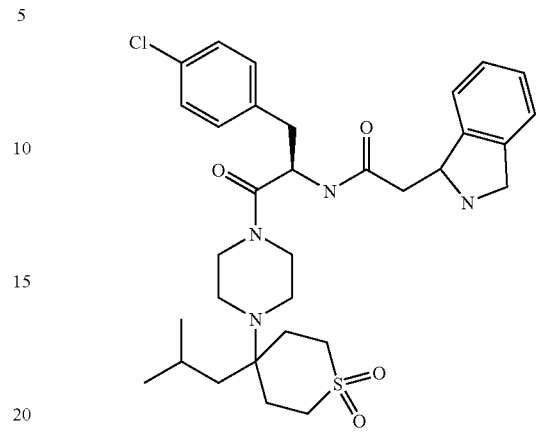

N-{1-(4-Chloro-benzyl)-2-[4-(4-isobutyl-1,1-dioxo-hexahydro-1l6-thiopyran-4-yl)-piperazin-1-yl]-2-oxo-ethyl}-2-(2,3-dihydro-1H-isoindol-1-yl)-acetamide, Isomer 1

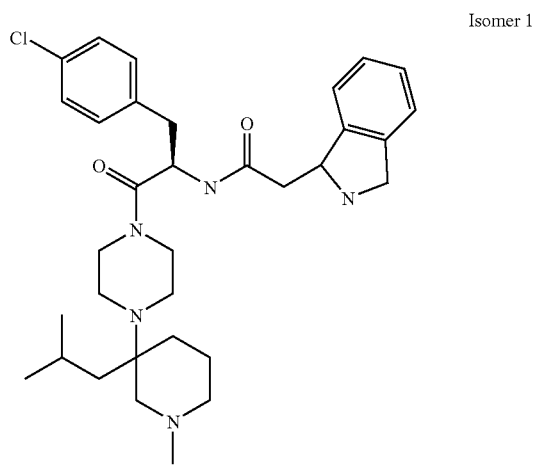

N-{1-(4-Chloro-benzyl)-2-[4-(3-isobutyl-1-methyl-piperidin-3-yl)-piperazin-1-yl]-2-oxo-ethyl}-2-(2,3-dihydro-1H-isoindol-1-yl)-acetamide, isomer 2

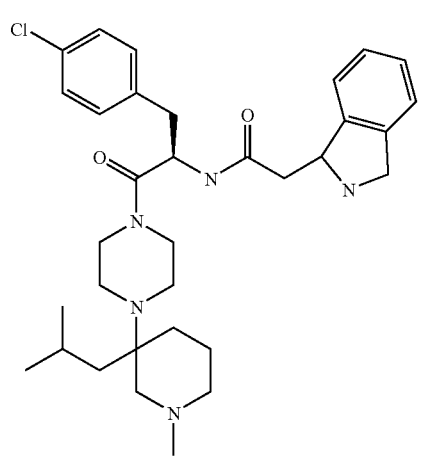

N-{1-(4-Chloro-benzyl)-2-[4-(3-isobutyl-1-methyl-piperidin-3-yl)-piperazin-1-yl]-2-oxo-ethyl}-2-(2,3-dihydro-1H-isoindol-1-yl)-acetamide,

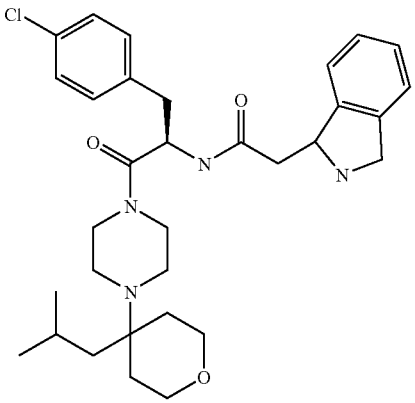

N-{1-(4-Chloro-benzyl)-2-[4-(4-isobutyl-tetrahydro-pyran-4-yl)-piperazin-1-yl]-2-oxo-ethyl}-2-(2,3-dihydro-1H-isoindol-1-yl)-acetamide.

19. A process for preparing a compound of formula I:

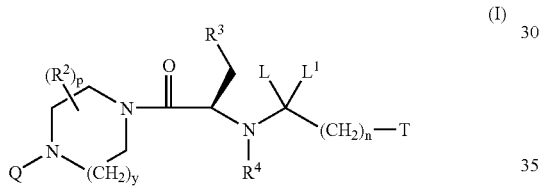

or a pharmaceutically acceptable salt or stereoisomer thereof, wherein:

—CLL'-(CH$_2$)$_n$-T is:

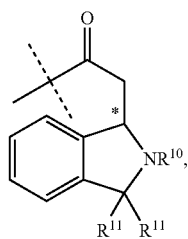

$R^{10}$ is a CBz or Boc protecting group, hydrogen, ($C_1$-$C_8$) alkyl, C(O)$C_1$-$C_8$ alkyl, or phenyl,;

Q is represented by the moiety:

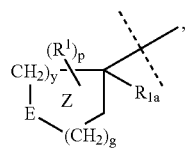

L and $L^1$ combine together to form an oxo group;

E is: O, S, NR$^{1b}$, SO, SO$_2$, CR$^9$, or C(R$^9$)$_2$, wherein R$^9$ combines with an adjacent R$^1$ to form a 5, 6, or 7-member saturated or unsaturated carbocycle;

wherein the Z ring has 0 or 1 double bond between CR$^9$ and an adjacent carbon attached to R$^1$;

$R^1$ is selected from the group consisting of:
hydrogen, and
$C_1$-$C_8$ alkyl, $R_{1a}$ is
C 1-$C_8$ alkyl,
(D)$C_3$-$C_7$ cycloalkyl,
(D)phenyl,
(D)aryl,
wherein $C_1$-$C_8$ alkyl, $C_3$-$C_7$ cycloalkyl, phenyl, and aryl are optionally substituted with one to five substituents independently selected from the group consisting of halo, hydroxy, $C_1$-$C_8$ alkyl, $C_1$-$C_4$ alkoxy, and $C_1$-$C_4$ haloalkyl; provided that halo and hydroxy groups are not substituted on a carbon atom adjacent to a heteroatom;

$R^{1b}$ is: hydrogen,
$C_1$-$C_8$ alkyl,
(D)$C_3$-$C_7$ cycloalkyl,
SO$_2$($C_1$-$C_8$ alkyl),
(D)C(O)$C_1$-$C_4$ alkyl,
(D)C(O)O$C_1$-$C_4$ alkyl, or
SO$_2$(D)phenyl, wherein the phenyl group is optionally substituted with one to five substituents selected from halo, and $C_1$-$C_8$ alkyl;

$R^2$ is: hydrogen, or
$C_1$-$C_8$ alkyl;

$R^3$ is: phenyl, aryl or thienyl;
wherein phenyl, aryl and thienyl are optionally substituted with one to three substituents independently selected from the group consisting of:
cyano, perfluoro$C_1$-$C_4$ alkoxy, halo, $C_1$-$C_8$ alkyl, (D)$C_3$-$C_7$ cycloalkyl, $C_1$-$C_4$ alkoxy, and $C_1$-$C_4$ haloalkyl;

$R^4$ is: hydrogen,
$C_1$-$C_8$ alkyl;

$R^9$ is independently hydrogen, ($C_1$-$C_8$) alkyl, $C_2$-$C_8$ alkenyl, C(O)$C_1$-$C_8$ alkyl, or phenyl;

R is independently:
hydrogen, ($C_1$-$C_8$) alkyl, (D)phenyl or aryl;

D is: a bond or $C_1$-$C_4$ alkyl;

g is: 0, 1, or 2;

y is: 1;

n is: 0-8; and p is 0-4:

comprising the steps of:
a) reacting a compound having a structural formula 1:

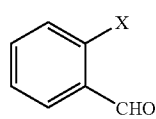

with CH2CH=C(O)OR$^a$ wherein R$^a$ is hydrogen or $C_1$-$C_8$ alkyl and X is halo, in the presence of a catalyst and a base in a suitable organic solvent to give the compound of formula 2:

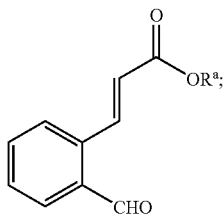

(2)

b) reductively aminating the compound of formula 2 in the presence of amine in an acidic condition to give a compound of formula 3:

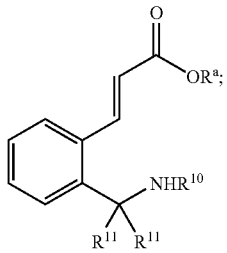

(3)

c) cyclizing the compound of formula 3 by Michael addition to give a compound of formula 4 or stereoisomers thereof:

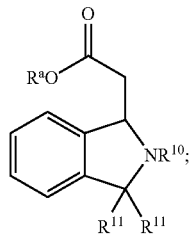

(4)

d) coupling the compound of formula 4 or stereoisomers thereof wherein $R^a$ is H, with a compound of formula 5:

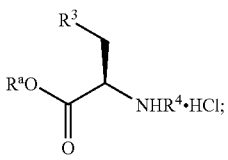

(5)

wherein $R^a$ is $C_1$-$C_8$ alkyl, to give a compound of formula 6:

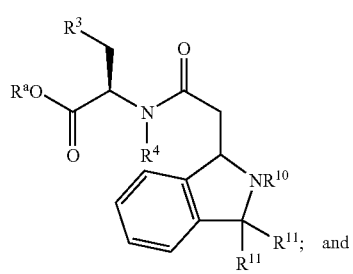

(6)

e) coupling the compound of formula 6 wherein $R^a$ is H, with a compound having a structural formula:

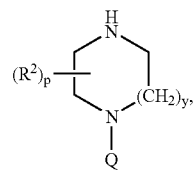

to afford the compound of formula 1.

20. The process of claim 19, wherein:

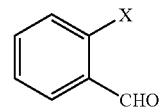

in Step a) is 2-bromobenzaldehyde.

21. The process of claim 19, wherein $CH_2CH{=}C(O)OR^a$ in Step (a) is methylacrylate.

22. The process of claim 19, wherein the catalyst in Step (a) is selected from the group consisting of: $Pd(Ph_3P)_2Cl_2$, $Pd(Ph_3P)_4Cl_2$, $Pd(Ph3P)_4$, $Pd(Ph_3\ P)_2Cl_2/CuI$, $Pd(OAc)_2/Ph_3P$-$Bu_4NBr$, $Pd(Ph_3P)_4Cl_2/H_2$ and $Pd(OAc)_2/P(O$-$tol)_3$; and wherein the base in Step (a) is $N(R)_3$ where R is hydrogen or $C_1$-$C_8$ alkyl.

23. The process of claim 19, wherein the amine in Step (b) is selected from the group consisting of: benzylamine, alpha-methylbenzylamine and BocNH$_2$.

24. The process of claim 23, wherein Step (b) further comprises the step of reducing an intermediate imine compound in the presence of reducing agent selected from the group consisting of: $NaCNBH_3$, $Na(OAc)_3BH$, $NaBH_4/H+$ and a combination of $Et_3SiH$ and TFA in $CH_3CN$ or $CH_2Cl_2$.

25. The process of claim 19, wherein the stereoisomer of compound of formula (4) in Step (c) is a compound of formula 7a:

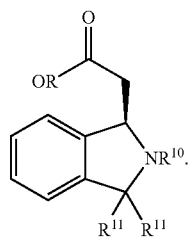

(7a)

26. The process of claim 25, wherein the compound of formula 7a is prepared by asymmetric hydrogenation of a compound having structural formula,

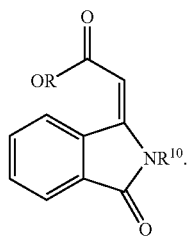

27. The process of claim 19, wherein the Michael addition in Step (c) is carried out under basic workup condition.

28. The process of claim 19, wherein the Step (e) further comprises deprotecting or protecting the nitrogen of the $NR^{10}$ substituent.

29. A method of treating obesity in a mammal comprising the administration of a therapeutically effective amount of the compound of formula I as recited in claim 1.

* * * * *